(12) United States Patent
Delhomel et al.

(10) Patent No.: US 11,974,997 B2
(45) Date of Patent: May 7, 2024

(54) RORGAMMA MODULATORS AND USES THEREOF

(71) Applicant: Genfit, Loos (FR)

(72) Inventors: Jean-Francois Delhomel, Arras (FR); Enrico Perspicace, Phalempin (FR); Zouher Majd, Ennetieres-en-Weppes (FR); Peggy Parroche, Loos (FR); Robert Walczak, Lille (FR); Pascal Bonnet, Olivet (FR); Jade Fogha, Nanterre (FR)

(73) Assignee: Genfit, Loos (FR)

( * ) Notice: Subject to any disclaimer, the term of this patent is extended or adjusted under 35 U.S.C. 154(b) by 143 days.

(21) Appl. No.: 17/494,458

(22) Filed: Oct. 5, 2021

(65) Prior Publication Data

US 2022/0133716 A1     May 5, 2022

Related U.S. Application Data

(62) Division of application No. 16/481,172, filed as application No. PCT/EP2018/052163 on Jan. 29, 2018, now Pat. No. 11,160,801.

(30) Foreign Application Priority Data

Jan. 27, 2017 (EP) ..................................... 17305091
Jun. 29, 2017 (EP) ..................................... 17178889

(51) Int. Cl.
*C07D 405/14* (2006.01)
*A61K 31/192* (2006.01)
*A61K 31/40* (2006.01)
*A61K 31/4184* (2006.01)
*A61K 31/4439* (2006.01)
*A61K 31/496* (2006.01)
*A61K 31/506* (2006.01)

(52) U.S. Cl.
CPC .......... *A61K 31/496* (2013.01); *A61K 31/192* (2013.01); *A61K 31/40* (2013.01); *A61K 31/4184* (2013.01); *A61K 31/4439* (2013.01); *A61K 31/506* (2013.01); *C07D 405/14* (2013.01)

(58) Field of Classification Search
CPC ............................ A61K 31/496; C07D 405/14
See application file for complete search history.

(56) References Cited

FOREIGN PATENT DOCUMENTS

WO    WO-2014/062938 A1    4/2014
WO    WO-2017/010399 A1    1/2017

*Primary Examiner* — Paul V Ward
(74) *Attorney, Agent, or Firm* — Morse, Barnes-Brown & Pendleton, P.C.; Martin Z. Zhang, Esq.

(57) ABSTRACT

The present invention provides novel compounds that are modulators of RORgamma. These compounds, and pharmaceutical compositions comprising the same, are suitable means for treating any disease wherein the modulation of RORgamma has therapeutic effects, for instance in autoimmune diseases, autoimmune-related diseases, inflammatory diseases, metabolic diseases, fibrotic diseases, or cholestatic diseases.

14 Claims, 6 Drawing Sheets

RORGAMMA MODULATORS AND USES THEREOF

CROSS-REFERENCE TO RELATED APPLICATIONS

This application is a divisional of U.S. application Ser. No. 16/481,172, filed Jul. 26, 2019, which is the National Stage of International Application No. PCT/EP2018/052163, filed Jan. 29, 2018, claiming priority to European Application No. 17305091.5, filed Jan. 27, 2017, and European Application No. 17178889.6, filed Jun. 29, 2017. The contents of these prior applications are hereby incorporated by reference in their entirety.

TECHNICAL FIELD

The present invention relates to novel compounds that are modulators of RORgamma and the pharmaceutical use of such compounds.

BACKGROUND

The retinoic acid-related orphan receptor γ (RORγ) is a member of the ROR subfamily of nuclear receptors which includes three genes; RORA, RORB and RORC (also known as RORγ). rorγ gene encodes two isoforms RORγ1 and RORγ2 (also termed RORγt). RORγ1 is preferentially expressed in skeletal muscle and several other tissues, including pancreas, thymus, prostate, liver and testis (Hirose et al, 1994; Ortiz et al, 1995). RORγt is restricted to several distinct immune cell types (He et al, 1998). This immune system-specific isoform (RORγt) is the key lineage-defining transcription factor for the differentiation program of T helper type 17 (Th17) cells, a subset of CD4+ T-helper and the most prominent cells in producing a number of inflammatory cytokines, such as IL-17A, IL-17F, IL-22, and IL-23 considered as important pathogenic factors for many immune and inflammatory diseases. During the disease process Th17 cells are activated and are responsible for recruiting other inflammatory cell types, such as neutrophils, to mediate pathology in the target tissues (Korn et al, 2009). RORγt is also able to induce IL-17A and IL-17F in naïve CD4+ T-helper, NKT and iNKT cells (Rachitskaya et al, 2008), γδT cells (Murdoch & Lloyd, 2010), CD8+ Tcells (Liu et al, 2007) and CD4-CD8+TCRab+T cells (Crispín et al, 2008). RORγt is also expressed in and is required for the generation of LTi cells (Eberl et al, 2004), which are central to the development of lymphoid organs such as lymph node and Peyer's patch (Lipp & Muller, 2004).

Overexpression of RORγt in naïve CD4+ T cells was demonstrated to drive the induction and development of Th17 cells. In contrast, RORγt deficiency in mice completely impairs Th17 cell differentiation and induces resistance to the development of autoimmune diseases, such as experimental autoimmune encephalomyelitis (EAE) a model of multiple sclerosis (Dang et al, 2011; Yang et al, 2008) or experimental autoimmune myocarditis (EAM) (Yamashita et al, 2011). In the same manner, mice lacking IL-17 are resistant to development of EAE, and collagen-induced arthritis (CIA), a model of rheumatoid arthritis. IL-17 neutralization with a targeted antibody suppresses autoimmune inflammation, joint damage, and bone destruction (Furuzawa-Carballeda et al, 2007; Lubberts et al, 2004; Stockinger et al, 2007). Moreover, blocking Th17 pathway demonstrated good efficacy in patients with some chronic inflammatory diseases. For example, the anti-p40 monoclonal antibody Ustekinumab (Stelara) that targets Th17 and Th1 through IL-23 and IL-12 respectively, has been approved for the treatment of moderate to severe plaque psoriasis in adult patients and showed a clinical (phase IIb) efficacy in refractory Crohn diseased patients (Tuskey & Behm, 2014).

Small molecule RORγt modulators have therapeutic effects in preclinical disease models. In particular, compounds TMP778 and SR1001 were efficacious in psoriasis and multiple sclerosis models, respectively, when administered by injection (Skepner et al, 2014; Solt et al, 2011). Recently, Vitae Pharma has announced that a small molecule RORgt inverse agonist VTP-43742 reduced the Psoriasis Area Severity Index (PASI) score and plasma IL-17 levels, relative to placebo, in patients with moderate to severe psoriasis.

To summarise, RORγt activity modulation results in the modulation of IL-17 dependent immune and inflammatory responses.

Currently, there is considerable evidence suggesting that RORγt/IL-17 component is closely associated with a range of chronic inflammatory diseases such as multiple sclerosis (MS), psoriasis, inflammatory bowel diseases (IBD), rheumatoid arthritis (RA), uveitis and lung diseases. Compounds able to modulate RORγt activity are also expected to provide a therapeutic benefit in the treatment of numerous medical disorders, including autoimmune, inflammatory, fibrotic and cholestatic disorders, such as asthma, ankylosing spondylitis, autoimmune cardiomyopathy, autoimmune hepatitis, Crohn's disease, chronic obstructive proliferative disease (COPD), diabetes mellitus type 1, lupus erythematosus, lupus nephritis, multiple sclerosis, psoriasis, psoriatic arthritis, rheumatoid arthritis, ulcerative colitis, myocarditis, pulmonary fibrosis (idiopathic pulmonary, interstitial lung, cystic and progressive massive fibrosis), Non Alcoholic Fatty Liver Disease (NAFLD), NonAlcoholic SteatoHepatitis (NASH) and Alcoholic SteatoHepatitis (ASH), cardiac fibrosis and heart myocardial and endomyocardial fibrosis, arterial fibrosis, atherosclerosis/restenosis, intestinal fibrosis (occurs for example in Crohn's disease and collagenous colitis), kidney fibrosis, scleroderma and systemic sclerosis Primary Biliary Cholangitis (PBC), primary sclerosisng cholangitis (PSC), billiary artesia, Progressive familial intrahepatic cholestasis (PFIC), Hepatitis (hepatitis A, hepatitis B, hepatitis C).

The present invention describes novel RORγt modulators, their preparation and their use in therapy, in particular in the treatment of immune, inflammatory, metabolic, fibrotic and cholestatic diseases.

SUMMARY OF INVENTION

RORγ inverse agonists were proposed in Skepner et al., 2014 who allegedly showed that compound T was efficacious in psoriasis model when administered by injection.

Recently, data from a Phase 2a proof-of-concept clinical trial with RORgt inverse agonist (VTP-43742) were reported (Vitae Pharma press release). VTP-43742 demonstrated a clear signal of efficacy, with patients in the 350 mg dose group achieving a 24 percent reduction in the Psoriasis Area Severity Index (PASI) score relative to placebo. In the 700 mg dose group, patients achieved a 30 percent placebo-adjusted PASI score reduction.

The present invention thus provides novel compounds that are modulators of RORγ and have the following formula (I).

The present invention also provides pharmaceutical compositions comprising the compounds of formula (I) since they modulate RORγ in vitro and in cellular models, indicating that these compounds have properties of pharmaceutical interest. Accordingly, further objects of the invention include methods of treatment comprising the administration of said pharmaceutical composition for the treatment of RORγ-related diseases such as autoimmune, inflammatory diseases, metabolic, fibrotic and cholestatic diseases.

The present invention also provides a compound of formula (I), for use as a medicament.

The present invention also provides a compound of formula (I), for use in a method for the treatment of RORγ-related diseases.

Further objects of the present invention, including preferred compounds of formula (I), methods of preparing compounds of formula (I) and preferred medical uses or methods, in combination or not with other compounds, are provided in the Detailed Description.

DESCRIPTION OF THE FIGURES

Abbreviations Used in the Figures and in the Text:
ACLF acute-on-chronic liver failure
ADME absorption, distribution, metabolism, and excretion
ALF acute liver failure
ASH Alcoholic SteatoHepatitis
CD Cluster of Differentiation
CDCl3 deuterated chloroform
CFA Complete Freund's Adjuvant
CH2Cl2 Dichloromethane
CIA collagen-induced arthritis
CMC CarboxyMethyl Cellulose
CNS Conserved non coding sequence
COPD chronic obstructive proliferative disease
Cpd. Compound
DIPEA N,N-Diisopropylethylamine
DMAP 4-(DiMethylAmino)Pyridine
DMEM Dulbecco's modified Eagle's medium
DMF DiMethylFormamide
DMSO DiMethyl SulfOxide
eADME Early Absorption, Distribution, Metabolism, and Excretion
EAE experimental autoimmune encephalomyelitis
EAM Experimental Autoimmune Myocarditis
EDCI.HCl N-Ethyl-N'-(3-Dimethylaminopropyl)Carboddmide HydroChloride
equiv equivalent
EtOAc Ethyl acetate
H2O water
HCl Hydrochloric acid
HPLC High Performance Liquid Chromatography
IBD Inflammatory Bowel Diseases
IC$_{50}$ Half maximal inhibitory concentration
ICP Intarhepatic Cholestasis of Pregnancy
IL-12 interleukin 12
IL-17 interleukin 17
IL-23 interleukin 23
IUPAC International Union of Pure and Applied Chemistry
LCMS Liquid Chromatography-Mass Spectrometry
Me3SiCl Trimethylsilyl chloride
MeOH Methanol
mg miligramme
MgSO4 Magnesium sulphate
min minute
mL mililiter
μL microliter
mmol milimol
MOG Myelin Oligodendrocyte Glycoprotein
mp melting point
NAFLD non-alcoholic fatty liver disease
NaHCO3 Sodium bicarbonate
NaOH Sodium hydroxide
NASH NonAlcoholic SteatoHepatitis
NH4Cl ammonium chloride
NMR nuclear magnetic resonance
NR Nuclear Receptor
PBC Primary Biliary Cholangitis
PCR Polymerase Chain Reaction
Pd2(dba)3 Tris(dibenzylideneacetone)dipalladium(0)
Pd(OAc)2 Palladium(II) acetate
PMA Phorbol 12-Myristate 13-Acetate
ppm parts-per-million
PSC Primary Sclerosing Cholangitis
RA Rheumatoid Arthritis
ROR Retinoic Acid-Related Orphan Receptor
RPMI Roswell Park Memorial Institute medium
rt room temperature
sat. saturated
SIRS systemic inflammatory response syndrome
SPF Specific Pathogen Free
Th17 T helper 17
THF TetraHydroFuran
TLC Thin-Layer Chromatography
UV ultra-violet
XPhos Dicyclohexylphosphino-2',4',6'-triisopropylbiphenyl FIGS. 1A-1L and 2—Intermediate Compounds for the Synthesis of the Compounds of Formula (I)

Intermediates are independently generated for the synthesis of compounds of formula (I): for example 2-[6-(4-methanesulfonylpiperazin-1-yl)pyridin-3-yl]acetic acid Ex.1 (FIG. 1A), 2-[6-(4-methanesulfonylpiperidin-1-yl)pyridin-3-yl]acetic acid Ex.3 (FIG. 1B), 2-(6-{4-[(tert-butoxy)carbonyl]piperazin-1-yl}pyridin-3-yl)acetic acid Ex.4 (FIG. 1C), 2-[2-(4-methanesulfonylpiperazin-1-yl)pyrimidin-5-yl]acetic acid hydrochloride Ex.5 (FIG. 1D), 2-[2-(4-methanesulfonylpiperidin-1-yl)pyrimidin-5-yl]acetic acid Ex.6 (FIG. 1E), 2-[2-(4-acetylpiperidin-1-yl)pyrimidin-5-yl]acetic acid Ex.7 (FIG. 1F), 2-{2-[4-(methoxycarbonyl)piperidin-1-yl]pyrimidin-5-yl}acetic acid Ex.9 (FIG. 1G), 1-[2-(4-acetylpiperazin-1-yl)pyrimidin-5-yl]cyclopropane-1-carboxylic acid Ex.10 (FIG. 1H), 2-[2-(4-acetylpiperazin-1-yl)pyrimidin-5-yl]acetic acid Ex.11 (FIG. 1I), 2-[5-(4-acetylpiperazin-1-yl)pyridin-3-yl]acetic acid Ex.12 (FIG. 1J), 2-[2-(4-acetylpiperazin-1-yl)pyrimidin-4-yl]acetic acid Ex.13 (FIG. 1K) and 2-[2-(3-methanesulfonylpiperidin-1-yl)pyrimidin-5-yl]acetic acid Ex.14 (FIG. 1L).

Figure 2:
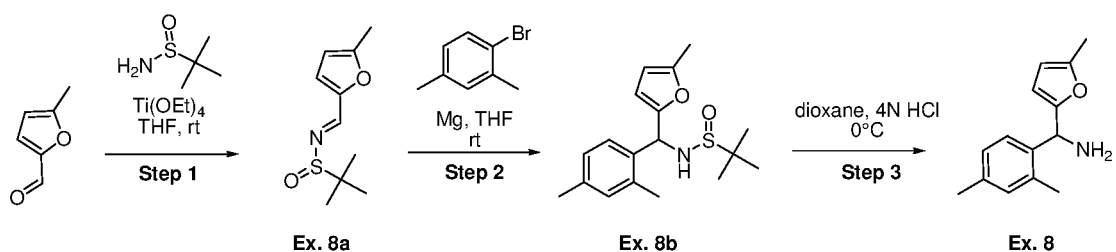

In a same manner was synthetised (2,4-dimethylphenyl)(5-methylfuran-2-yl)methanamine Ex.8 (FIG. 2)

Figure 3:
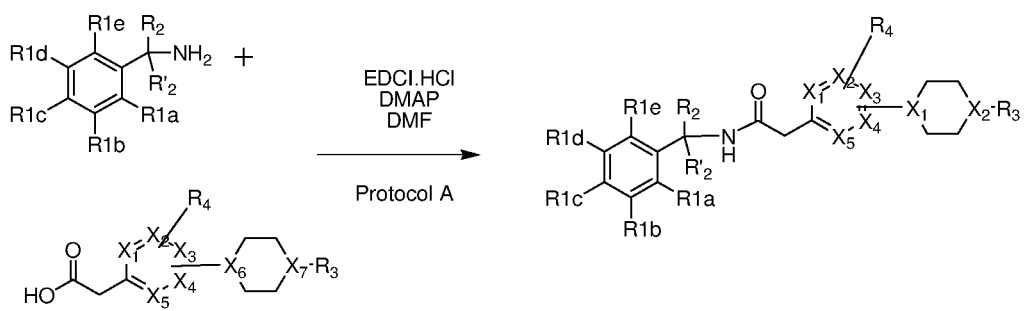

FIG. 3—General Synthesis Scheme of Compounds of Formula (I)

Compounds of formula (I) are generated using the Protocol A summarized in (FIG. 3).

DETAILED DESCRIPTION OF THE INVENTION

The present invention provides novel compounds that are modulators of RORgamma. These compounds, and pharmaceutical compositions comprising the same, are suitable for treating any disease wherein the RORgamma activity is involved, for instance in multiple autoimmune, inflammatory, metabolic, fibrotic and cholestatic disorders.

The compounds according to the invention have the following formula (I):

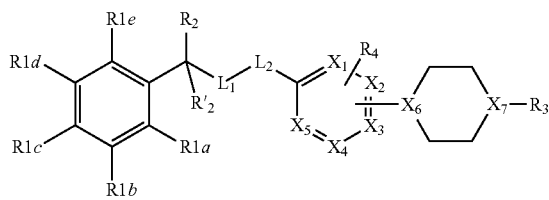

(I)

in which,

R1a is a hydrogen atom, a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, or a heterocyclic group;

R1b is a hydrogen atom, a (C1-C6)alkyloxy group, a (C1-C6)alkyl group or a heterocyclic group;

R1c is a hydrogen atom, a halogen atom, a (C1-C6)alkyl group, a (C1-C6)alkyloxy group, a (C1-C6)alkylthio group, a heterocyclic group, a cyano group, an amido group or a hydroxyl group;

R1d and R1e are, independently, a hydrogen atom, a halogen atom, a (C1-C6)alkyloxy group or a (C1-C6)alkyl group;

R2 is a (C1-C6)alkyl group optionally substituted by a (C1-C6)alkyl group, a (C2-C6)alkenyl group optionally substituted by a (C1-C6)alkyl group, a (C2-C6)alkynyl group optionally substituted by a (C1-C6)alkyl group, a (C3-C14)cycloalkyl group optionally substituted by a (C1-C6)alkyl group, a (C6-C14)aryl group optionally substituted by a (C1-C6)alkyl group or a heterocyclic group optionally substituted by a (C1-C6)alkyl group;

R'2 is a hydrogen atom, a (C1-C6)alkyl group, a (C2-C6)alkenyl group, a (C2-C6)alkynyl group, a (C3-C14)cycloalkyl group, a (C6-C14)aryl group or a heterocyclic group optionally substituted by a (C1-C6)alkyl group;

or R2 and R'2 can form, together with the carbon atom to which they are attached, a cycloalkyl group or a heterocycloalkyl group;

L1 is a NR7-CO—CH2, NR7-CO—, NR7-CO—C(CH3)2, CO—NH—CH2, CO—NH or CO—NH—C(CH3)2 group;

R7 is a hydrogen atom or a (C1-C6)alkyl group;

L2 represents a bond, a (C1-C6)alkyl group, a (C3-C14)cycloalkyl group or a CR8R'8 group;

R8 and R'8 are independently, a hydrogen atom, or a (C1-C6)alkyl group;

R8 and R'8 can optionally form, together with the carbon atom to which they are attached, a cycloalkyl group;

X1, X2, X3, X4, X5 are, independently, a CH group, a C—R4 group, a C—X6 group or a nitrogen atom;

X6 and X7 are independently a CH group or a nitrogen atom;

R3 is a hydrogen atom, a carbonyl(C1-C6)alkyl group, a SO2R' group, a COOR' group, an amido group, a (C1-C6)alkylamido group, or a (C1-C6)dialkylamidogroup;

R' is a (C1-C6)alkyl group; and

R4 is a hydrogen atom, a (C1-C6)alkyl group, or a halogen atom.

The present invention also relates to a compound of formula (I):

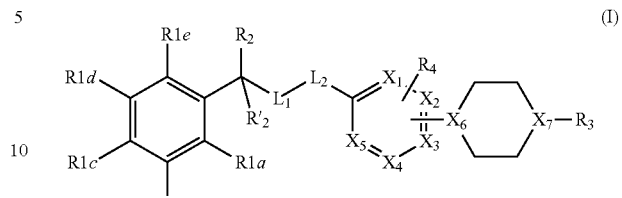

(I)

in which,

R1a is a hydrogen atom, a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, or a heterocyclic group;

R1b is a hydrogen atom, a (C1-C6)alkyloxy group, a (C1-C6)alkyl group or a heterocyclic group;

R1c is a hydrogen atom, a halogen atom, a (C1-C6)alkyl group, a (C1-C6)alkyloxy group, a (C1-C6)alkylthio group, a heterocyclic group, a cyano group, an amido group or a hydroxyl group;

R1d and R1e are, independently, a hydrogen atom, a halogen atom, a (C1-C6)alkyloxy group or a (C1-C6)alkyl group;

wherein at least one R1a, R1b, R1c, R1d, and R1e is not a hydrogen atom;

R2 is a (C1-C6)alkyl group optionally substituted by a (C1-C6)alkyl group, a (C2-C6)alkenyl group optionally substituted by a (C1-C6)alkyl group, a (C2-C6)alkynyl group optionally substituted by a (C1-C6)alkyl group, a (C3-C14)cycloalkyl group optionally substituted by a (C1-C6)alkyl group, a (C6-C14)aryl group optionally substituted by a (C1-C6)alkyl group or a heterocyclic group optionally substituted by a (C1-C6)alkyl group;

R'2 is a hydrogen atom, a (C1-C6)alkyl group, a (C2-C6)alkenyl group, a (C2-C6)alkynyl group, a (C3-C14)cycloalkyl group, a (C6-C14)aryl group optionally substituted by a (C1-C6)alkyl group or a heterocyclic group optionally substituted by a (C1-C6)alkyl group;

or R2 and R'2 can form, together with the carbon atom to which they are attached, a cycloalkyl group or a heterocycloalkyl group;

L1 is a NR7-CO—CH2, NR7-CO—, NR7-CO—C(CH3)2, CO—NH—CH2, CO—NH or CO—NH—C(CH3)2 group;

R7 is a hydrogen atom or a (C1-C6)alkyl group;

L2 represents a bond, a (C1-C6)alkyl group, a (C3-C14)cycloalkyl group or a CR8R'8 group;

with the proviso that when L1 is a NR3-CO— or a CO—NH group, L2 represents a (C1-C6)alkyl group, a (C3-C14)cycloalkylgroup, or a CR8R'8 group;

R8 and R'8 are independently, a hydrogen atom, or a (C1-C6)alkylgroup;

R8 and R'8 can optionally form, together with the carbon atom to which they are attached, a cycloalkyl group;

X1, X2, X3, X4 and X5 are, independently, a CH group, a C—R4 group, a C—X6 group or a nitrogen atom;

wherein at least one X1, X2, X3, X4, and X5 is a nitrogen atom;

X6 and X7 are independently a CH group or a nitrogen atom;

R3 is a hydrogen atom, a carbonyl(C1-C6)alkyl group, a SO2R' group, a COOR' group, an amido group, a (C1-C6)alkylamido group, or a (C1-C6)dialkylamidogroup;

R' is a (C1-C6)alkyl group; and

R4 is a hydrogen atom, a (C1-C6)alkyl group, or a halogen atom.

In particular embodiments, in the compound of formula (I) of the present invention:

a (C1-C6)alkyl group may be a substituted or unsubstituted (C1-C6)alkyl group, in particular a substituted or unsubstituted (C1-C4)alkyl group;

a (C1-C6)alkyloxy group may be a substituted or unsubstituted (C1-C6)alkyloxy group, in particular a substituted or unsubstituted (C1-C4)alkyloxy group;

a (C6-C14)aryl group may be a substituted or unsubstituted (C6-C14)aryl group;

a heterocyclic group may be a substituted or unsubstituted heterocycloalkyl or heteroaryl group.

The present invention also includes stereoisomers (diastereoisomers, enantiomers), pure or mixed, as well as racemic mixtures and geometric isomers, or tautomers of compounds of formula (I). The invention further includes salts, solvates (in particular hydrates) and polymorphs or crystalline forms of the compounds of formula (I).

According to a particular embodiment, the invention relates to a compound of formula (I) wherein R1a is a hydrogen atom, a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, a piperidinyl group, a pyrrolidinyl group, or an azepanyl group, wherein said piperidinyl, pyrrolidinyl or azepanyl group can be optionally substituted by at least one (C1-C6)alkyl groups.

In another particular embodiment, R1a is a hydrogen atom, a (C1-C6)alkyl group or a piperidinyl group (such as a piperidin-1-yl group). In a further particular embodiment, R1a is a (C1-C6)alkyl group or a piperidinyl group (such as a piperidin-1-yl group).

In a particular embodiment, R1b is a hydrogen atom.

In a particular embodiment, R1c is a (C1-C6)alkyl group.

In a particular embodiment, R1d is a hydrogen atom.

In a particular embodiment, R1e is a hydrogen atom.

In a particular embodiment, R1d and R1e are hydrogen atoms.

In a particular embodiment, R1b, R1d and R1e are hydrogen atoms.

In another particular embodiment, R2 is a (C1-C6)alkyl group, a (C3-C14)cycloalkyl group, an aryl group or a heteroaryl group. In another particular embodiment, R2 is a heteroaryl group, in particular a furanyl group, such as a substituted or unsubstituted furanyl group, in particular a 5-methylfuran-2-yl group.

In another particular embodiment, R'2 is hydrogen atom.

In another particular embodiment, R2 is a (C1-C6)alkyl group, a (C3-C14)cycloalkyl group, an aryl group or a heteroaryl group, and R'2 is a hydrogen atom. In another embodiment, R2 is a heteroaryl group, in particular a furanyl group, such as a substituted or unsubstituted furanyl group, in particular a 5-methylfuran-2-yl group, and R'2 is a hydrogen atom.

In a particular embodiment, X6 and X7 are both nitrogen atoms. In another embodiment, X6 is a nitrogen atom and X7 is a CH group. In another embodiment, X6 is a CH group and X7 is a nitrogen atom. In a preferred embodiment, X6 and X7 are nitrogen atoms or X6 is a nitrogen atom and X7 is a CH group. In a most preferred embodiment, X6 is a nitrogen atom and X7 is a CH group.

In a particular embodiment, the cycle

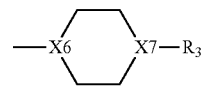

is a substituent of X1, X2 or X3, in particular of X3 (i.e. in para position of the L group) or of X2 (i.e. in meta position of the L group).

In another embodiment, X4 is a CH group or a nitrogen atom.

In another embodiment, X5 is a CH group.

In a particular embodiment, R4 a hydrogen atom, a (C1-C6)alkyl group or a halogen atom. In a further particular embodiment, R4 is a hydrogen atom.

In a particular embodiment, R3 is a hydrogen atom, a carbonyl(C1-C6)alkyl group, a SO2R' group, or a COOR' group.

In a particular embodiment, R' is a methyl or ethyl group, in particular a methyl group. In a particular embodiment, R3 represents a COCH3, a COOCH3 or a SO2CH3 group In a particular embodiment, L1 is a NR7-CO—CH2, NR7-CO—C(CH3)2, CO—NH—CH2, or CO—NH—C(CH3)2 group and L2 is a bond. In a further particular embodiment, L1 is a NR7-CO—CH2 group. In another particular embodiment, R7 is a hydrogen atom. In a further particular embodiment, L1 is a —NH—CO—CH2 group and L2 is a bond.

In a further particular embodiment, the invention relates to a compound of formula (I) wherein:

R1a is a hydrogen atom, a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, a piperidinyl group, a pyrrolidinyl group, or an azepanyl group, wherein said piperidinyl, pyrrolidinyl or azepanyl group can be optionally substituted by at least one (C1-C6)alkyl group;

R1b is a hydrogen atom;

R1c is a (C1-C6)alkyl group; and

R2 is a (C1-C6)alkyl group, a (C3-C14)cycloalkyl group, an (C6-C14)aryl group, or a heteroaryl group, and R'2 is a hydrogen atom.

In a particular embodiment, the invention relates to a compound of formula (I), in which:

R1a is a (C1-C6)alkyl group (such as a methyl or ethyl group, in particular a methyl group) or a heterocyclic group (in particular a piperidinyl group (such as a piperidin-1-yl group));

R1b is a hydrogen atom;

R1c is a (C1-C6)alkyl group (such as a methyl or ethyl group, in particular a methyl group);

R1d and R1e are hydrogen atoms;

R2 is a heterocyclic group (such as a substituted or unsubstituted furanyl group, in particular a 5-methylfuranyl group, more particularly a 5-methylfuran-2-yl group);

L1 represents a NH—CO—CH2 group; R4 is a hydrogen atom;

the cycle

is a substituent of X1, X2 or X3, in particular of X3 (in para position of the L group);

X6 is a nitrogen atom and X7 is a CH group; and

R3 represents a hydrogen atom, a carbonyl(C1-C6)alkyl group (in particular a carbonylmethyl group), a SO2R' group, or a COOR' group, wherein R is in particular a methyl or ethyl group, more particularly a methyl group.

In a particular embodiment, the invention relates to a compound of formula (I), in which:

R1a is a heterocyclic group (in particular a piperidinyl group (such as a piperidin-1-yl group));

R1c is a (C1-C6)alkyl group (such as a methyl or ethyl group, in particular a methyl group);

R2 is a heterocyclic group (such as a substituted or unsubstituted furanyl group, in particular a 5-methylfuranyl group, more particularly a 5-methylfuran-2-yl group);

L1 represents a NH—CO—CH2 group;

L2 is a bond;

R4 is a hydrogen atom;

the cycle

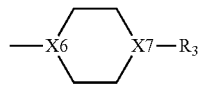

is a substituent of X1, X2 or X3, in particular of X3 (in para position of the L group);

X6 is a nitrogen atom and X7 is a CH group; and

R3 represents a hydrogen atom, a carbonyl(C1-C6)alkyl group (in particular a carbonylmethyl group), a SO2R' group, or a COOR' group, wherein R is in particular a methyl or ethyl group, more particularly a methyl group.

In a particular embodiment, the invention relates to a compound of formula (I), in which:

R1a is a heterocyclic group (in particular a piperidinyl group (such as a piperidin-1-yl group));

R1c is a (C1-C6)alkyl group (such as a methyl or ethyl group, in particular a methyl group);

R2 is a heterocyclic group (such as a substituted or unsubstituted furanyl group, in particular a 5-methylfuranyl group, more particularly a 5-methylfuran-2-yl group);

L1 represents a NH—CO—CH2 group;

L2 is a bound;

R4 is a hydrogen atom;

the cycle

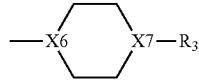

is a substituent of X3 (in para position of the L group);

X6 and X7 are both nitrogen atoms; and

R3 represents a hydrogen atom, a carbonylalkyl group (in particular a carbonylmethyl group), a SO2R' group, or a COOR' group, wherein R' is in particular a methyl or ethyl group, more particularly a methyl group.

In a particular embodiment, R3 represents a COCH3, a COOCH3 or a SO2CH3 group.

In a particular embodiment, the invention relates to a compound of formula (I), in which:

R1a is a (C1-C6)alkyl group (such as a methyl or ethyl group, in particular a methyl group) or a heterocyclic group (in particular a piperidinyl group (such as a piperidin-1-yl group));

R1b is a hydrogen atom;

R1c is a (C1-C6)alkyl group (such as a methyl or ethyl group, in particular a methyl group);

R1d and R1e are hydrogen atoms;

R2 is a heterocyclic group (such as a substituted or unsubstituted furanyl group, in particular a 5-methylfuranyl group, more particularly a 5-methylfuran-2-yl group);

L1 represents a NR7-CO— group;

R7 is a hydrogen;

L2 represents a CR8R'8 group (such as a cyclopropyl group of formula (III)

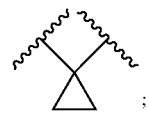

(III)

R4 is a hydrogen atom;

the cycle

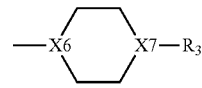

is a substituent of X1, X2 or X3, in particular of X3 (in para position of the L group);

X6 is a nitrogen atom and X7 is a CH group; and

R3 represents a hydrogen atom, a carbonyl(C1-C6)alkyl group (in particular a carbonylmethyl group), a SO2R' group, or a COOR' group, wherein R is in particular a methyl or ethyl group, more particularly a methyl group.

In a particular embodiment:

R1a is a piperidinyl group, such as a piperidin-1-yl group;

R1b, R1d, R1e, R'2 and R4 are hydrogen atom;

R1c is a methyl group;

R2 is a furanyl group, such as a furan-3-yl group, optionally substituted by a methyl group, such as a methylfuranyl group, in particular a methylfuran-2-yl, more particularly a 5-methylfuran2-yl group;

L1 is a NH—CO group;

L2 is a CH2 group or a

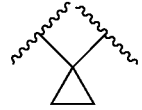 [SMILES: *C1(*)CC1]

group;

the cycle

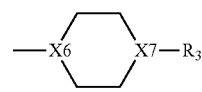

is a substituent of X2 or X3; X5 is a CH group;

X6 is a nitrogen atom;

X7 is a nitrogen atom or a CH group;

R3 is a hydrogen atom or a COCH3, SO2CH3 or COOH group.

In a particular embodiment:
R1a is a piperidinyl group, such as a piperidin-1-yl group;
R1b, R1d, R1e, R'2 and R4 are hydrogen atom;
R1c is a methyl group;
R2 is a furanyl group, such as a furan-3-yl group, optionally substituted by a methyl group, such as a methylfuranyl group, in particular a methylfuran-2-yl, more particularly a 5-methylfuran2-yl group;
L1 is a NH—CO group;
L2 is a CH2 group or a

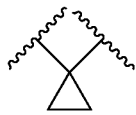

group;
the cycle

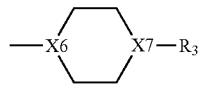

is a substituent of X2 or X3; X5 is a CH group;
X6 is a nitrogen atom;
X7 is a nitrogen atom or a CH group;
R3 is a COCH3 or SO2CH3 group.

The term "alkyl" refers to a saturated hydrocarbon radical that is linear or branched, substituted or not, having preferably from one to six, and even more preferably from one to four carbon atoms, such as methyl, ethyl, n-propyl, isopropyl, n-butyl, isobutyl, tert-butyl, or sec-butyl. The alkyl group can be optionally substituted by one or more halogen atoms, by an (C6-C14)aryl group or by a (C3-C14)cycloalkyl group. Further possible substituents of an alkyl group also include one or more substituents selected from a —NH$_2$ group, a (C1-C6)alkylamino group, a (C1-C6)dialkylamino group, and a (C2-C6)alkynyl group.

The term alkynyl denotes linear or branched hydrocarbon groups containing from 2 to 6 carbon atoms and containing at least one triple bond. Examples of alkynyl containing from 3 to 6 carbon atoms are 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the isomeric forms thereof.

The terms "alkyloxy" and "alkylthio" refer to an alkyl group as defined above that is linked to the remainder of the compound by an oxygen or sulfur atom, respectively.

The term "(C1-C6)alkylamino" refers to a —NH—(C1-C6)alkyl group. In a particular embodiment, the alkyl group of the alkylamino group may be substituted or not with a (C3-C14)cycloalkyl group, a (C6-C14)aryl group, a heterocyclic group, or an (C1-C6)alkyloxycarbonyl group.

The term "(C1-C6)dialkylamino" refers to a —NRR' group where R and R independently represent a (C1-C6) alkyl group as defined above. In a particular embodiment, the alkyl groups of the dialkylamino group may independently be substituted or not with a (C3-C14)cycloalkyl group, a (C6-C14)aryl group, a heterocyclic group, or a (C1-C6)alkyloxycarbonyl group.

The term "cycloalkyl" designates a substituted or unsubstituted alkyl group that forms one cycle having preferably from three to fourteen carbon atoms, and more preferably five to six carbon atoms, such as cyclopropyl, cyclopentyl and cyclohexyl. The cycloalkyl group of the present invention may be unsubstituted, or substituted, for example with a (C1-C6)alkyl group, in particular with a (C1-C6)alkyl group substituted with one or more halogen atoms, such as the CF3 group.

The term "cycloalkylamino" refers to a —NH—(C3-C14)cycloalkyl group or a —N((C1-C6)alkyl)(C3-C14)cycloalkyl group.

The term "amino group" designates a —NH$_2$ group.
The term "hydroxyl group" refers to a —OH group.
The term "carbonyl" designates a CO group.
The term "carbonyl(C1-C6)alkyl" designates a CO—(C1-C6)alkyl group.
The term "amido" designates a CO—NH2 group.
The term "alkylamido" designates a CO—NH—(C1-C6)alkyl group.
The term "(C1-C6)dialkylamido" designates a CO—NRR' group, R and R' representing a (C1-C6)alkyl group as defined above.

A sulfone group designates a SO2 group;
The term "aryl" designates an aromatic group, substituted or not, having preferably from six to fourteen carbon atoms such as phenyl, a-naphtyl, b-naphtyl, or biphenyl.

The term "heterocyclic" refers to a heterocycloalkyl group or a heteroaryl group. The term "heterocycloalkyl" group refers to a cycloalkyl as indicated above that further comprises one or several heteroatoms selected among nitrogen, oxygen or sulfur. They generally comprise from four to fourteen carbon atoms, such as morpholinyl, piperazinyl, piperidinyl, pyrrolidinyl, tetrahydropyranyl, dithiolanyl and azepanyl groups. In a particular embodiment, the heterocycloalkyl group is a 5-, 6- or 7-membered cycle. The term "heteroaryl" refers to an aryl group as indicated above, substituted or not, that further comprises one or several heteroatoms selected among nitrogen, oxygen or sulfur. They generally comprise from four to fourteen carbon atoms. In a particular embodiment, the heteroaryl group is a 5-, 6- or 10-membered heteroaryl group. Representative heteroaryl groups include a pyridinyl, pyrimidinyl, furanyl, thiophenyl, quinoleinyl, and isoquinoleinyl group.

The aryl group or the heterocyclic group can be optionally substituted by one or more halogen atom(s), (C1-C6)alkyl group(s), or (C1-C6)alkyloxy group(s).

By halogen atom, an atom of bromine, chlorine, fluorine or iodine is understood, in particular an atom of bromine, chlorine or fluorine.

Specific compounds according to the invention include:
Cpd.1 2-[6-(4-methanesulfonylpiperazin-1-yl)pyridin-3-yl]-N-{[4-methyl-2-(piperidin-1-yl)phenyl](5-methylfuran-2-yl)methyl}acetamide;
Cpd.2 2-[6-(4-methanesulfonylpiperidin-1-yl)pyridin-3-yl]-N-{[4-methyl-2-(piperidin-1-yl)phenyl](5-methylfuran-2-yl)methyl}acetamide;
Cpd.3 tert-butyl 4-{5-[({[4-methyl-2-(piperidin-1-yl)phenyl](5-methylfuran-2-yl)methyl}carbamoyl)methyl]pyridin-2-yl}piperazine-1-carboxylate;
Cpd.4 2-[2-(4-methanesulfonylpiperazin-1-yl)pyrimidin-5-yl]-N-{[4-methyl-2-(piperidin-1-yl)phenyl](5-methylfuran-2-yl)methyl}acetamide;
Cpd.5 2-[2-(4-methanesulfonylpiperidin-1-yl)pyrimidin-5-yl]-N-{[4-methyl-2-(piperidin-1-yl)phenyl](5-methylfuran-2-yl)methyl}acetamide;
Cpd.6 2-[2-(4-acetylpiperidin-1-yl)pyrimidin-5-yl]-N-[(2,4-dimethylphenyl)(5-methylfuran-2-yl)methyl]acetamide;
Cpd.7 methyl 1-{5-[({[4-methyl-2-(piperidin-1-yl)phenyl](5-methylfuran-2-yl)methyl}carbamoyl)methyl]pyrimidin-2-yl}piperidine-4-carboxylate;

Cpd.8 2-[2-(4-acetylpiperidin-1-yl)pyrimidin-5-yl]-N-{[4-methyl-2-(piperidin-1-yl)phenyl](5-methylfuran-2-yl)methyl}acetamide;

Cpd.9 1-{5-[({[4-methyl-2-(piperidin-1-yl)phenyl](5-methylfuran-2-yl)methyl}carbamoyl)methyl]pyrimidin-2-yl}piperidine-4-carboxylic acid;

Cpd.10 N-{[4-methyl-2-(piperidin-1-yl)phenyl](5-methylfuran-2-yl)methyl}-2-[6-(piperazin-1-yl)pyridin-3-yl]acetamide;

Cpd.11 1-[2-(4-acetylpiperazin-1-yl)pyrimidin-5-yl]-N-{[4-methyl-2-(piperidin-1-yl)phenyl](5-methylfuran-2-yl)methyl}cyclopropane-1-carboxamide;

Cpd.12 2-[6-(4-acetylpiperazin-1-yl)pyridin-2-yl]-N-{[4-methyl-2-(piperidin-1-yl)phenyl](5-methylfuran-2-yl)methyl}acetamide;

Cpd.13 2-[2-(4-acetylpiperazin-1-yl)pyrimidin-5-yl]-N-{[4-methyl-2-(piperidin-1-yl)phenyl](5-methylfuran-2-yl)methyl}acetamide;

Cpd.14 2-[5-(4-acetylpiperazin-1-yl)pyridin-3-yl]-N-{[4-methyl-2-(piperidin-1-yl)phenyl](5-methylfuran-2-yl)methyl}acetamide;

Cpd.15 2-[2-(4-acetylpiperazin-1-yl)pyrimidin-4-yl]-N-{[4-methyl-2-(piperidin-1-yl)phenyl](5-methylfuran-2-yl)methyl}acetamide;

Cpd.16 N-{[4-methyl-2-(piperidin-1-yl)phenyl](5-methylfuran-2-yl)methyl}-2-{6-[4-(trifluoroacetyl)piperazin-1-yl]pyridin-2-yl}acetamide; and Cpd.17 2-[2-(3-methanesulfonylpiperidin-1-yl)pyrimidin-5-yl]-N-{[4-methyl-2-(piperidin-1-yl)phenyl](5-methylfuran-2-yl)methyl}acetamide.

In the present invention, the terms "RORgamma", "RORγ" and "RORg" are used interchangeably.

"RORγ modulator" refers to a chemical compound that modulates, either directly or indirectly, the activity of RORγ. In particular, the RORγ modulator modulates, in particular inhibits or activates, more particularly inhibits, either directly or indirectly, the activity of RORγ. RORγ modulators include antagonists, inverse agonists and agonists of RORγ, in particular antagonists and inverse agonists.

RORgamma modulators can be used as medicinal products. Consequently, the present invention provides a compound of formula (I) for use as a medicament.

The present invention further provides a pharmaceutical composition comprising a compound of formula (I) and a pharmaceutically acceptable carrier. A compound of formula (I), optionally in combination with one or more other therapeutically active substances, may be used in methods for treating diseases for which the modulation of RORgamma has positive effects in a subject in need thereof.

The present invention further provides a compound of formula (I) for use in the treatment of a RORγ related-disease. The invention also provides a method for treating a RORγ related-disease comprising the administration of a therapeutically effective amount of a compound of formula (I) to a subject in need thereof. The invention further provides the use of a compound of formula (I), in the manufacture of a medicament for use in the treatment of a RORγ related-disease.

The compounds of the invention may in particular be used in the treatment of a RORγ related-disease such as an autoimmune or autoimmune-related disease, inflammation-related disease, metabolic disease and/or fibrotic disease, cholestatic, cholestasis-related disease or a cancer. In a particular embodiment, the compound of formula (I) is used in the treatment of an autoimmune or autoimmune-related disease, an inflammation-related disease, a metabolic disease, a fibrotic disease, a cholestatic disease or a cholestasis-related disease.

The term "autoimmune disease" is used to designate a condition that arises from an abnormal immune response of the body against substances and tissues normally present in the body. The disease may be restricted to certain organs (e.g. pancreas, in type I diabetes or thyroid gland in autoimmune thyroiditis) or involve a particular tissue in different places (e.g. in Goodpasture's disease, affection of the basement membrane in the lung and the kidney).

The term "inflammation" is used to designate a condition that arise from a protective response involving host cells, blood vessels, and proteins and other mediators which may serve to eliminate the cause of cell/tissue injury, as well as the necrotic cells/tissues resulting from the original insult, and to initiate the process of repair. The inflammatory reaction may be manifested by pain, heat, redness, swelling, blood vessels dilatation, blood flow increase and loss of function.

Fibrosis is a pathologic process, which includes scar formation and over production of extracellular matrix, by the connective tissue, as a response to tissue damage. Damage to tissue can result from a variety of stimuli including autoimmune reactions and mechanical injury. This can be a reactive, benign, or pathological state that occurs in an organ or tissue. In response to injury this is called scarring and if fibrosis arises from a single cell line this is called a fibroma. Physiologically the deposit of connective tissue can obliterate the architecture and function of the underlying organ or tissue.

Cholestasis is defined as a decrease in bile flow due to impaired secretion by hepatocytes (hepato-cellular cholestasis) or to obstruction of bile flow through intra- or extra-hepatic bile ducts (obstructive cholestasis). In clinical practice, cholestasis is any condition in which the flow of bile from the liver is slowed or blocked.

Cancers are a large family of diseases that involve abnormal cell growth with the potential to invade or spread to other parts of the body. IL-17, which is produced by several types of cells, including immune cells, where IL-17 expression relies on RORgt, is known to contribute to malignant transformation and metastasis of several cancers.

Examples of autoimmune diseases, autoimmune-related diseases, inflammatory diseases, metabolic diseases, fibrotic diseases, cholestatic diseases and cancers include arthritis, asthma, severe, glucocorticoid-nonresponsive asthma, asthma exacerbations due to ongoing and/or past pulmonary infection, Addison's disease, allergy, agammaglobulinemia, alopecia areata, ankylosing spondylitis, atherosclerosis, atopic allergy, atopic dermatitis, autoimmune cardiomyopathy, autoimmune enteropathy, autoimmune hemolytic anemia, autoimmune hepatitis, autoimmune lymphoproliferative syndrome, autoimmune pancreatitis, autoimmune peripheral neuropathy, Crohn's disease, Celiac disease, colitis, chronic inflammatory demyelinating polyneuropathy, chronic obstructive pulmonary disease (COPD), dermatomyositis, diabetes mellitus type 1, diffuse cutaneous systemic sclerosis, eczema, gastrointestinal disorder, Goodpasture's syndrome, Graves' disease, Guillain-Barre syndrome, Hashimoto's encephalopathy, Hashimoto's thyroiditis, idiopathic thrombocytopenic purpura, inflammatory bowel disease (IBD), irritable bowel syndrome, lupus, lupus erythematosus, lupus nephritis, mixed connective tissue disease, Kawasaki disease, multiple sclerosis, neuromyelitis optica, myasthenia gravis, narcolepsy, optic neuritis, osteoarthritis, pemphigus vulgaris, pernicious anaemia, polymyositis, psoriasis, psoriatic arthritis, reactive arthritis, relapsing polychondritis, respiratory disorder, rheumatoid arthritis, rheumatic fever, Sjorgen's syndrome, systemic lupus erythematosus, transverse myelitis, undifferentiated connective tissue disease, ulcerative colitis, uveitis, vasculitis, Wegener's granulomatosis, systemic inflammatory response syndrome (SIRS), sepsis, Behcets disease, allergic contact dermatitis, cutaneous lupus erythematosus, dry eye and glomerulonephritis, myocarditis, acute liver failure (ALF), including acute-on-chronic liver failure (ACLF), pulmonary fibrosis (idiopathic pulmonary, interstitial lung, cystic and progressive massive fibrosis), liver fibrosis and cirrhosis of diverse etiologies (congenital, of autoimmune origin, induced by cardiometabolic diseases, alcohol consumption, cholestasis, drugs, infectious agents, trauma, radiation), metabolic syndrome, non-alcoholic fatty liver disease (NAFLD), NonAlcoholic SteatoHepatitis (NASH) and Alcoholic SteatoHepatitis (ASH), cardiac fibrosis and heart myocardial and endomyocardial fibrosis, arterial fibrosis, atherosclerosis/restenosis, mediastinal fibrosis (soft tissue of the mediastinum), macular degeneration, retinal and vitreal retinopathy, ocular scarring, cataract, Alzheimer's disease, cancer, local, disseminated or metastatic cancer, scleroderma, glioblastoma, myelofibrosis (bone marrow), retroperitoneal fibrosis (soft tissue of the retroperitoneum), nephrogenic systemic fibrosis (skin, joints, eyes, and internal organs), keloid (skin), intestinal fibrosis (occurs for example in Crohn's disease and collagenous colitis), kidney fibrosis, scleroderma and systemic sclerosis (skin, lungs, kidneys, heart, and gastrointestinal tract), arthrofibrosis (knee, shoulder, other joints), Peyronie's disease (penis), Dupuytren's contracture (hands and fingers), some forms of adhesive capsulitis (shoulder), obesity, Primary Biliary Cholangitis (PBC), Primary Sclerosing Cholangitis (PSC), Intarhepatic Cholestasis of Pregnancy (ICP), Progressive Familial Intrahepatic Cholestasis (PFIC), Biliary atresia, Cholelithiasis, Infectious cholangitis, Cholangitis associated with Langerhans cell histiocytosis, Alagille syndrome, Nonsyndromic ductal paucity, Hepatitis (hepatitis A, hepatitis B, hepatitis C), Alpha1-antitrypsin deficiency, Inborn errors of bile acid synthesis, Drug-induced cholestasis, Total parenteral nutrition (TPN)—associated cholestasis, breast cancer and breast cancer metastasis, pancreatic cancer and pancreatic cancer metastasis, pancreatic ductal adenocarcinoma, liver cancer and liver cancer metastasis, hepatocellular carcinoma, lung cancer and lung cancer metastasis, non-small-cell lung cancer, colorectal cancer and colorectal cancer metastasis, colorectal carcinoma, prostate cancer and prostate cancer metastasis, gallbladder cancer and gallbladder cancer metastasis.

In particular, RORg modulators may be used in the treatment of asthma, ankylosing spondylitis, autoimmune cardiomyopathy, autoimmune hepatitis, crohn's disease, chronic obstructive proliferative disease (COPD), diabetes mellitus type 1, lupus erythematosus, lupus nephritis, multiple sclerosis, psoriasis, psoriatic arthritis, rheumatoid arthritis, ulcerative colitis, myocarditis, pulmonary fibrosis (idiopathic pulmonary, interstitial lung, cystic and progressive massive fibrosis), non-alcoholic fatty liver disease (NAFLD), non-alcoholic steato-hepatitis (NASH) and alcoholic steatoHepatitis (ASH), cardiac fibrosis and heart myocardial and endomyocardial fibrosis, arterial fibrosis, atherosclerosis/restenosis, intestinal fibrosis (occurs for example in crohn's disease and collagenous colitis), kidney fibrosis, scleroderma, systemic sclerosis, primary biliary cholangitis (PBC), hepatitis (hepatitis A, hepatitis B, hepatitis C), colon cancer, small-cell lung cancer, non-small cell lung cancer, prostate cancer, renal cancer, ovarian cancer, bladder cancer, stomach cancer, liver cancer, testis cancer, uterus cancer, leukemia, adenocarcinoma, melanoma and cancer of central nervous system tissue.

The term "treatment" or "treating" refers to therapy, prevention, or prophylaxis of a disorder in a subject in need thereof. The treatment involves the administration of a pharmaceutical composition to subjects (e.g. patients) having a declared disorder to prevent, cure, delay, reverse, or slow down the progression of the disorder, improving thereby the condition of patients. A treatment may also be administered to subjects that are either healthy or at risk of developing a disorder such as an autoimmune, inflammatory, fibrotic or cholestatic disorder.

The term "subject" refers to a mammal and more particularly a human. The subjects to be treated according to the invention can be appropriately selected on the basis of several criteria associated with autoimmune, inflammatory, fibrotic and cholestatic pathological processes such as previous and/or present drug treatments, associated pathologies, genotype, exposure to risk factors, as well as any other relevant biomarker that can be evaluated by means of any suitable immunological, biochemical, or enzymatic method.

The Examples show how Compounds of formula (I) can be produced and tested.

The details of the general methods of synthesis and purification of intermediate products for Compounds of formula (I) are provided in Example 1.

Specific reaction intermediates can be synthesized and purified from compounds that may be already available commercially or that can be readily synthesized.

The details of the general methods of synthesis and purification of Compounds of formula (I) are provided in Example 2.

General schemes of synthesis of the compounds of formula (I) are presented in FIG. 3.

The functional groups optionally present in the reaction intermediates that are generated for obtaining the desired compounds of formula (I) can be protected, either permanently, or temporarily, by protective groups, which ensure unequivocal synthesis of the desired compounds. The reactions of protection and deprotection are carried out according to techniques well known by a person skilled in the art or such as those described in the literature, as in the book "Greene's Protective Groups in Organic Synthesis" (Wuts & Greene, 2007).

The compounds according to the invention may contain one or more asymmetric centers. The present invention includes stereoisomers (diastereoisomers, enantiomers), pure or mixed, as well as racemic mixtures and geometric isomers, or tautomers of compounds of formula (I). When an enantiomerically pure (or enriched) mixture is desired, it can be obtained either by purification of the final product or of chiral intermediates, or by asymmetric synthesis according to methods known by a person skilled in the art (using for example chiral reactants and catalysts). Certain compounds according to the invention can have various stable tautomeric forms and all these forms and mixtures thereof are included in the invention. The techniques for obtaining and characterizing the stereoisomers, pure or mixed, as well as racemic mixtures and geometric isomers, or tautomers are described in the literature, such as in the book "Chirality in Drug Design and Development" (Reddy & Mehvar, 2004).

The compounds of formula (I) can be purified by precipitation or solid/liquid extraction after evaporation of the reaction medium. Further or other purification step can be performed by chromatography over silica gel or by crystallization, when the compound is stable as a solid form, by applying techniques well known in the literature or, more in general, for chemicals (Armarego & Chai, 2009).

Moreover, the required purification and/or (re-)crystallization steps that are appropriate for isolating compounds of formula (I) from the reaction mixture, can be used for obtaining amorphous, polymorphous, mono- or poly-crystalline forms. Such polymorphisms may present distinct pharmacological and/or chemical properties, for example in terms of solubility, intrinsic dissolution rate, melting temperature, bioavailability, and/or possible transition from a polymorphic state to another one in pharmaceutical compositions and/or biological fluids.

The (re-)crystallisation assays can be performed in panels of different solvents (such as isopropanol, acetone, methanol, diisopropyl ether or water) or mixture thereof, and by applying different conditions, such as reaction volumes or temperatures. The resulting samples can be analyzed by different techniques such as microscopy, calorimetry, and/or spectroscopy that allow establishing the features of a particular crystalline form, such as structure, solubility, stability or conversion to other forms (Bauer, 2004; Erdemir et al, 2007; Morissette et al, 2004; Yin & Grosso, 2008).

Such a polymorphism study allows characterizing the crystalline form of a compound that is pharmaceutically acceptable for both pharmacological and manufacturing points of view.

Certain compounds of formula (I) can be isolated in the form of zwitterions and each of these forms is included in the invention, as well as mixtures thereof.

Compounds of formula (I) and their salts can be stable in liquid or solid forms. The present invention includes all solid and liquid forms of formula (I), which includes the amorphous, polymorphic, mono- and poly-crystalline forms. In particular, the compounds of formula (I) can exist in the free form or in the solvated form, i.e. in the form of associations or combinations with one or more molecules of a solvent, for example with pharmaceutically acceptable solvents such as water (hydrates) or ethanol. The present invention also includes the prodrugs of the compounds according to the invention which, after administration to a subject, are converted to the compounds as described in the invention or to their metabolites having therapeutic activities comparable to the compounds according to the invention.

Specific compounds of formula (I) can comprise at least one atom of the structure that is replaced by an isotope (radioactive or not). Examples of isotopes that can be included in the structure of the compounds according to the invention can be selected from hydrogen, carbon, nitrogen, oxygen, sulphur such as $^{2}H$, $^{3}H$, $^{13}C$, $^{14}C$, $^{15}N$, $^{18}O$, $^{17}O$, $^{35}S$ respectively. When non-radioactive, the stable isotope can be selectively incorporated in the structure in place of hydrogen (in the case of deuterium) or carbon (in the case of $^{13}C$) not only as means of performing absorption, distribution, metabolism, and excretion (ADME) studies but also as means for obtaining compounds that may retain the desired biochemical potency and selectivity of the original compound while the metabolic fate is substantially altered. In some favourable cases, this modification has the potential to have a positive impact effect on safety, efficacy and/or tolerability of the original compound (Mutlib, 2008). Otherwise radioactive isotopes $^{3}H$ and $^{14}C$ are particularly preferred as they are easy to prepare and detect in studies of the bioavailability in vivo of the substances. The heavy isotopes (such as $^{2}H$) are particularly preferred as they are used as internal standards in analytical studies and as possible variants of pharmaceutical interest.

Compounds of formula (I) can be obtained as specific salts, hydrates, and polymorphs that can be obtained during the final purification step of the compound or, in the case of salts, by incorporating the salt into the previously purified compound. The selection of a compound of formula (I) that is produced according to the methods of the Invention as an optimal candidate for drug development can be automated for a comprehensive biopharmaceutical characterization at the scale-up stage and for the solid or liquid formulation that is appropriate for the desired route of administration and therapeutic indication (Kumar et al, 2007; Mahato & Narang, 2011; Stahl & Wermuth, 2002).

In view of their use as medicinal products, the compounds of formula (I) can be formulated as pharmaceutically acceptable salts obtained from organic or inorganic bases or acids of such compounds. Alternatively, the compounds of formula (I) can be formulated as pharmaceutically acceptable hydrates or polymorphs of such compounds. These salts, hydrates, and polymorphs can be obtained during the final purification step of the compound or, in the case of salts, by incorporating the salt into the previously purified compound (Stahl & Wermuth, 2002).

These salts can be prepared with pharmaceutically acceptable acids but the salts of other acids useful for purifying or isolating the compounds of formula (I) also form part of the invention. In particular, when the compounds according to the invention are in the form of a salt, it is a salt of an alkali metal, in particular a salt of sodium or of potassium, or a salt of an alkaline-earth metal, in particular magnesium or calcium, or a salt with an organic amine, more particularly with an amino acid such as arginine or lysine.

The present invention further provides pharmaceutical compositions comprising a compound of formula (I), or a pharmaceutically acceptable salt thereof, and optionally at least one pharmaceutically acceptable carrier or diluent. The pharmaceutical compositions comprising a compound of formula (I) may comprise one or several excipients or vehicles acceptable within a pharmaceutical context (e.g., for liquid formulations, saline solutions, physiological solutions, isotonic solutions).

A further object of the invention are methods of preparing such pharmaceutical compositions, comprising admixing a compound of formula (I), with at least one pharmaceutically acceptable carrier, vehicle, or diluent. These methods involve, for example, conventional mixing, dissolving, granulation, dragee-making, levigating, emulsifying, encapsulating, entrapping, lyophilizing processes or spray drying (Gennaro, 2000; Rowe et al, 2003).

The phrase "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

The term "carrier", "vehicle", or "excipient" refers to any substance, not itself a therapeutic agent, that is added to a pharmaceutical composition to be used as a carrier, vehicle, and/or diluent for the delivery of a therapeutic agent to a subject in order to improve its handling or storage properties or to permit or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, polysorbate 80, mannitol, gelatin, lactose, vegetable oils, liposomes, etc. Acceptable excipients can be chosen among disintegrants, binding agents, adhesives, wetting agents, lubricants, glidants, flavors, dyes, fragrances, stearic acid, magnesium oxide, sodium and calcium salts of phosphoric and sulfuric acids, magnesium carbonate, talc, gelatin, lactose, sucrose, starches, polymers, such as polyvinyl alcohol and polyethylene glycols, and other pharmaceutically acceptable materials added to improve taste, odor or appearance of the composition.

The compounds can be made up in solid or liquid form, such as tablets, capsules, powders, syrups, elixirs and the like, aerosols, sterile solutions, suspensions or emulsions, and the like. The composition may be presented in a solid preformulation composition wherein the active ingredients are dispersed evenly throughout the composition so that the composition may be readily subdivided into equally effective dosage forms such as tablets, pills and capsules. Additionally, the combined compositions may be delivered using sustained-release formulations.

The compositions can be formulated as injectable suspensions, gels, oils, pills, suppositories, powders, gel caps, capsules, aerosols, etc., eventually by means of galenic forms or devices assuring a prolonged and/or slow release. For this kind of formulation, agents such as cellulose, carbonates or starches can advantageously be used. The compositions of the present invention can also be formulated in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phophatidylcholines, cardiolipins, phosphatidylethanolamines, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof.

The pharmaceutical combination of the invention can be administered in a systematic or parenteral way, by using oral, topical, perlingual, nasal, rectal, transmucosal, transdermal, intestinal, intramuscular, intravenously, subcutaneous, intraarterial, intraperitoneal, intrapulmonary or intraocular route, by using methods known in the art.

Formulations for oral administration may be in the form of aqueous solutions and suspensions, in addition to solid tablets and capsule formulations. The aqueous solutions and suspensions may be prepared from sterile powders or granules. The compounds may be dissolved in water, polyethylene glycol, propylene glycol, ethanol, corn oil, cottonseed oil, peanut oil, sesame oil, benzyl alcohol, sodium chloride, and/or various buffers.

For administration by inhalation, the pharmaceutical compositions comprising a compound of formula (I) are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, 1,1,1,2-tetrafluoroethane, 1,1,1,2,3,3,3-heptafluoropropane, carbon dioxide or other suitable gas, alone or in combination. Pressurized aerosols may be formulated as suspensions or solutions, and include an appropriate propellant formulation, and various excipients, such as surfactants, co-solvents, etc. In the case of a pressurized aerosol the dosage unit may be determined by providing a valve to deliver a metered amount. Capsules and cartridges of e.g. gelatin for use in an inhaler or insufflators may be formulated containing a powder mix of the compound and a suitable powder base such as lactose or starch.

The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of material can be used for such enteric layers or coatings, such materials including a number of polymeric acids with such as shellac and cellulose acetate.

The liquid forms in which the pharmaceutical compositions can be incorporated for oral administration or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methylcellulose and the like. For parenteral administration, sterile suspensions and solutions are desired. A person skilled in the art will take care to select the possible compound or compounds to be added to these compositions in such a way that the advantageous properties intrinsically attaching to the present invention are not or substantially not altered by the addition envisaged, as is also explained in the literature, for example in the book "Pharmaceutical Dosage Forms and Drug Delivery" (2007; edited by Mahato R; published by CRC Press).

A pharmaceutical composition as disclosed herein is understood to be useful for treating a RORγ related-disease, that is, the active ingredients are contained in an amount to achieve their intended purpose. At this scope, a compound of formula (I) should be administered in an effective amount by using a pharmaceutical composition as above-defined. Administration can be performed daily or even several times per day, if necessary, and in an amount that can be optimal or suboptimal, if they are compared with dosages that are normally used for such compounds.

The term "effective amount" refers to an amount of the compound sufficient to produce the desired therapeutic result. In particular the compounds of formula (I) are administered in amounts that are sufficient to display a desired effect.

Optimal dosages of compounds of formula (I) to be administered may be readily determined by those skilled in the art, and will vary with the particular compound used, the strength of the preparation, the mode of administration, and the severity of the condition to be treated. In addition, factors associated with the particular patient being treated, including patient age, weight, diet and time of administration, will result in the need to adjust dosages and interval. The frequency and/or dose relative to the simultaneous or separate administrations can be adapted by one of ordinary skill in the art, in function of the patient, the pathology, the form of administration, etc. For instance, a compound of formula (I) should be provided in a dosage that allows its administration in the amount 0.01 mg/day to 1000 mg/day, preferably from 0.1 mg/day to 10 mg/day.

The compounds of formula (I) can advantageously be formulated and/or administered in combination with one or more other therapeutically active substances, marketed or under development, that are selected according to a specific autoimmune, inflammatory, fibrotic or cholestatic disorder or any other disorders that may be found associated to said disorder in medical settings and that should be also treated. Such a combined administration includes two possibilities: the two agents are administered to a subject at substantially similar times; or the two agents are administered to a subject at different times, at independent intervals that may or may not overlap or coincide. As such, the invention also relates to a kit-of-parts, comprising a compound of the invention, in association with another therapeutically active agent, for their simultaneous, separate or sequential use in the therapy, in particular in the treatment of an autoimmune, inflammatory, fibrotic or cholestatic disorder.

The invention also relates to a pharmaceutical composition comprising a compound of formula (I) and at least one other therapeutically active agent.

A non-exhaustive list of active agents that may be advantageously formulated and/or administered with compounds of formula (I) includes:
  anti-inflammatory;
  anti-oxidant agents;
  immunosuppressor agents;
  agents used in the treatment of asthma;
  agents used in the treatment of psoriasis;
  agents used in the treatment of respiratory diseases;
  hepatoprotective agents;
  agents used in the treatment of heart failure or coronary insufficiency Anti-hypertensive and hypotensive agents;
  anti-coagulant, vasodilators;
  anti-ischemic agents;
  agents used in the treatment of metabolic diseases, such as anti-diabetic, hypolipidemic, hypocholesterolemic, anti-atherosclerotic and anti-obesity agents.
  anti-viral agents;
  anti-cancer agents and cancer prevention agents;
  anti-cholestatic agents;
  anti-fibrotic agents;
  anti-NAFLD agents;
  anti-NASH agents.

In a particular embodiment, the invention relates to the use of a compound of formula (I) in combination with an anti-fibrotic, anti-NAFLD or anti-NASH agent. Therefore, the invention relates to a first combination product comprising:
  a) a RORgamma modulator, such as a compound of formula (I) or a pharmaceutically acceptable salt thereof; and
  b) another therapeutically active agent.

In a particular embodiment, the other therapeutically active agent is an anti-fibrotic, anti-NAFLD or anti-NASH agent. In another particular embodiment, the other therapeutically active agent is a PPAR activator as defined below.

In a particular embodiment, the combination product is a composition comprising the RORgamma modulator and the other therapeutically active agent, and a pharmaceutically acceptable carrier.

In another embodiment, the combination product is a kit of parts comprising components a) and b) of the combination product. The kit of parts of the invention is for sequential, separate or simultaneous use in the treatment of any of the diseases mentioned above.

In another aspect, the invention relates to a combination of a RORγ modulator and a PPAR activator. In a particular embodiment, the invention relates to a composition comprising a RORγ modulator and a PPAR activator. In another embodiment, the invention relates to a kit-of-parts comprising a RORγ modulator and a PPAR activator, for simultanate, separate or sequential use.

The PPARs (α, β/δ (herein after δ), γ) belong to the hormone-activated nuclear receptor family. The PPARs, or "Peroxisome Proliferator Activated Receptors", are nuclear receptors from the superfamily of transcription factors activated by the following ligands: steroids/thyroid hormones/retinoids. To date, three PPAR isotypes have been identified in mice and humans: PPARα, PPARδ and PPARγ. While PPARb/d expression in humans appears to be ubiquitous, PPARα and γ exhibit a differential tissue distribution (Braissant O and Wahli W, 1998). PPARa is expressed in cells with high fatty acid catabolic activity and in cells with high peroxisomal activity (hepatocytes, cardiomyocytes, renal proximal tubules, intestinal mucosa). PPARb/d is expressed ubiquitously and abundantly in most tissues. As far as PPARγ expression is concerned, it is limited mainly to adipose tissue, certain immune system cells and retina and is present in only trace amounts in other organs (Braissant O and Wahli W, 1998).

Taking the example of PPARα, its action is mediated by a class of compounds such as the fibrates which have a lipid-lowering effect. Natural ligands have also been identified such as for example fatty acids, eicosanoids (leukotriene B4) and 8(S)-hydroxyeicosatetraenoic acid (Kliewer S A et al., 1997). The PPARs have been associated primarily with lipid and glucose metabolism. PPAR activators, such as fibrates, enable a regulation of plasma cholesterol and triglyceride concentrations via activation of PPARa (Hourton D et al., 2001). Fibrate therapy leads to an increase in fatty acid oxidation in liver. Fibrates also decrease the synthesis of triglycerides (Staels B and Auwerx J, 1998). PPARa activators are also capable of correcting hyperglycemia and insulin level. Fibrates also reduce adipose tissue mass through a mechanism which is independent of food intake and leptin gene expression (Guerre-Millo M et al., 2000). The therapeutic interest of PPARγ agonists has been widely investigated in the treatment of type 2 diabetes (Spiegelman B M, 1998). It has been shown that PPARγ agonists restore insulin sensitivity in target tissues and reduce plasma glucose, lipid and insulin levels both in animal models of type 2 diabetes and in humans (Ram V J, 2003). PPAR activation by ligands also plays a role in regulating the expression of genes that participate in processes such as inflammation, angiogenesis, cell proliferation and differentiation, apoptosis and the activities of iNOS, MMPase and TIMPs. Activation of PPARα in keratinocytes results in a cessation of their proliferation and expression of genes involved in differentiation (Komuves L G et al., 2000). The PPARs have anti-inflammatory properties because they negatively interfere with transcription mechanisms involving other transcription factors like NF-κB or transcriptional activators like STAT and AP-1 (Desvergne B and Wahli W, 1999). Said anti-inflammatory and anti-proliferative properties make the PPARS (and particularly PPARα) interesting therapeutic targets for the treatment of diseases such as vascular occlusive diseases (atherosclerosis, etc.), hypertension, diseases related to neovascularization (diabetic retinopathy, etc.), inflammatory diseases (inflammatory bowel disease, psoriasis, etc.) and neoplastic diseases (carcinogenesis, etc.).

The combination of the invention may be used as a medicament. In a particular embodiment, the combination is used for the treatment of one of the diseases mentioned above. The RORγ modulator and the PPAR activator are each administered to a subject in need thereof in a therapeutically effective amount.

In a particular embodiment, the ROR modulator in the combination is a compound of formula (I).

In a particular embodiment, the PPAR activator in the combination is a PPARα, PPARδ, PPARγ, PPARα/δ (or dual PPARα/δ), PPARα/γ (or dual PPARα/γ), PPARγ/δ (or dual PPARγ/δ), or PPARα/γ/δ (or pan-PPAR) activator.

In a particular embodiment, the PPAR alpha agonist is a fibrate such as fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate or SR10171.

In a particular embodiment, the PPAR gamma agonist is a glitazone (or thiazolidinedione) such as Rosiglitazone, Pioglitazone, deuterated pioglitazone, efatutazone, ATx08-001, OMS-405, CHS-131, THR-0921, SER-150-DN, KDT-501, GED-0507-34-Levo, CLC-3001 or ALL-4.

In a particular embodiment, the PPAR delta agonist is GW501516 (Endurabol or ({4-[({4-methyl-2-[4-(trifluoromethyl)phenyl]-1,3-thiazol-5-yl}methyl)sulfanyl]-2-methylphenoxy}acetic acid)), MBX8025 (Seladelpar or {2-methyl-4-[5-methyl-2-(4-trifluoromethyl-phenyl)-2H-[1,2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy]acetic acid), L165041, HPP-593 or NCP-1046.

In a particular embodiment, the PPAR alpha/gamma dual agonist is a glitazar such as Saroglitazar, Aleglitazar, Muraglitazar, Tesaglitazar or DSP-8658.

In a particular embodiment, the PPAR alpha/delta dual agonist is Elafibranor (GFT505) or T913659.

In a particular embodiment, the PPAR gamma/delta dual agonist is a conjugated linoleic acid (CLA) or T3D-959.

In a particular embodiment, the PPAR alpha/gamma/delta pan agonist is IVA337, TTA (tetradecylthioacetic acid), Bavachinin, GW4148, GW9135, Bezafibrate, Lobeglitazone or CS038.

In a more particular embodiment, the PPAR activator is a compound of formula (II), or a pharmaceutically acceptable salt thereof:

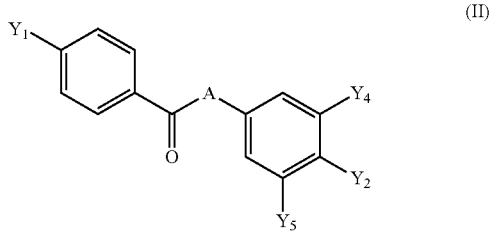

(II)

in which:
Y1 represents a halogen, a Ra, or Ga—Ra group;
A represents a CH=CH or a CH2-CH2 group;
Y2 represents a Gb-Rb group;
Ga and Gb, identical or different, represent an atom of oxygen or sulfur;
Ra represents a hydrogen atom, an unsubstituted (C1-C6) alkyl group, a (C6-C14)aryl group or a (C1-C6)alkyl group that is substituted by one or more halogen atoms, a (C1-C6)alkoxy or a (C1-C6)alkylthio group, (C3-C14)cycloalkyl groups, (C3-C14)cycloalkylthio groups or heterocyclic groups;
Rb represents a (C1-C6)alkyl group substituted by at least a —COORc group, wherein
Rc represents a hydrogen atom, or a (C1-C6)alkyl group that is substituted or not by one or more halogen atoms, (C3-C14)cycloalkyl groups, or heterocyclic groups; and
Y4 and Y5, identical or different, representing a (C1-C6) alkyl group that is substituted or not by one or more halogen atoms, (C3-C14)cycloalkyl groups or heterocyclic groups.

In a particular embodiment of the compound of formula (II):
Y1 represents a halogen, a Ra, or a Ga—Ra group;
A represents a CH=CH group;
Y2 represents a Gb-Rb group;
Ga and Gb, identical or different, represent an atom of oxygen or sulfur;
Ra represents a (C1-C6)alkyl or (C3-C14)cycloalkyl group, in particular a (C1-C7)alkyl or (C3-C14)cycloalkyl group substituted or not by one or more halogen atoms;
Rb represents a (C1-C6)alkyl group substituted by a —COOR3 group, wherein Rc represents a hydrogen atom or an alkyl group having from one to four carbon atoms; and
Y4 and Y5 independently represent a (C1-C4)alkyl group.

In a particular embodiment of the compound of formula (II):
Y1 represents a Ra or Ga—Ra group;
A represents a CH2-CH2 group;
Y2 represents a Gb-Rb group;
Ga represents an atom of oxygen or sulfur and Gb represents an atom of oxygen;
Ra represents a (C1-C6)alkyl or (C3-C7)cycloalkyl group;
Rb represents a (C1-C6)alkyl group substituted by at least a —COORc group, wherein Rc represents a hydrogen atom or (C1-C4)alkyl group; and
Y4 and Y5 independently represent a (C1-C4)alkyl group.

In a particular embodiment of the compound of formula (II):
Y1 represents a halogen atom or a Ra or Ga—Ra group;
A represents a CH2-CH2 group;
Y2 represents a Gb-Rb group;
Ga represents an atom of oxygen or sulfur and Gb represents an atom of oxygen;
Ra represents a (C1-C6)alkyl or (C3-C14)cycloalkyl group that is substituted by one or more halogen atoms;
Rb represents a (C1-C6)alkyl group substituted or not by one or more halogen atoms and substituted by at least a —COORc group, wherein Rc represents a hydrogen atom or a (C1-C4)alkyl group; and
Y4 and Y5 represent a (C1-C4)alkyl group.

In a particular embodiment of the compound of formula (II), Gb is an oxygen atom and Rb is (C1-C6)alkyl group substituted by a —COORc group, wherein Rc represents a hydrogen atom or an unsubstituted linear or branched (C1-C4)alkyl group.

In a particular embodiment of the compound of formula (II), Y1 is a (C1-C6)alkylthio group that comprises a (C1-C6)alkyl group that is linear or branched that is substituted or not by one or more halogen atoms.

In a particular embodiment, the compound of formula (II) is selected in the group consisting of 1-[4-methylthiophenyl]-3-[3,5-dimethyl-4-carboxydimethylmethyloxy phenyl] prop-2-en-1-one (Elafibranor or GFT505), 1-[4-methylthiophenyl]-3-[3,5-dimethyl-4-isopropyloxy carbonyldimethylmethyloxyphenyl]prop-2-en-1-one, 1-[4- methylthiophenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl]prop-2-en-1-one, 1-[4-trifluoromethyloxyphenyl]-3-[3,5-dimethyl-4-carboxydimethylmethyl oxyphenyl]prop-2-en-1-one, 2-[2,6-dimethyl-4-[3-[4-(methylthio)phenyl]-3-oxo-propyl]phenoxy]-2-methylpropanoic acid, and 2-[2,6-dimethyl-4-[3-[4-(methylthio) phenyl]-3-oxo-propyl]phenoxy]-2-methyl-propanoic acid isopropyl ester.

In a more particular embodiment, the PPAR activator is 1-[4-methylthiophenyl]-3-[3,5-dimethyl-4-carboxydimethylmethyloxy phenyl]prop-2-en-1-one (or Elafibranor—GFT505), or a pharmaceutically acceptable salt thereof.

In a particular aspect, the invention relates to a combination product comprising:

i) a RORgamma modulator, in particular a compound of formula (I) or a pharmaceutically acceptable salt thereof;

ii) a PPAR activator, in particular a compound of formula (II) or a pharmaceutically acceptable salt thereof, in particular Elafibranor or a pharmaceutically acceptable salt thereof.

In a particular embodiment, the combination product is a composition comprising:

i) a RORgamma modulator, in particular a compound of formula (I) or a pharmaceutically acceptable salt thereof; and ii) a PPAR activator, in particular a compound of formula (II) or a pharmaceutically acceptable salt thereof, in particular Elafibranor or a pharmaceutically acceptable salt thereof; and iii) a pharmaceutically acceptable carrier.

In a particular embodiment, the combination product is a kit of parts comprising:

i) a RORgamma modulator, in particular a compound of formula (I) or a pharmaceutically acceptable salt thereof; and ii) a PPAR activator, in particular a compound of formula (II) or a pharmaceutically acceptable salt thereof, in particular Elafibranor or a pharmaceutically acceptable salt thereof;

for sequential, separate or simultaneous use in the treatment of any of the diseases mentioned above.

Several other advantages of the invention will rise in the reading of the following examples; they should be considered as illustrative data and not as limitative ones.

EXAMPLES

Chemical names follow IUPAC nomenclature. Starting materials and solvents were purchased from commercial suppliers (Acros Organic, Sigma Aldrich, Combi-Blocks, Fluorochem, Fluka, Alfa Aesar or Lancaster) and were used as received without further purification. Some starting materials can be readily synthesized by a person skilled in the art. Air and moisture sensitive reactions were carried out under an inert atmosphere of nitrogen, and glassware was oven-dried. No attempts were made to optimize reaction yields. Thin-layer chromatography (TLC) was done on Merck silica gel 60 UV254 (250 µm) plates. Visualization was accomplished with UV light. Column chromatography was performed on Geduran silica gel 60 (40-63 µm) from Merck. Melting points (mp) were recorded with a Büchi Melting Point B-545 and are uncorrected. All microwave irradiation experiments were carried out in a Biotage Initiator microwave apparatus. $^1$H spectra were recorded on Bruker Advance I spectrometer at 300 MHz. Chemical shifts ($\delta$) are reported in ppm (parts per million), by reference to the hydrogenated residues of deuterated solvent as internal standard: 2.50 ppm for DMSO-d6, 7.26 ppm for CDCl3, and 3.31, and 4.78 for Methanol-d4. The spectral splitting patterns are designated as follows: s, singlet; d, doublet; dd, doublet of doublets; ddd, doublet of doublet of doublets; t, triplet; dt, doublet of triplets; q, quartet; m, multiplet; br s, broad singlet. Coupling constants (J) are quoted to the nearest 0.1 Hz. All tested compounds exhibited ≥95% chemical purity assessed by HPLC on a Merck HITACHI Lachrom L-7000 series and Merck HITACHI diode array detector L-7455 with a Waters column Symmetry C18 (3.5 µm, 4.6*75 mm) and using a gradient of MeOH/Millipore water containing 0.1% of formic acid. Chromatograms were analyzed with Lachrom software version 890-8800-09. Mass spectrometry measurements were performed on Alliance 2695 and DAD detector 2998 equipped with an Acquity QDa detector from Waters using a Waters column Symmetry C18 (3.5 µm, 4.6*75 mm) and using a gradient of MeOH/Millipore water containing 0.1% of formic acid (chromatograms were analyzed with Empower 3 software) or they were performed on apparatus equipped with Waters 2545 binary gradient module, Waters 2489 UV/Visible detector and Acquity QDa detector using a Waters column Symmetry C18 (3.5 µm, 4.6*75 mm) and using a gradient of MeOH/Millipore water containing 0.1% of formic acid (chromatograms were analyzed with MassLynx 4.1). Preparative HPLC were performed on apparatus equipped with Waters 2545 binary gradient module, Waters 2489 UV/Visible detector, Acquity QDa detector and Waters 2767 sample manager using a Waters column SymmetryPrep C18 (7 µm, 19*150 mm) and using a gradient of MeOH/Millipore water containing 0.1% of formic acid (chromatograms were analyzed with MassLynx 4.1). All solvents are HPLC grade.

The compounds of the invention are prepared according to the general methods and general protocols of synthesis given below. Representative procedures suitable for the preparation of compounds of formula (I) are outlined in the Reaction Schemes for intermediate (FIG. 1A-1L and FIG. 2) and final (FIG. 3) compounds. Reagents and conditions may be adapted and additional steps employed to produce further compounds encompassed in the present invention having alternative substituent groups, or for achieving such compounds at higher yield and/or of higher purity.

Example 1: Synthesis of Intermediates for the Synthesis of Compounds According to the Invention In the following, compounds termed "Ex. X" are intermediate compounds used for the synthesis of compounds of the present invention.

The general treatments and purification steps are carried out according to techniques well known by a person skilled in the art or such as those described in the literature: the reaction was quenched either with water, brine or sat. NH4Cl. Excess or solvent used for the reaction was removed under reduced pressure. The aqueous layer was extracted three times with a non-water miscible solvent (e.g. Et2O, EtOAc, CH2Cl2). The organic layer was dried over MgSO4, filtered and the solution was concentrated under reduced pressure. Purification of the crude material was realized either by double extraction using conc. HCl and NaOH 2N, by hydrochloride formation or by purification on silica gel column chromatography using standard mixture systems (cyclohexane/EtOAc, CH2Cl2/MeOH and CH2Cl2/EtOAc).

Figure 1A:
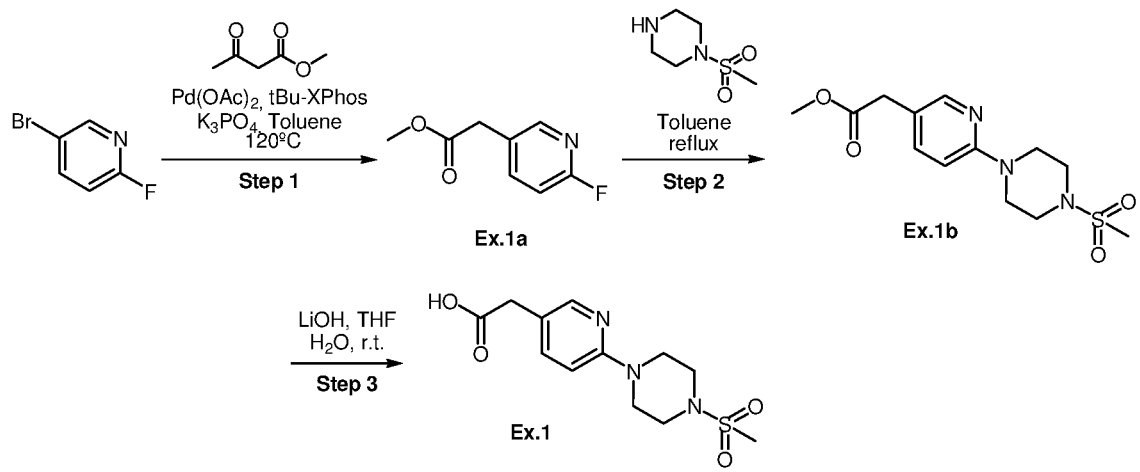

Example 1a: Synthesis of Acid Intermediates for the Synthesis of Compounds According to the Invention Intermediate Ex.1: 2-[6-(4-methanesulfonylpiperazin-1-yl)pyridin-3-yl]acetic acid (FIG. 1A)

TABLE 1.1

| Cpd. | Starting compounds, Reaction conditions and purification, Yield, Appearance, $^1$H NMR (solvent) data |
|---|---|
| Ex. 1a | methyl 2-(6-fluoropyridin-3-yl)acetate<br>Step 1: 5-bromo-2-fluoropyridine (2.9 mL, 28.41 mmol), methyl acetoacetate (9.2 mL, 85.23 mmol) and potassium phosphate (24.12 g, 113.64 mmol) were charged to a flask, toluene (280 mL) was added and the mixture was purged with nitrogen for 5 min. Pd(OAc)2 (318 mg, 1.42 mmol) and di-tert-butyl XPhos (1.21 g, 2.85 mmol) were added and the reaction mixture was stirred at 120° C. for 20 h. The reaction mixture was diluted with EtOAc and water. After phase separation the organic layer was washed with brine, dried over MgSO4, filtered and the solution was concentrated under reduced pressure. The crude was purified by flash column chromatography on silica gel eluting with heptane and a gradient of heptane/EtOAc from [100:0] to [85:15]. The desired fractions were combined and concentrated to afford methyl 2-(6-fluoropyridin-3-yl)acetate Ex. 1a (1.98 g, 41%) as an off-white oil. |
| Ex. 1b | methyl 2-[6-(4-methanesulfonylpiperazin-1-yl)pyridin-3-yl]acetate<br>Step 2: methyl 2-(6-fluoropyridin-3-yl)acetate Ex. 1a (500 mg, 2.96 mmol) was dissolved in toluene (15 mL) and 1-methanesulfonylpiperazine (970 mg, 5.91 mmol) was added. The reaction mixture was heated at 120° C. for 72 h. The reaction mixture was diluted with EtOAc and water. After phase separation, the organic layer was washed with brine, dried over MgSO4, filtered and the solution was concentrated under reduced pressure. The crude was purified by flash column chromatography on silica gel eluting with a gradient of heptane/EtOAc from [80:20] to [0:100]. The desired fractions were combined and concentrated to afford methyl 2-[6-(4-methanesulfonylpiperazin-1-yl)pyridin-3-yl]acetate Ex. 1b (371 mg, 40%) as white solid. |
| Ex. 1 | 2-[6-(4-methanesulfonylpiperazin-1-yl)pyridin-3-yl]acetic acid<br>Step 3: methyl 2-[6-(4-methanesulfonylpiperazin-1-yl)pyridin-3-yl]acetate Ex. 1b (371 mg, 1.18 mmol) was dissolved in THF/H2O (4:1, 10 mL/2.5 mL). Lithium hydroxide monohydrate (99 mg, 2.37 mmol) wa added and the mixture was stirred at rt for 16 h. THF was removed under vacuum. EtOAc and water were added followed by 1N HCl under vigorous stirring until pH 4 was reached. The product started to precipitate in the aqueous phase. The suspension was filtered and the solid was washed with water and dried under high vacuum to afford 2-[6-(4-methanesulfonylpiperazin-1-yl)pyridin-3-yl]acetic acid Ex. 1 (179 mg, 50%) as a white solid.<br>1H NMR (300 MHz, DMSO-d6, d in ppm): 2.83 (s, 3H), 3.11 (m, 4H), 3.38 (s, 2H), 3.52 (m, 4H), 6.80 (d, 1H, J = 8.7 Hz), 7.40 (d, 1H, J = 8.7 Hz), 7.93 (s, 1H), 12.25 (br(s), 1H). |

Figure 1B:
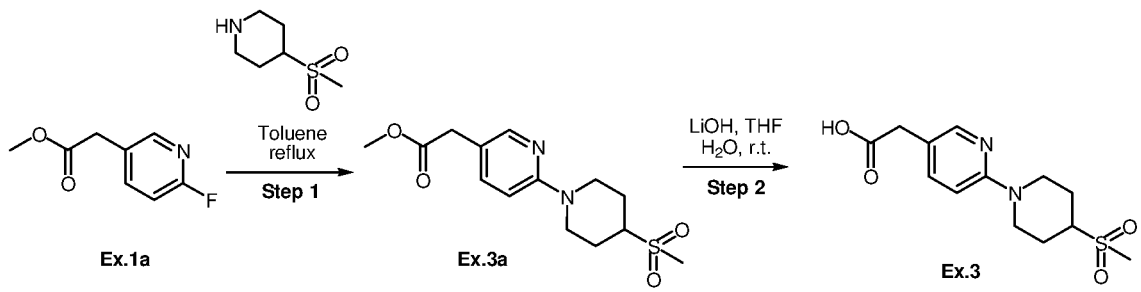

Intermediate Ex.3: 2-[6-(4-methanesulfonylpiperidin-1-yl)pyridin-3-yl]acetic acid (FIG. 1B)

TABLE 1.2

| Cpd. | Starting compounds, Reaction conditions and purification, Yield, Appearance, $^1$H NMR (solvent) data |
|---|---|
| Ex. 3a | methyl 2-[6-(4-methanesulfonylpiperidin-1-yl)pyridin-3-yl]acetate<br>Step 1: the previously synthesized methyl 2-(6-fluoropyridin-3-yl)acetate Ex. 1a (500 mg, 2.96 mmol) was dissolved in toluene (15 mL) and 4-(methylsulfonyl)piperidine (578 mg, 3.55 mmol) was added. The reaction mixture was heated at 120° C. for 24 h. Additional 4-(methylsulfonyl)piperidine (2 equiv) were added and the reaction was stirred at 120° C. for 72 h. The reaction mixture was diluted with EtOAc and water. After phase separation the combined organic layer was washed with brine, dried over MgSO4, filtered and the solution was concentrated to dryness. The crude was purified by flash column chromatography on silica gel eluting with a gradient of heptane/EtOAc from [100:0] to [0:100]. The desired fractions were combined and concentrated to afford methyl 2-[6-(4-methanesulfonylpiperidin-1-yl)pyridin-3-yl]acetate Ex. 3a (218 mg, 24%) as yellow solid |

TABLE 1.2-continued

| Cpd. | Starting compounds, Reaction conditions and purification, Yield, Appearance, $^1$H NMR (solvent) data |
|---|---|
| Ex. 3 | 2-[6-(4-methanesulfonylpiperidin-1-yl)pyridin-3-yl]acetic acid<br>Step 2: methyl 2-[6-(4-methanesulfonylpiperidin-1-yl)pyridin-3-yl]acetate Ex. 3a (218 mg, 0.70 mmol) was dissolved in THF/H2O (4:1, 8 mL/2 mL). Lithium hydroxide monohydrate (59 mg, 1.40 mmol) was added and the mixture was stirred at rt for 16 h. THF was removed under reduced pressure. EtOAc and water were added followed by 1N HCl under vigorous stirring until pH 4 was reached. The phases were separated. However, it was observed that the desired product was in both phases. Both phases were joined and absorbed on silica gel. The residue was purified by silica gel column chromatography eluting with CH2Cl2 and a gradient of CH2Cl2/MeOH from [100:0] to [75:25]. The desired fractions were combined and concentrated to dryness to afford 2-[6-(4-methanesulfonylpiperidin-1-yl)pyridin-3-yl]acetic acid Ex. 3 as a light yellow oil, which solidified under high vacuum (262 mg, quantitative yield).<br>1H NMR (300 MHz, DMSO-d6, d in ppm): 1.52 (m, 2H), 2.03 (d, 2H, J = 12.2 Hz), 2.83 (m, 2H), 2.92 (s, 3H), 3.59 (m, 2H), 4.40 (d, 2 H, J = 13.2 Hz), 6.83 (d, 1H, J = 8.7 Hz), 7.42 (d, 1H, J = 8.7Hz), 7.97 (s, 1H). |

Figure 1C:
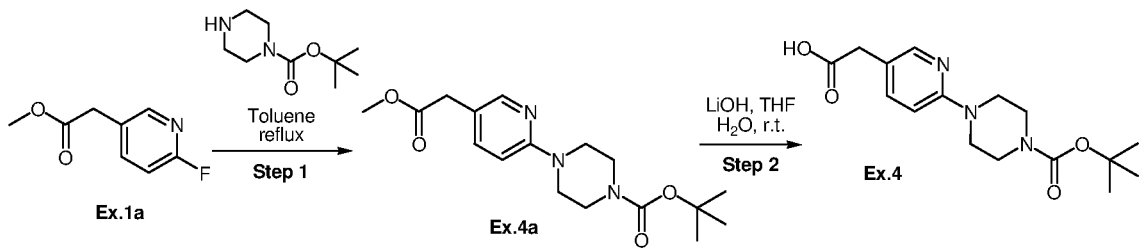

Intermediate Ex.4: 2-(6-{4-[(tert-butoxy)carbonyl]piperazin-1-yl}pyridin-3-yl)acetic acid (FIG. 1C)

TABLE 1.3

| Cpd. | Starting compounds, Reaction conditions and purification, Yield, Appearance, $^1$H NMR (solvent) data |
|---|---|
| Ex. 4a | tert-butyl 4-[5-(2-methoxy-2-oxoethyl)pyridin-2-yl]piperazine-1-carboxylate<br>Step 1: the previously synthesized methyl 2-(6-fluoropyridin-3-yl)acetate Ex. 1a (500 mg, 2.96 mmol) was dissolved in toluene (15 mL) and 1-boc-piperazine (1.65 g, 8.87 mmol) was added. The reaction mixture was heated at 120° C. for 72 h. Additional 1-boc-piperazine (2 equiv) was added and reaction was stirred at 120° C. for 72 h. The reaction mixture was diluted with EtOAc and water. After phase separation, the organic layer was washed with brine, dried over MgSO4, filtered and the solution was concentrated to dryness. The crude material was purified by flash column chromatography on silica gel eluting with heptane and a gradient of heptane/EtOAc from [100:0] to [50:50]. The desired fractions were combined and concentrate to afford tert-butyl 4-[5-(2-methoxy-2-oxoethyl)pyridin-2-yl]piperazine-1-carboxylate Ex. 4a (291 mg, 29%) as yellow solid. |
| Ex. 4 | 2-(6-{4-[(tert-butoxy)carbonyl]piperazin-1-yl}pyridin-3-yl)acetic acid<br>Step 2: tert-butyl 4-[5-(2-methoxy-2-oxoethyl)pyridin-2-yl]piperazine-1-carboxylate Ex. 4a (290 mg, 0.86 mmol) was dissolved in THF/H2O (8:1, 10 mL/2.5 mL). Lithium hydroxide monohydrate (72 mg, 1.73 mmol) was added and the mixture was stirred at rt for 16 h. 1N HCl was added under vigorous stirring until pH 4 was reached. The solvent was evaporated under reduced pressure and the residue was purified by column chromatography on silica gel eluting with CH2Cl2 and a gradient of CH2Cl2/MeOH from [100:0] to [75:25]. The product fractions were combined and concentrated to dryness to afford 2-(6-{4-[(tert-butoxy)carbonyl]piperazin-1-yl}pyridin-3-yl)acetic acid Ex.4 as a yellow oil, which solidified upon dryning at 60° C. under vacuum (232 mg, 84%).<br>1H NMR (300 MHz, DMSO-d6, d in ppm): 1.48 (s, 9H), 3.49-3.50 (m, 10H), 6.86 (d, 1H), 7.51 (m, 1H), 8.04 (s, 1H). |

Figure 1D:
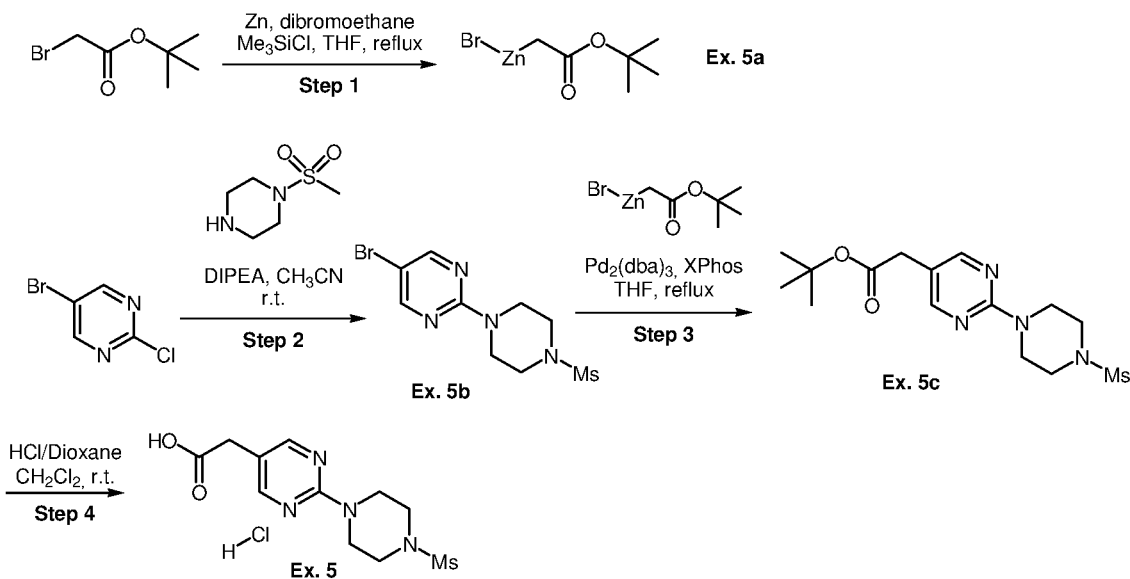

Intermediate Ex.5: 2-[2-(4-methanesulfonylpiperazin-1-yl)pyrimidin-5-yl]acetic acid hydrochloride (FIG. 1D)

TABLE 1.4

| Cpd. | Starting compounds, Reaction conditions and purification, Yield, appearance, $^1$H NMR (solvent) data |
|---|---|
| Ex. 5a | tert-butyl 2-(bromozincio)acetate<br>Step 1: to a solution of zinc dust (3.0 g, 30.26 mmol) in dry THF (25 mL) was added at rt 1,2-dibromoethane (434 µL) under nitrogen atmosphere. The reaction mixture was stirred at 70° C. for 1 min and cooled down to rt. This procedure was repeated 3 times. Me3SiCl (256 µL, 2.02 mmol) was added and the resulting suspension was stirred at rt for 15 min. It was then heated to 65° C. and a few drops of tert-butyl 2-bromoacetate were added. Then a solution of tert-butyl 2-bromoacetate (4.92 g, 25.22 mmol) in dry THF (5 mL) was added at such a rate |

TABLE 1.4-continued

| Cpd. | Starting compounds, Reaction conditions and purification, Yield, appearance, $^1$H NMR (solvent) data |
|---|---|
| | that reflux was maintained. Upon completion of addition, the reaction mixture was refluxed for an additional 20 min and allowed to cool down to rt. The zinc was allowed to settle and the supernatant was used further without any analysis. Complete conversion was assumed. |
| Ex. 5b | 5-bromo-2-(4-methanesulfonyl-piperazin-1-yl)-pyrimidine<br>Step 2: DIPEA (640 µL, 3.87 mmol) was added to 5-bromo-2-chloropyrimidine (500 mg, 2.58 mmol) in acetonitrile (11 mL). Then, 1-methanesulfonylpiperazine (420 mg, 2.58 mmol) was added to the solution. The reaction mixture was stirred at rt for 16 h. The solvent was concentrated to dryness. Water and EtOAc were added to quench the reaction. The organic layer was separated and concentrated to dryness. The crude material was purified by silica gel column chromatography eluting with heptane and a gradient of heptane/EtOAc from [100:0] to [9:1]. The product fractions were combined and concentrated to dryness to afford 5-bromo-2-(4-methanesulfonyl-piperazin-1-yl)-pyrimidine Ex. 5b (800 mg, 96%) as white solid. |
| Ex. 5c | [2-(4-methanesulfonyl-piperazin-1-yl)-pyrimidin-5-yl]-acetic acid tert-butyl ester<br>Step 3: 5-bromo-2-(4-methanesulfonyl-piperazin-1-yl)-pyrimidine Ex. 5b (800 mg, 2.49 mmol), tert-butyl 2-(bromozincio)acetate Ex. 5a (13 mL, 7.47 mmol) and dry THF (8 mL) were charged to a flask and the mixture was degassed by bubbling nitrogen through it for 5 min. Then Pd2(dba)3 (229 mg, 0.25 mmol) and XPhos (238 mg, 0.50 mmol) were added and the solution was stirred at 75° C. for 16 h. The reaction mixture was concentrated to dryness and the residue was diluted with EtOAC and water. After phase separation, the combined organic layer was washed with brine, dried over MgSO4, filtered and the solution was concentrated under reduced pressure. The crude material was purified by flash column chromatography on silica gel eluting with heptane and a gradient of heptane/EtOAc from [100:0] to [50:50]. The desired fractions were combined and concentrate to obtain [2-(4-methanesulfonyl-piperazin-1-yl)-pyrimidin-5-yl]-acetic acid tert-butyl ester Ex.5c (400 mg, 45%) as pale yellow oil. |
| Ex. 5 | 2-[2-(4-methanesulfonylpiperazin-1-yl)pyrimidin-5-yl]acetic acid hydrochloride<br>Step 4: 4N HCl in dioxane (1.12 mL, 4.48 mmol) was added to [2-(4-methanesulfonyl-piperazin-1-yl)-pyrimidin-5-yl]-acetic acid tert-butyl ester Ex. 5c (400 mg, 1.12 mmol) dissolved in CH2Cl2 (2 mL). The reaction mixture was stirred at rt for 16 h. Further 4N HCl in dioxane (1 equiv) was added to the solution. The reaction mixture was stirred at rt for additional 16 h. The reaction was not competed and additional amoutn of 4N HCl in dioxane was added until completion of the reaction (total: 1.5 equiv). A white solid (salt) was formed, it was collected by filtration, washed with Et2O and dried under vacuum until constant weight to afford 2-[2-(4-methanesulfonylpiperazin-1-yl)pyrimidin-5-yl]acetic acid hydrochloride Ex. 5 (334 mg, 99%).<br>1H NMR (300 MHz, DMSO-d6, d in ppm): 2.88 (s, 3H), 3.15-3.19 (m, 4H), 3.47 (s, 2H), 3.83-3.96 (m, 4H), 8.30 (s, 2H). |

Figure 1E:
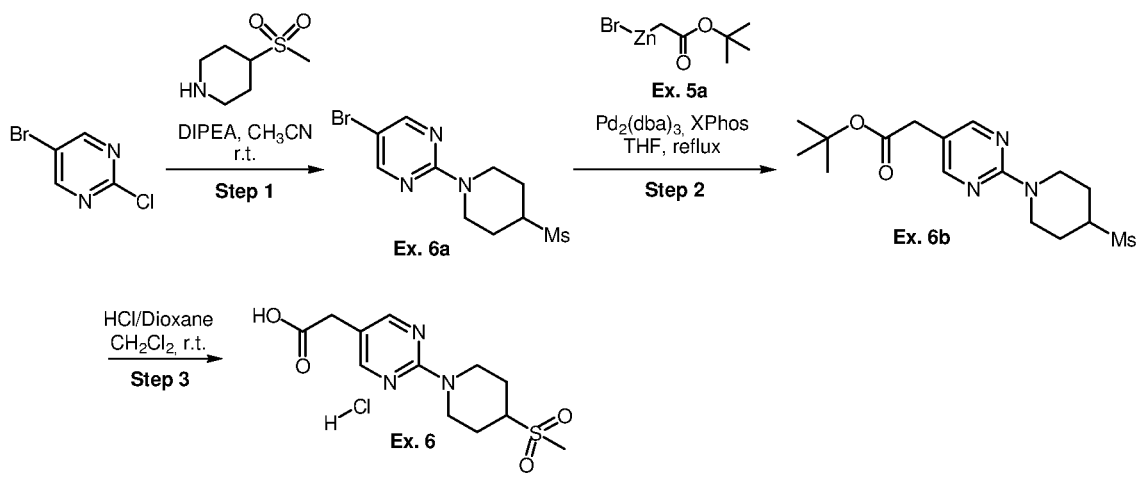

Intermediate Ex.6: 2-[2-(4-methanesulfonylpiperidin-1-yl)pyrimidin-5-yl]acetic acid (FIG. 1E)

TABLE 1.5

| Cpd. | Starting compounds, Reaction conditions and purification, Yield, Appearance, $^1$H NMR (solvent) data |
|---|---|
| Ex. 6a | 5-bromo-2-(4-methanesulfonylpiperidin-1-yl)pyrimidine<br>Step 1: DIPEA (640 µL, 3.87 mmol) was added to 5-bromo-2-chloropyrimidine (500 mg, 2.58 mmol) in acetonitrile (11 mL). Then, 4-methanesulfonylpiperidine (420 mg, 2.57 mmol) was added to the solution. The reaction mixture was stirred at rt for 16 h. The solvent was concentrated to dryness. Water and EtOAc were added to quench the reaction. The organic layer was separated and concentrated to dryness. The crude material was purified by silica gel column chromatography eluting with heptane and a gradient of heptane/EtOAc from [100:0] to [9:1]. The product fractions were combined and concentrated to dryness to afford 5-bromo-2-(4-methanesulfonylpiperidin-1-yl)pyrimidine Ex. 6a (0.628 g, 76%) as white solid. |
| Ex. 6b | tert-butyl 2-[2-(4-methanesulfonylpiperidin-1-yl)pyrimidin-5-yl]acetate<br>Step 2: 5-bromo-2-(4-methanesulfonylpiperidin-1-yl)pyrimidine Ex. 6a (628 mg, 1.77 mmol), freshly prepared tert-butyl 2-(bromozincio)acetate Ex. 5a (7 mL, 5.31 mmol) and dry THF (5 mL) were charged to a flask and the mixture was purged with nitrogen for 5 min. Then Pd2(dba)3 (165 mg, 0.18 mmol) and XPhos (167 mg, 0.35 mmol) were added and the solution was stirred at 75° C. for 16 h. The reaction mixture was concentrated and the residue was diluted with EtOAc and water. After phase separation, the organic layer was washed with brine, dried over MgSO4, filtered and the solution was concentrated to dryness. The crude was purified by flash column chromatography on silica gel eluting |

TABLE 1.5-continued

| Cpd. | Starting compounds, Reaction conditions and purification, Yield, Appearance, $^1$H NMR (solvent) data |
|---|---|
| | with heptane and a gradient of heptane/EtOAc from [100:0] to [50:50]. The desired fractions were combined and concentrate to obtain tert-butyl 2-[2-(4-methanesulfonylpiperidin-1-yl)pyrimidin-5-yl]acetate Ex. 6b (600 mg, 86%) as colourless oil. |
| Ex. 6 | 2-[2-(4-methanesulfonylpiperidin-1-yl)pyrimidin-5-yl]acetic acid<br>Step 3: tert-butyl 2-[2-(4-methanesulfonylpiperidin-1-yl)pyrimidin-5-yl]acetate Ex. 6b was dissolved in CH2Cl2 (2 mL) and 4N HCl in dioxane (1.69 mL, 6.76 mmol) was added. The reaction mixture was stirred at rt for 16 h. The reaction was monitored by TLC and additional 4N HCl in dioxane was added if needed. A white solid (salt) was formed, it was collected by filtration, washed with Et2O and dried under vacuum until constant weight to afford 2-[2-(4-methanesulfonylpiperidin-1-yl)pyrimidin-5-yl]acetic acid Ex. 6 (465 mg, 81%) as white solid.<br>1H NMR (300 MHz, DMSO-d6, d in ppm): 1.45-1.58 (m, 2H), 2.06-2.10 (m, 2H), 2.91-2.99 (m, 5H), 3.37-3.47 (m, 3H), 3.57 (s, 1H), 4.75-4.79 (m, 2H), 8.29 (s, 2H). |

Figure 1F:
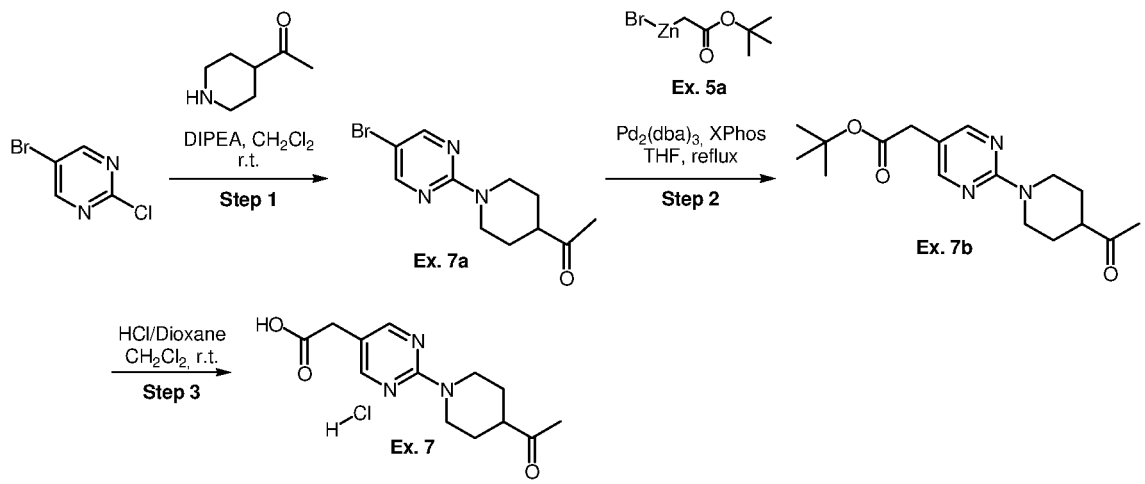

Intermediate Ex.7: 2-[2-(4-acetylpiperidin-1-yl)pyrimidin-5-yl]acetic acid (FIG. 1F)

TABLE 1.6

| Cpd. | Starting compounds, Reaction conditions and purification, Yield, Appearance, $^1$H NMR (solvent) data |
|---|---|
| Ex. 7a | 1-[1-(5-bromopyrimidin-2-yl)piperidin-4-yl]ethan-1-one<br>Step 1: DIPEA (1.066 mL, 6.45 mmol) was added to 5-bromo-2-chloropyrimidine (500 mg, 2.58 mmol) in acetonitrile (11 mL). Then, 1-piperidin-4-ethan-1-one hydrochloride (420 mg, 2.57 mmol) was added to the solution. The reaction mixture was stirred at rt for 16 h. The solvent was concentrated to dryness. Water and EtOAc were added to quench the reaction. The organic layer was separated and concentrated to dryness. The crude material was purified by silica gel column chromatography eluting with heptane and a gradient of heptane/EtOAc from [100:0] to [9:1]. The product fractions were combined and concentrated to dryness to afford 1-[1-(5-bromopyrimidin-2-yl)piperidin-4-yl]ethan-1-one Ex. 7a (495 mg, 67%) as white solid. |
| Ex. 7b | tert-butyl 2-[2-(4-acetylpiperidin-1-yl)pyrimidin-5-yl]acetate<br>Step 2: 1-[1-(5-bromopyrimidin-2-yl)piperidin-4-yl]ethan-1-one Ex. 7a (495 mg, 1.55 mmol), freshly prepared tert-butyl 2-(bromozincio)acetate Ex. 5a (5.5 mL, 4.65 mmol) and dry THF (5 mL) were charged to a flask and the mixture was purged with nitrogen for 5 min. Then Pd2(dba)3 (147 mg, 0.16 mmol) and XPhos (148 mg, 0.31 mmol) were added and the solution was stirred at 75° C. for 16 h. The reaction mixture was concentrated and the residue was diluted with EtOAc and water. After phase separation, the organic layer was washed with brine, dried over MgSO4, filtered and the solution was concentrated to dryness. The crude was purified by flash column chromatography on silica gel eluting with heptane and a gradient of heptane/EtOAc from [100:0] to [50:50]. The desired fractions were combined and concentrate to obtain tert-butyl 2-[2-(4-acetylpiperidin-1-yl)pyrimidin-5-yl]acetate Ex. 7b (124 mg, 25%) as yellow solid. |
| Ex. 7 | 2-[2-(4-acetylpiperidin-1-yl)pyrimidin-5-yl]acetic acid<br>Step 3: tert-butyl 2-[2-(4-acetylpiperidin-1-yl)pyrimidin-5-yl]acetate Ex. 7b (124 mg, 0.39 mmol) was dissolved in CH2Cl2 and 4N HCl in dioxane (2 ml, 9.37 mmol) was added. The solution was stirred at rt for 6 days. Further 4N HCl in dioxane (1 mL, 4.69 mmol) was added and stirring at rt was maintened for additional 24 h. The solvent was removed under reduced pressure. The residues were triturated with Et2O. The solid was collected by filtration and dried under vacuum until constant weight to afford 2-[2-(4-acetylpiperidin-1-yl)pyrimidin-5-yl]acetic acid Ex. 7 (68 mg, 59%) as white solid.<br>1H NMR (300 MHz, DMSO-d6, d in ppm): 1.25-1.39 (m, 2H), 1.80-1.84 (m, 2H), 2.07 (s, 3H), 2.58-2.65 (m, 1H), 2.90-2.99 (m, 2H), 3.41 (s, 2H), 4.48-4.52 (m, 2H), 8.23 (s, 2H). |

Figure 1G:
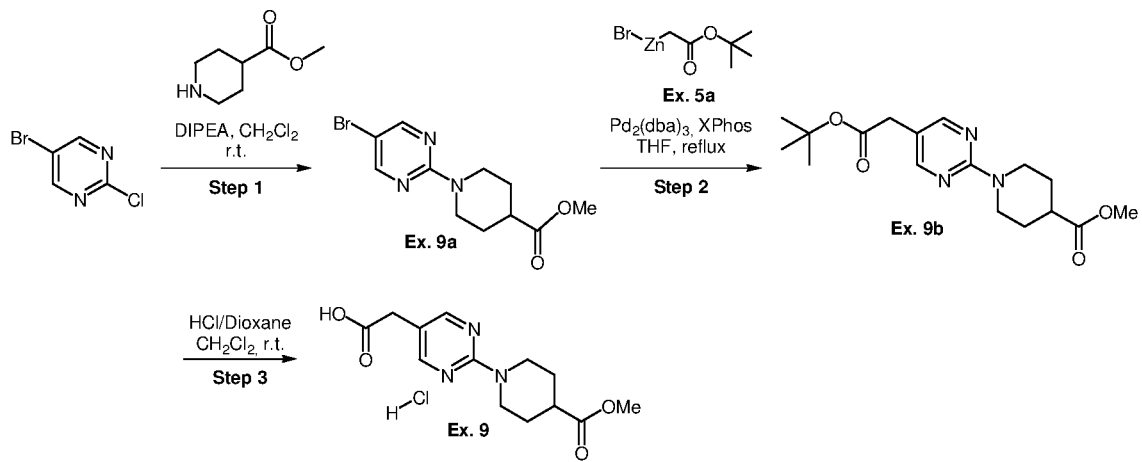

Intermediate Ex.9: 2-{2-[4-(methoxycarbonyl)piperidin-1-yl]pyrimidin-5-yl}acetic acid (FIG. 1G)

TABLE 1.7

| Cpd. | Starting compounds, Reaction conditions and purification, Yield, Appearance, $^1$H NMR (solvent) data |
| --- | --- |
| Ex. 9a | methyl 1-(5-bromopyrimidin-2-yl)piperidine-4-carboxylate<br>Step 1: DIPEA (4 mL, 23.20 mmol) was added to 5-bromo-2-chloropyrimidine (3.0 g, 15.50 mmol) in acetonitrile (80 mL). Then, methyl isonipecotate (3.321 g, 23.20 mmol) was added to the solution. The reaction mixture was stirred at rt for 16 h. The solvent was concentrated to dryness. Water and EtOAc were added to quench the reaction. The organic layer was separated and concentrated to dryness. The crude material was purified by silica gel column chromatography eluting with heptane and a gradient of heptane/EtOAc from [100:0] to [0:100]. The product fractions were combined and concentrated to dryness to afford methyl 1-(5-bromopyrimidin-2-yl)piperidine-4-carboxylate Ex. 9a (1.84 mg, 41%) as white solid. |
| Ex. 9b | methyl 1-[5-[2-(tert-butoxy)-2-oxoethyl]pyrimidin-2-yl}piperidine-4-carboxylate<br>Step 2: methyl 1-(5-bromopyrimidin-2-yl)piperidine-4-carboxylate Ex. 9a (1.00 g, 3.33 mmol), freshly prepared tert-butyl 2-(bromozincio)acetate Ex. 5a (11.7 mL, 9.99 mmol) and dry THF (10 mL) were charged to a flask and the mixture was purged with nitrogen for 5 min. Then Pd2(dba)3 (302 mg, 0.33 mmol) and XPhos (319 mg, 0.67 mmol) were added and the solution was stirred at 75° C. for 16 h. The reaction mixture was concentrated and the residue was diluted with EtOAc and water. After phase separation, the organic layer was washed with brine, dried over MgSO4, filtered and the solution was concentrated to dryness. The crude was purified by flash column chromatography on silica gel eluting with heptane and a gradient of heptane/EtOAc from [100:0] to [50:50]. The desired fractions were combined and concentrate to obtain methyl 1-[5-[2-(tert-butoxy)-2-oxoethyl]pyrimidin-2-yl}piperidine-4-carboxylate Ex. 9b (930 mg, 28%) as pale yellow oil. |
| Ex. 9 | 2-{2-[4-(methoxycarbonyl)piperidin-1-yl]pyrimidin-5-yl}acetic acid<br>Step 3: 4N HCl in dioxane (2.77 mL, 11.08 mmol) was added to methyl 1-{5-[2-(tert-butoxy)-2-oxoethyl]pyrimidin-2-yl}piperidine-4-carboxylate Ex. 9b (930 mg, 2.77 mmol) dissovled in CH2Cl2 (2 mL). The reaction mixture was stirring at rt for 16 h. The reaction mixture was concentrated, the solid was triturated with Et2O and some drops of CH2Cl2. The obtained solid was collected by filtration, washed with Et2O and dried under vacuum at 60° C. to constant weight. LCMS showed the desired product and some impurities. The solid was suspended in EtOAc and sat. NaHCO3 solution was added dropwise under vigorous stirring until a clear two-phase mixture was obtained. The organic layer was separated, the aqueous was extracted with more EtOAc and the combined organic layers were concentrated to dryness. The crude material was purified by silica gel column chromatography eluting with CH2Cl2 and a gradient of CH2Cl2/MeOH from [100:0] to [95:5]. The product fractions were combined and concentrated to dryness to afford 2-{2-[4-(methoxycarbonyl)piperidin-1-yl]pyrimidin-5-yl}acetic acid Ex. 9 (271 mg, 35%) as an off-white solid.<br>1H NMR (300 MHz, DMSO-d6, d in ppm): 1.41-1.55 (m, 2H), 1.85-1.89 (m, 2H), 2.64-2.69 (m, 1H), 2.98-3.07 (m, 2H), 3.44 (s, 2H), 3.61 (s, 3H), 4.47-4.52 (m, 2H), 8.24 (s, 2H), 12.43 (br(s), 1H). |

Figure 1H:
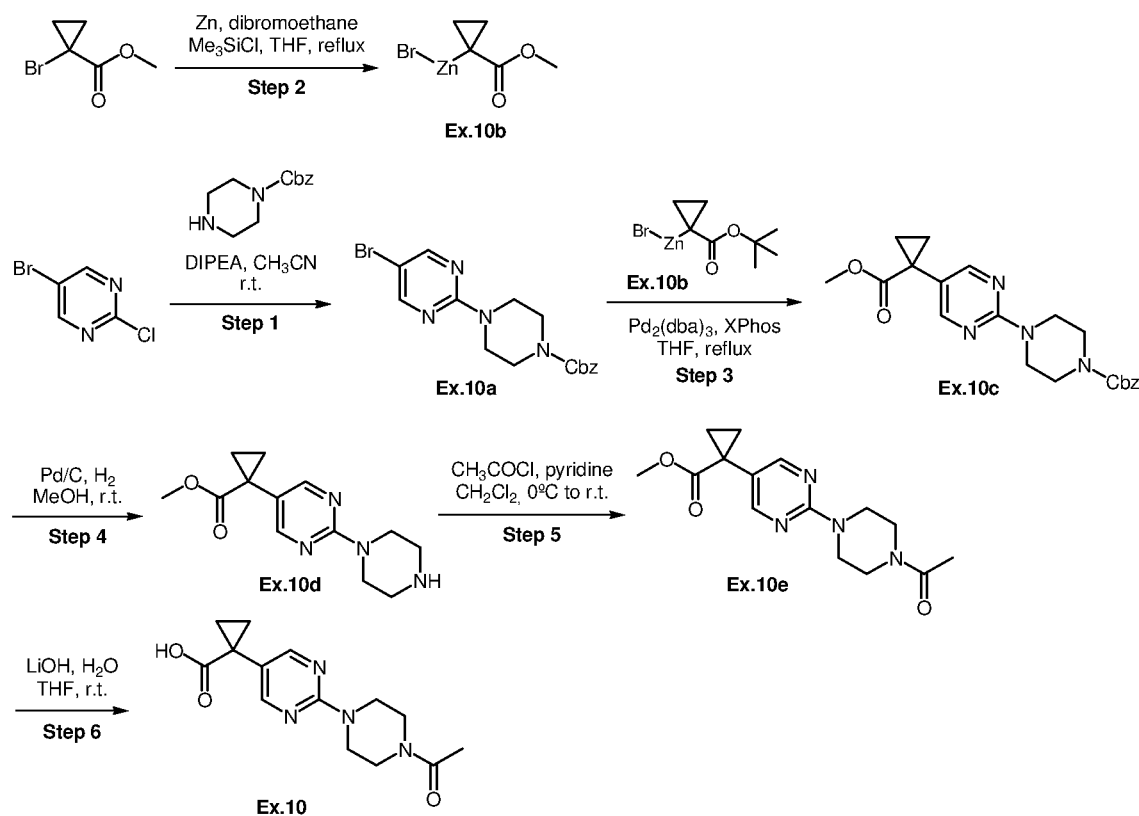

Intermediate Ex.10: 1-[2-(4-acetylpiperazin-1-yl)pyrimidin-5-yl]cyclopropane-1-carboxylic acid (FIG. 1H)

TABLE 1.8

| Cpd. | Starting compounds, Reaction conditions and purification, Yield, Appearance, $^1$H NMR (solvent) data |
| --- | --- |
| Ex. 10a | benzyl 4-(5-bromopyrimidin-2-yl)piperazine-1-carboxylate<br>Step 1: DIPEA (879 µL, 5.17 mmol) was added to 5-bromo-2-chloropyrimidine (500 mg, 2.56 mmol) in acetonitrile (12 mL). Then, benzyl piperazine-1-carboxylate (500 µL, 2.56 mmol) was added to the mixture. The reaction mixture was stirred at r.t. for 60 h. Water and EtOAc were added. The two phases were separated and the aqueous solution was extracted with EtOAc. The combined organic layers were dried over MgSO4, filtered and the solution was concentrated to dryness. The crude material was purified by column chromatography on silica gel eluting with Heptane/EtOAc from [100:0] to [0:100]. The product fractions were combined and concentrated to dryness to afford benzyl 4-(5-bromopyrimidin-2-yl)piperazine-1-carboxylate Ex. 10a (858 mg, 88%) as white solid. |

TABLE 1.8-continued

| Cpd. | Starting compounds, Reaction conditions and purification, Yield, Appearance, $^1$H NMR (solvent) data |
|---|---|
| Ex. 10b | bromo[1-(methoxycarbonyl)cyclopropyl]zinc<br>Step 2: to a solution of zinc dust (3.0 g, 30.26 mmol) in dry THF (25 mL) was added at r.t. 1,2-dibromoethane (434 µL, 5.04 mmol) under nitrogen atmosphere. The reaction mixture was stirred at 70° C. for 1 min and cooled down to r.t. This procedure was repeated 3 times. Me3SiCl (256 µL, 2.02 mmol) was added and the resulting suspension was stirred at r.t. for 15 min. It was then heated to 65° C. and a few drops of methyl 1-bromocyclopropane-1-carboxylate were added. Then a solution of methyl 1-bromocyclopropane-1-carboxylate (2.61 mL, 25.22 mmol) in dry THF (5 mL) was added at such a rate that reflux was maintained. Upon completion of addition, the reaction mixture was refluxed for an additional 20 min and allowed to cool down to r.t. The zinc was allowed to settle and the supernatant was used further without any analysis. Complete conversion was assumed. |
| Ex. 10c | benzyl 4-{5-[1-(methoxycarbonyl)cyclopropyl]pyrimidin-2-yl}piperazine-1-carboxylate<br>Step 3: benzyl 4-(5-bromopyrimidin-2-yl)piperazine-1-carboxylate Ex. 10a (300 mg, 0.80 mmol), freshly prepared bromo[1-(methoxycarbonyl)cyclopropyl]zinc Ex. 10b (3 mL, 2.39 mmol) and dry THF (5 mL) were placed in flask, the mixture was degassed by nitrogen bubbling for 5 min. Then Pd2(dba)3 (72 mg, 0.08 mmol) and XPhos (76 mg, 0.16 mmol) were incorporated and the reaction mixture was stirred at 75° C. for 16 h. The reaction mixture was concentrated under reduced pressure, the residue was diluted with EtOAc/H2O and the two phases were separated. The organic layer was dried over MgSO4, filtered and the solution was concentrated under reduced pressure. The crude material was purified by flash chromatography on silica gel eluting with a gradient of Heptane/EtOAc from [100:0] to [50:50]. The desired fractions were combined and concentrated to obtain benzyl 4-{5-[1-(methoxycarbonyl)cyclopropyl]pyrimidin-2-yl}piperazine-1-carboxylate Ex. 10c (298 mg, 95%) as white solid. |
| Ex. 10d | methyl 1-[2-(piperazin-1-yl)pyrimidin-5-yl]cyclopropane-1-carboxylate<br>Step 4: benzyl 4-{5-[1-(methoxycarbonyl)cyclopropyl]pyrimidin-2-yl}piperazine-1-carboxylate Ex. 10c (298 mg, 0.75 mmol) was dissolved in EtOAc (15 mL). The solution was purged with nitrogen and Pd/C (10% w/w) was added under nitrogen atmosphere. The nitrogen atmosphere was replaced by hydrogen (balloon) and the mixture was stirred at r.t. for 36 h. After the completion of the reaction, the catalyst was removed by filtration. The filtrate was concentrated to dryness to afford methyl 1-[2-(piperazin-1-yl)pyrimidin-5-yl]cyclopropane-1-carboxylate Ex. 10d (196 mg, 99%) as white solid. |
| Ex. 10e | methyl 1-[2-(4-acetylpiperazin-1-yl)pyrimidin-5-yl]cyclopropane-1-carboxylate<br>Step 5: acetyl chloride (59 µL, 0.82 mmol) was added at 0° C. to a mixture of methyl 1-[2-(piperazin-1-yl)pyrimidin-5-yl]cyclopropane-1-carboxylate Ex. 10d (196 mg, 0.74 mmol) and pyridine (90 µL, 1.12 mmol) in CH2Cl2 (5 mL). Then, the reaction mixture was stirred at r.t overnight. After the completion of the reaction, the mixture was concentrated to dryness. The residue was diluted with CH2Cl2 and water. The two phases were separated. The organic layer was dried over MgSO4, filtered and the solution was concentrated under reduced pressure. The crude material was purified by column chromatography on silica gel eluting with a gradient of Heptane/EtOAc from [50:50] to [0:100]. The desired fractions were combined and concentrated to obtain methyl 1-[2-(4-acetylpiperazin-1-yl)pyrimidin-5-yl]cyclopropane-1-carboxylate Ex. 10e (205 mg, 90%) as white solid. |
| Ex. 10 | 1-[2-(4-acetylpiperazin-1-yl)pyrimidin-5-yl]cyclopropane-1-carboxylic acid<br>Step 6: methyl 1-[2-(4-acetylpiperazin-1-yl)pyrimidin-5-yl]cyclopropane-1-carboxylate Ex. 10e (205 mg, 0.67 mmol) was dissolved in THF (8 mL). Water (2 mL) was added followed by lithium hydroxide monohydrate (57 mg, 1.35 mmol) and the mixture was stirred at r.t. for 16 h. THF was removed under vacuum. EtOAc and water were added followed by 1M HCl under vigorous stirring until pH = 4 was reached. The phases were separated and the organic phase was dried over MgSO4, filtered and the solution was concentrated to dryness to afford 1-[2-(4-acetylpiperazin-1-yl)pyrimidin-5-yl]cyclopropane-1-carboxylic acid Ex. 10 (133 mg, 68%) as white solid.<br>1H NMR (300 MHz, DMSO-d6, d in ppm): 1.12 (br(s), 2H), 1.42 (br(s), 2H), 2.05 (s, 3H), 3.51 (br(s), 4H), 3.68-3.76 (m, 4H), 8.32 (s, 2H). The acidic proton exchanged with the deuterated solvent. |

Figure 1I:
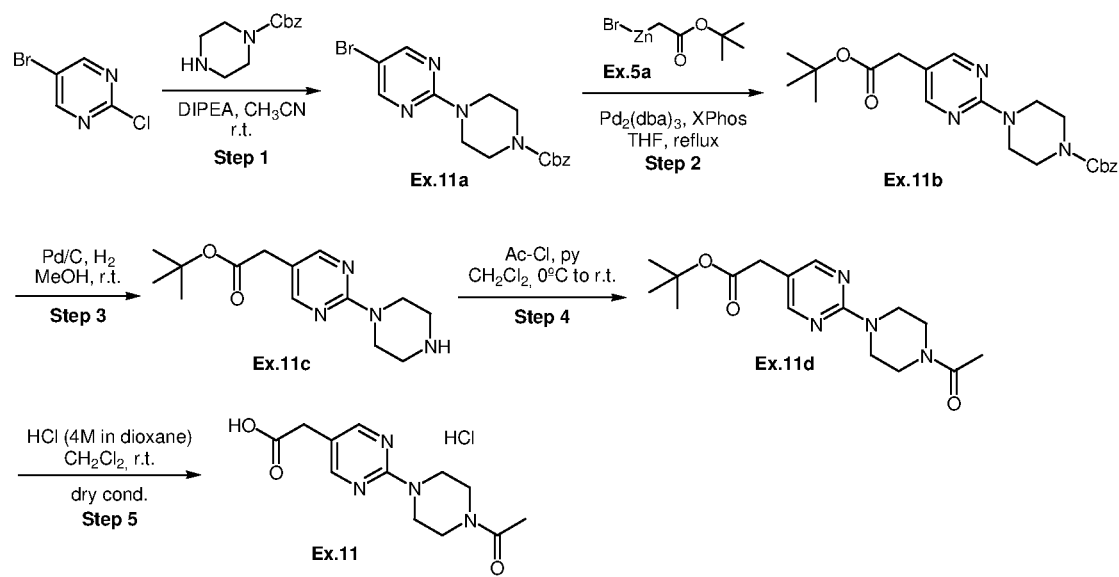

Intermediate Ex.11: 2-[2-(4-acetylpiperazin-1-yl) pyrimidin-5-yl]acetic acid hydrochloride (FIG. 1I)

TABLE 1.9

| Cpd. | Starting compounds, Reaction conditions and purification, Yield, Appearance, $^1$H NMR (solvent) data |
|---|---|
| Ex. 11a | benzyl 4-(5-bromopyrimidin-2-yl)piperazine-1-carboxylate<br>Step 1: DIPEA (879 µL, 5.17 mmol) was added to 5-bromo-2-chloropyrimidine (500 mg, 2.56 mmol) in acetonitrile (12 mL). Then, benzyl piperazine-1-carboxylate (500 µL, 2.56 mmol) was added to the mixture. The reaction mixture was stirred at r.t. for 60 h. Water and EtOAc were added. The two phases were separated and the aqueous solution was extracted with EtOAc. The combined organic layers were dried over MgSO4, filtered and the solution was concentrated to dryness. The crude material was purified by column chromatography on silica gel eluting with Heptane/EtOAc from [100:0] to [0:100]. The product fractions were combined and concentrated to dryness to afford benzyl 4-(5-bromopyrimidin-2-yl)piperazine-1-carboxylate Ex. 11a (858 mg, 88%) as white solid. |
| Ex. 11b | benzyl 4-{5-[2-(tert-butoxy)-2-oxoethyl]pyrimidin-2-yl}piperazine-1-carboxylate<br>Step 2: benzyl 4-(5-bromopyrimidin-2-yl)piperazine-1-carboxylate Ex. 11a (500 mg, 1.33 mmol), freshly prepared tert-butyl 2-(bromozincio)acetate Ex. 5a (5 mL, 3.98 mmol) and dry THF (7 mL) were charged to a flask and the mixture was purged with nitrogen for 5 min. Then Pd2(dba)3 (120 mg, 0.13 mmol) and XPhos (126 mg, 0.26 mmol) were incorporated and the reaction mixture was stirred at 75° C. for 16 h. The reaction mixture was concentrated under reduced pressure, the residue was diluted with EtOAc/H2O and the two phases were separated. The organic layer was dried over MgSO4, filtered and the solution was concentrated under reduced pressure. The crude material was purified by flash chromatography on silica gel eluting with a gradient of Heptane/EtOAc from [100:0] to [0:100]. The desired fractions were combined and concentrated to obtain benzyl 4-{5-[2-(tert-butoxy)-2-oxoethyl]pyrimidin-2-yl}piperazine-1-carboxylate Ex. 11b (360 mg, 66%) as white solid. |
| Ex. 11c | tert-butyl 2-[2-(piperazin-1-yl)pyrimidin-5-yl]acetate<br>Step 3: benzyl 4-{5-[2-(tert-butoxy)-2-oxoethyl]pyrimidin-2-yl}piperazine-1-carboxylate Ex. 11a (360 mg, 0.24 mmol) and Pd/C (30% w/w) were mixed in MeOH (1 mL) and the mixture was stirred at r.t. for 20 h under H2 atmosphere. After completion of the reaction, the mixture was filtered, and the filtrate was concentrated under reduced pressure to afford tert-butyl 2-[2-(piperazin-1-yl)pyrimidin-5-yl]acetate Ex. 11c. The mixture was used in the next step without further purification. |
| Ex. 11d | tert-butyl 2-[2-(4-acetylpiperazin-1-yl)pyrimidin-5-yl]acetate<br>Step 4: acetyl chloride (60 µL, 0.83 mmol) was added at 0° C. to a mixture of tert-butyl 2-[2-(piperazin-1-yl)pyrimidin-5-yl]acetate Ex. 11c (210 mg, 0.75 mmol) and pyridine (92 µL, 1.13 mmol) in CH2Cl2 (10 mL). Then, the reaction mixture was stirred at r.t overnight. The reaction was quenched with water and diluted with CH2Cl2. The two phases were separated. The organic layer was dried over MgSO4, filtered and the solution was concentrated under reduced pressure. The residue was purified by column chromatography on silica gel eluting with a gradient of CH2Cl2/MeOH from [100:0] to [0:100]. The product fractions were combined and concentrated to dryness to afford tert-butyl 2-[2-(4-acetylpiperazin-1-yl)pyrimidin-5-yl]acetate Ex. 11d (156 mg, 65%) as white solid. |
| Ex. 11 | 2-[2-(4-acetylpiperazin-1-yl)pyrimidin-5-yl]acetic acid hydrochloride<br>Step 5: HCl (4M in dioxane) (1 mL, 1.95 mmol) was added to tert-butyl 2-[2-(4-acetylpiperazin-1-yl)pyrimidin-5-yl]acetate Ex. 11d (156 mg, 0.49 mmol) dissolved in CH2Cl2 (3 mL). The reaction mixture was stirring for 16 h at r.t. A pale brown solid (salt) was formed, it was collected by filtration, washed with CH2Cl2 and diethyl ether and dried under vacuum up the constant weight was reached to give 2-[2-(4-acetylpiperazin-1-yl)pyrimidin-5-yl]acetic acid hydrochloride Ex. 11 (85 mg, 66%) as pale brown solid.<br>1H NMR (300 MHz, DMSO-d6, d in ppm): 2.08 (s, 3H), 3.50 (s, 2H), 3.50-3.53 (m, 4H), 3.68-3.71 (m, 2H), 3.75-3.78 (m, 2H), 8.31 (s, 2H). The acidic proton exchanged with the deuterated solvent. |

Figure 1J:
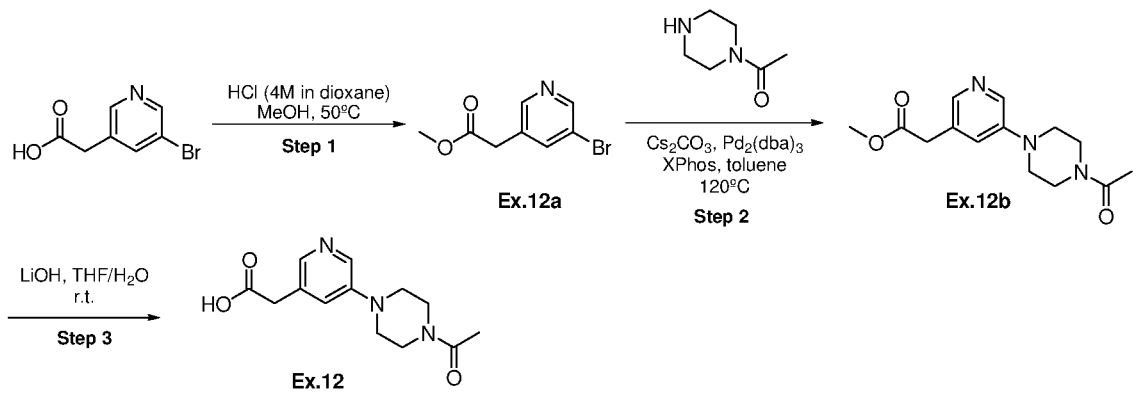

Intermediate Ex.12: 2-[5-(4-acetylpiperazin-1-yl)
pyridin-3-yl]acetic acid (FIG. 1J)

TABLE 1.10

| Cpd. | Starting compounds, Reaction conditions and purification, Yield, Appearance, $^1$H NMR (solvent) data |
|---|---|
| Ex. 12a | methyl 2-(5-bromopyridin-3-yl)acetate<br>Step 1: 2-(5-bromopyridin-3-yl)acetic acid (500 mg, 2.31 mmol) was dissolved in MeOH (30 mL). HCl (4M in dioxane) (10 mL) was added and the mixture was heated overnight at 50° C. The mixture was concentrated to dryness. The oil was partitioned between EtOAc and sat. NaHCO3 solution. The organic layer was dried over MgSO4, filtered and the solution was concentrated to dryness. The resulting oil was purified by column chromatography on silica gel eluting with a gradient of Heptane/EtOAc from [100:0] to [50:50]. The product fractions were combined and concentrated to dryness to afford methyl 2-(5-bromopyridin-3-yl)acetate Ex. 12a (412 mg, 77%) as colorless oil. |
| Ex. 12b | methyl 2-[5-(4-acetylpiperazin-1-yl)pyridin-3-yl]acetate<br>Step 2: methyl 2-(5-bromopyridin-3-yl)acetate Ex. 12a (303 mg, 1.32 mmol), 1-(piperazin-1-yl)ethan-1-one (247 μL, 1.98 mmol) and Cs2CO3 (644 mg, 1.98 mmol) were charged to a screw cap tube, dry toluene (4 mL) was added and the mixture was degassed by nitrogen bubbling for 5 min. Then Pd2(dba)3 (60 mg, 0.07 mmol) and XPhos (63 mg, 0.13 mmol) were incorporated and the reaction mixture was stirred at 110° C. for 16 h. The reaction mixture was cooled to r.t., diluted with EtOAc and water. The two phases were separated. The organic layer was dried over MgSO4, filtered and the solution was concentrated to dryness. The crude material was purified by column chromatography eluting with a gradient of Heptane/EtOAc from [100:0] to [0:100]. The product fractions were combined and concentrated to dryness to afford methyl 2-[5-(4-acetylpiperazin-1-yl)pyridin-3-yl]acetate Ex. 12b (97 mg, 13%) as yellow oil. |
| Ex. 12 | 2-[5-(4-acetylpiperazin-1-yl)pyridin-3-yl]acetic acid<br>Step 3: Lithium hydroxide monohydrate (15 mg, 0.35 mmol) was added at 0° C. to the mixture of methyl 2-[5-(4-acetylpiperazin-1-yl)pyridin-3-yl]acetate Ex. 12b (97 mg, 0.35 mmol) diluted in THF (5 mL) and water (2.5 mL). Then, the mixture was stirred overnight at r.t. The reaction mixture was concentrated to dryness. Water followed by 1M HCl was added to the mixture under vigorous stirring until pH = 2 was reached. The aqueous solution was extracted with EtOAc. The organic and aqueous layers were separated. LCMS showed that product was remaining in the aqueous layer. The aqueous layer was concentrated to dryness to afford 2-[5-(4-acetylpiperazin-1-yl)pyridin-3-yl]acetic acid Ex. 12 (209 mg, no yield calculated as it contains residues of lithium) as brown oil 1H NMR (300 MHz, DMSO-d6, d in ppm): 2.06 (s, 3H), 3.60 (s, 4H), 3.79 (s, 2H), 7.94 (s, 1H), 8.13 (s, 1H), 8.34 (s, 1H). The acidic proton exchanged with the deuterated solvent. |

Figure 1K:
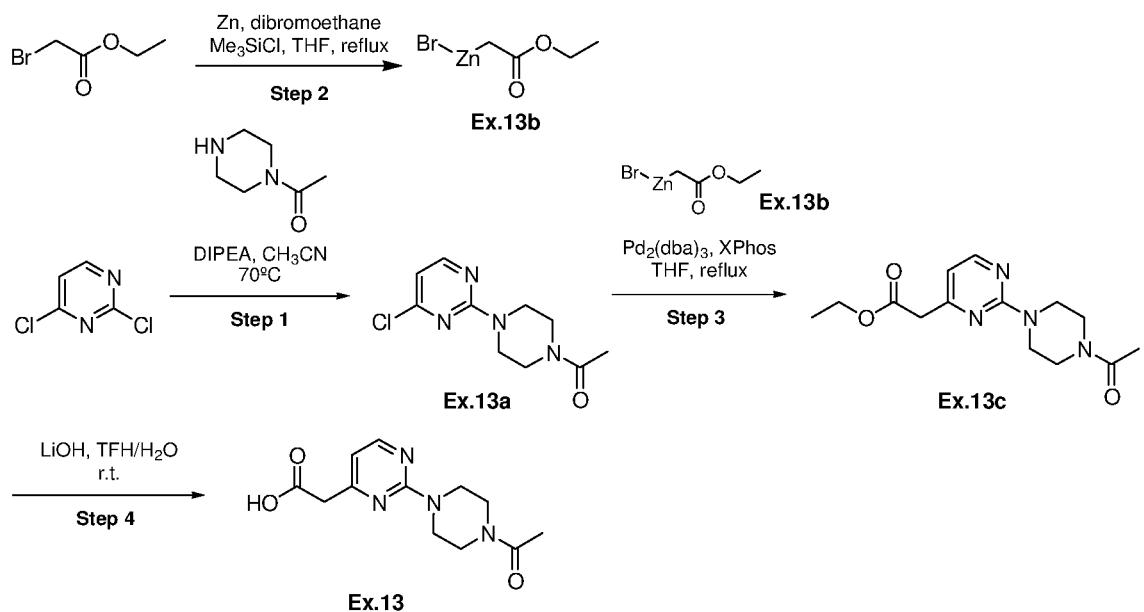

Intermediate Ex.13: 2-[2-(4-acetylpiperazin-1-yl)
pyrimidin-4-yl]acetic acid (FIG. 1K)

TABLE 1.11

| Cpd. | Starting compounds, Reaction conditions and purification, Yield, Appearance, $^1$H NMR (solvent) data |
|---|---|
| Ex. 13a | 1-[4-(4-chloropyrimidin-2-yl)piperazin-1-yl]ethan-1-one<br>Step 1: DIPEA (1.76 mL, 10.1 mmol) was added to 2,4-dichloropyrimidine (1.0 g, 6.72 mmol) dissolved in acetonitrile (30 mL). Then, 1-(piperazin-1-yl)ethan-1-one (840 μL, 6.72 mmol) was added to the mixture. The reaction mixture was heated overnight at 70° C. The solution was concentrated to dryness. Water followed by EtOAc were added to the residue. The two phases were separated. The organic layer was concentrated under reduced pressure. The crude material was purified by column chromatography eluting with EtOAc (100%). The desired fractions were combined and concentrated to dryness to afford 1-[4-(4-chloropyrimidin-2-yl)piperazin-1-yl]ethan-1-one Ex. 13a (1.39 g, 86%) as white solid. |
| Ex. 13b | ethyl 2-(bromozincio)acetate<br>Step 2: to a solution of zinc dust (4.0 g, 40.35 mmol) in dry THF (35 mL) was added at r.t. 1,2-dibromoethane (579 μL, 6.72 mmol) under nitrogen atmosphere. The reaction mixture was stirred at 70° C. for 1 min and cooled down to r.t. This procedure was repeated 5 times. Me3SiCl (341 μL, 2.69 mmol) was added and the resulting suspension was stirred at r.t. for 15 min. It was then heated to 65° C. and a few drops of ethyl 2-bromoacetate were added. Then a solution of ethyl 2-bromoacetate (3.73 mL, 33.62 mmol) in dry THF (5 mL) was added at such a rate that reflux was maintained. Upon completion of addition, the reaction mixture was refluxed for an additional 20 min and allowed to cool down to r.t. The zinc was allowed to settle and the supernatant was used further without any analysis. Complete conversion was assumed. |

TABLE 1.11-continued

| Cpd. | Starting compounds, Reaction conditions and purification, Yield, Appearance, $^1$H NMR (solvent) data |
|---|---|
| Ex. 13c | ethyl 2-[2-(4-acetylpiperazin-1-yl)pyrimidin-4-yl]acetate<br>Step 3: 1-[4-(4-chloropyrimidin-2-yl)piperazin-1-yl]ethan-1-one Ex. 13a (800 mg, 3.32 mmol), freshly prepared ethyl 2-(bromozincio)acetate Ex. 13b (12 mL, 9.97 mmol) and dry THF (5 mL) were charged to a flask and the mixture was purged with nitrogen for 5 min. Then Pd2(dba)3 (304 mg, 0.33 mmol) and XPhos (316 mg, 0.66 mmol) were incorporated and the reaction mixture was stirred at 75° C. for 16 h. The reaction mixture was concentrated under reduced pressure, the residue was diluted with CH2Cl2/H2O and the two phases were separated. The organic layer was dried over MgSO4, filtered and the solution was concentratedunder reduced pressure. The crude material was purified by flash chromatography on silica gel eluting with a gradient of CH2Cl2/MeOH from [100:0] to [90:10]. The desired fractions were combined and concentrated to obtain ethyl 2-[2-(4-acetylpiperazin-1-yl)pyrimidin-4-yl]acetate Ex. 13c (135 mg, 14%) as yellow oil. |
| Ex. 13 | 2-[2-(4-acetylpiperazin-1-yl)pyrimidin-4-yl]acetic acid<br>Step 4: Lithium hydroxide monohydrate (19 mg, 0.46 mmol) was added at 0° C. to the mixture of ethyl 2-[2-(4-acetylpiperazin-1-yl)pyrimidin-4-yl]acetate Ex. 13c (135 mg, 0.46 mmol) diluted in THF (3 mL) and water (1 mL). Then, the mixture was stirred overnight at r.t. The reaction mixture was concentrated to dryness. Water followed by 1M HCl was added to the mixture under vigorous stirring until pH = 2 was reached. The aqueous solution was extracted with EtOAc. The organic and aqueous layers were separated. LCMS showed that product was remaining in the aqueous layer. The aqueous layer was concentrated to dryness to afford 2-[2-(4-acetylpiperazin-1-yl)pyrimidin-4-yl]acetic acid Ex. 13 (149 mg, no yield calculated as it contains residues of lithium) as yellow solid.<br>1H NMR (300 MHz, DMSO-d6, d in ppm): 2.04 (s, 3H), 3.47-3.69 (m, 10H), 6.60 (d, 1H, J = 6.1 Hz), 8.07 (d, 1H, J = 6.1 Hz). The acidic proton exchanged with the deuterated solvent. |

Figure 1L:
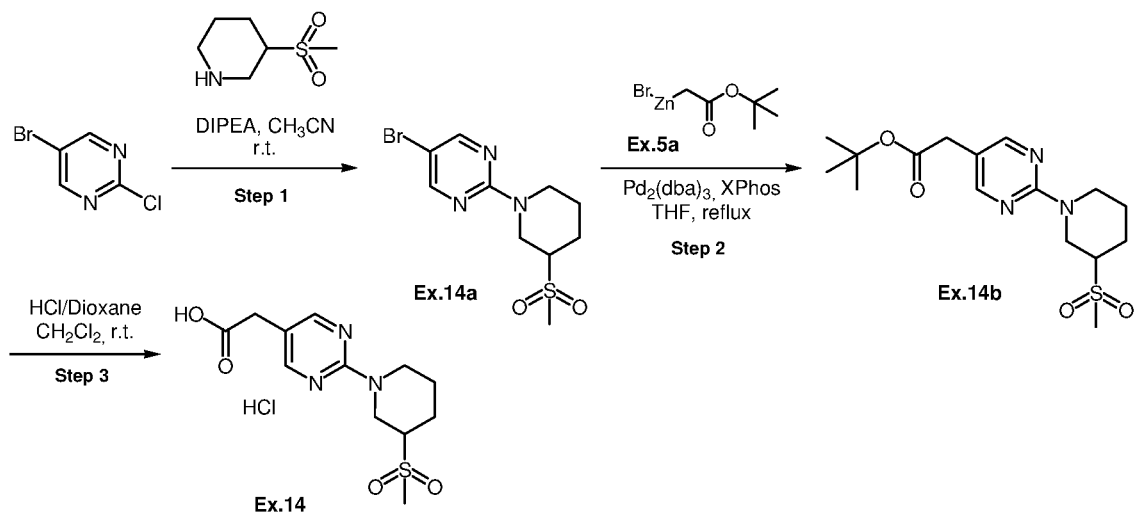

Intermediate Ex.14: 2-[2-(3-methanesulfonylpiperi-din-1-yl)pyrimidin-5-yl]acetic acid hydrochloride
(FIG. 1L)

TABLE 1.12

| Cpd. | Starting compounds, Reaction conditions and purification, Yield, Appearance, $^1$H NMR (solvent) data |
|---|---|
| Ex. 14a | 5-bromo-2-(3-methanesulfonylpiperidin-1-yl)pyrimidine<br>Step 1: DIPEA (663 µL, 3.88 mmol) was added to 5-bromo-2-chloropyrimidine (500 mg, 2.56 mmol) dissolved in acetonitrile (20 mL). Then, 3-methanesulfonylpiperidine (422 mg, 2.56 mml) was added to the solution. The reaction mixture was stirred overnight at r.t. The solvent was removed under reduced pressure. Water followed by EtOAc were added to the residue. The two phases were partitionated. The organic layer was dried over MgSO4, filtered and the solution was concentrated to dryness. The crude material was purified by column chromatography on silica gel eluting with a gradient of Heptane/EtOAc from [100:0] to [0:100]. The product fractions were combined and concentrated to dryness to afford 5-bromo-2-(3-methanesulfonylpiperidin-1-yl)pyrimidine Ex. 14a (443 mg, 54%) as white solid. |
| Ex. 14b | tert-butyl 2-[2-(3-methanesulfonylpiperidin-1-yl)pyrimidin-5-yl]acetate<br>Step 2: 5-bromo-2-(3-methanesulfonylpiperidin-1-yl)pyrimidine Ex. 14a (443 mg, 1.38 mmol), freshly prepared tert-butyl 2-(bromozincio)acetate Ex. 5a (5 mL, 4.15 mmol) and dry THF (7 mL) were charged to a flask and the mixture was purged with nitrogen for 5 min. Then Pd2(dba)3 (126 mg, 0.14 mmol) and XPhos (131 mg, 0.28 mmol) were incorporated and the reaction mixture was stirred at 75° C. for 16 h. The reaction mixture was concentrated under reduced pressure, the residue was diluted with EtOAc/H2O and the two phases were separated. The organic layer was dried over MgSO4, filtered and the solution was concentrated under reduced pressure. The crude material was purified by flash chromatography on silica gel eluting with a gradient of Heptane/EtoAc from [100:0] to [0:100]. The desired fractions were combined and concentrated to obtain tert-butyl 2-[2-(3-methanesulfonylpiperidin-1-yl)pyrimidin-5-yl]acetate Ex. 14b (390 mg, 79%) as yellow oil. |
| Ex. 14 | 2-[2-(3-methanesulfonylpiperidin-1-yl)pyrimidin-5-yl]acetic acid hydrochloride<br>Step 3: HCl (4M in dioxanne) (1.10 mL, 1.10 mmol) was added to tert-butyl 2-[2-(3-methanesulfonylpiperidin-1-yl)pyrimidin-5-yl]acetate Ex. 14b (390 mg, |

TABLE 1.12-continued

| Cpd. | Starting compounds, Reaction conditions and purification, Yield, Appearance, $^1$H NMR (solvent) data |
| --- | --- |
| | 1.10 mmol) in dissolved in CH2Cl2 (3 mL). The reaction mixture was stirring overnight at r.t. A pale brown solid (salt) was formed, it was collected by filtration, washed with CH2Cl2 and diethyl ether and dried under vacuum at constant weight to give 2-[2-(3-methanesulfonylpiperidin-1-yl)pyrimidin-5-yl]acetic acid hydrochloride Ex. 14 (320 mg, 87%).<br>1H NMR (300 MHz, DMSO-d6, d in ppm): 1.38-1.55 (m, 1H), 1.69-1.89 (m, 2H), 2.12-2.24 (m, 1H), 2.90-2.97 (m, 1H), 3.00 (s, 3H), 3.09-3.29 (m, 4H), 3.48 (s, 2H), 4.53 (d, 1H, J = 13.1 Hz), 4.96 (d, 1H, J = 11.4 Hz), 8.32 (s, 2H). |

Example 1b: Synthesis of Amine Intermediates for the Synthesis of Compounds According to the Invention The following amines were obtained following the procedure described in WO2016102633

TABLE 1.13

| Ex. 2 | [4-methyl-2-(piperidin-1-yl)phenyl](5-methylfuran-2-yl)methanamine |
| --- | --- |

Intermediate Ex.8: (2,4-dimethylphenyl)(5-methyl-furan-2-yl)methanamine (FIG. 2)

TABLE 1.14

| Cpd. | Starting compounds, Reaction conditions and purification, | Yield, Appearance, $^1$H NMR (solvent) data |
| --- | --- | --- |
| Ex. 8a | 2-methyl-N-[(5-methylfuran-2-yl)methylidene]propane-2-sulfinamide<br>Step 1: 5-methylfuran-2-carbaldehyde (1.0 g, 9.08 mmol) was dissolved in dry THF (5 mL). Titanium ethoxide (7.62 mL, 36.3 mmol) and rac-2-methyl-2-propane-sulfinamide (1.76 g, 14.5 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure to afford 2-methyl-N-[(5-methylfuran-2-yl)methylidene]propane-2-sulfinamide (1.70 g, 88%) as orange oil. The compound was used as such for the next step. | |
| Ex. 8b | N-[(2,4-dimethylphenyl)(5-methylfuran-2-yl)methyl]-2-methylpropane-2-sulfinamide<br>Step 2: to a suspension of magnesium powder (239 mg, 9.79 mmol) in dry THF (small amount) was added dropwise 1-bromo-2,4-dimethylbenzene (1.64 g, 8.86 mmol) diluted in dry THF (20 mL) and the reaction was heated at 40° C. After completion of Grignard reagent, 2-methyl-N-[(5-methylfuran-2-yl)methylidene]propane-2-sulfinamide Ex. 8a (995 mg, 4.66 mmol) diluted in THF (10 mL) was added to the solution. The reaction mixture was stirred at rt overnight. Water was added to quench the reaction. The two layers were partitionated and the organic layer was dried over MgSO4, filtered and the solution was concentrated under reduced pressure. The crude material was purified by silica gel column chromatography using a gradient of hexanes/EtOAc ([5:1] to [4:1]) to afford N-[(2,4-dimethylphenyl)(5-methylfuran-2-yl)methyl]-2-methylpropane-2-sulfinamide (1.27 g, 85%) as yellowish oil. | |
| Ex. 8 | (2,4-dimethylphenyl)(5-methylfuran-2-yl)methanamine<br>Step 3: to a solution of N-[(2,4-dimethylphenyl)(5-methylfuran-2-yl)methyl]-2-methylpropane-2-sulfinamide Ex. 8b (683 mg, 2.14 mmol) dissolved in dry dioxane (5 mL) was added 4N HCl in dioxane (2.4 mL) at 0° C. The reaction mixture was stirred at this temperature for 2 h and then the solid was collected by filtration. The solid was triturated with Et2O and dried until constant weight to afford (2,4-dimethylphenyl)(5-methylfuran-2-yl)methanamine (194 mg, 36%) as white solid.<br>1H NMR (400 MHz, DMSO-d6, d in ppm): 2.24 (s, 3H); 2.29 (d, J = 4.7 Hz, 6H), 5.64 (s, 1H), 6.02-6.19 (m, 1H), 6.25 (d, 1H, J = 3.2 Hz), 7.09-7.16 (m, 1H), 7.44 (d, 1H, J = 8.0 Hz), 8.96 (s, 3H). | |

Example 2: Synthesis of the Compounds According to the Invention

Protocol A: to a solution of the substituted acid in DMF (0.25 mmol/mL) were added DMAP (2 to 4 equiv), EDCI.HCl (1 to 1.5 equiv) and the substituted amine (1 equiv). The reaction mixture was stirred at rt. After completion of the reaction (monitored by TLC), sat. NH4Cl or HCl 0.5N was added and the solution was extracted with EtOAc. The organic layer was washed with sat. NH4Cl, dried over MgSO4, filtered and evaporated to dryness under reduced pressure.

Protocol B:

Step 1: to a solution of 2-(6-bromopyridin-2-yl)acetic acid (266 mg, 1.23 mmol) in DMF (5 mL) were added DMAP (150 mg, 1.23 mmol), EDCI.HCl (279 mg, 1.35 mmol) and [4-methyl-2-(piperidin-1-yl)phenyl](5-methylfuran-2-yl)methanamine Ex.2 (350 mg, 1.23 mmol). The reaction mixture was stirred at rt. After completion of the reaction (monitored by TLC), sat. NH4Cl was added and the solution was extracted with EtOAc. The organic layer was washed with sat. NH4Cl, dried over MgSO4, filtered and evaporated to dryness under reduced pressure. The crude material was purified by column chromatography on silica gel using Cyclohexane/EtOAc (70:30) as eluent to afford 2-(6-bromopyridin-2-yl)-N-{[4-methyl-2-(piperidin-1-yl)phenyl](5-methylfuran-2-yl)methyl}acetamide (470 mg, 79%) as yellow oil. 1H NMR (300 MHz, DMSO-d6, d in ppm): 1.39-1.59 (m, 6H), 2.17 (s, 3H), 2.26 (s, 3H), 2.52-2.63 (m, 2H), 2.73-2.87 (m, 2H), 3.66 (s, 2H), 5.91 (d, 1H, J=3.3 Hz), 5.94 (dd, 1H, J=3.0 Hz, J=0.9 Hz), 6.49 (d, 1H, J=8.4 Hz), 6.91 (d, 1H, J=7.9 Hz), 6.95 (s, 1H), 7.20 (d, 1H, J=7.8 Hz), 7.35 (dd, 1H, J=7.5 Hz, J=0.6 Hz), 7.49 (dd, 1H, J=7.9 Hz, J=0.7 Hz), 7.68 (t, 1H, J=7.4 Hz), 8.86 (d, 1H, J=8.4 Hz).

Step 2: a solution of 2-(6-bromopyridin-2-yl)-N-{[4-methyl-2-(piperidin-1-yl)phenyl](5-methylfuran-2-yl)methyl}acetamide (1 equiv), substituted piperazine (2.5 equiv), Cs2CO3 (4 equiv), XPhos (0.1 equiv), Pd2(dba)3 (0.5 equiv) in dry toluene (0.31 mmol/mL) was refluxed under N2 atmosphere overnight. The reaction was monitored by TLC and quenched after completion with brine followed by EtOAc. The mixture was filtered through Celite. The two phases were separated and the organic layer was dried over MgSO4, filtered and the solution was concentrated under reduced pressure.

TABLE 2

| | | |
|---|---|---|
| | All the NMR were performed in DMSO-d6 | |
| Cpd. | | Starting compounds, Reaction conditions and purification Yield, MP, Appearance, 1H NMR (solvent) data, Mass (ES+ or ES−) data |
| 1 | 2-[6-(4-methanesulfonylpiperazin-1-yl)pyridin-3-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[6-(4-methanesulfonylpiperazin-1-yl)pyridin-3-yl]acetic acid Ex. 1 following protocol A, DMAP (2.2 equiv), EDCI•HCl (1.2 equiv), 48 h at rt, purification by silica gel column chromatography (Cyclohexane/EtOAc, 4:6), yield 74%, mp: 152° C., appearance: white solid<br>1H NMR (300 MHz, d in ppm): 1.46-1.51 (m, 6H), 2.17 (s, 3H), 2.25 (s, 3H), 2.54-2.59 (m, 2H), 2.77-2.80 (m, 2H), 2.88 (s, 3H), 3.16 (t, 4H, J = 4.8 Hz), 3.34 (s, 2H), 3.56 (t, 4H, J = 4.7 Hz), 5.81 (d, 1H, J = 3.0 Hz), 5.92 (dd, 1H, J = 2.9 Hz, J = 1.0 Hz), 6.48 (d, 1H, J = 8.4 Hz), 6.83 (d, 1H, J = 8.7 Hz), 6.89 (d, 1H, J = 7.7 Hz), 6.94 (s, 1H), 7.18 (d, 1H, J = 7.8 Hz), 7.44 (dd, 1H, J = 8.7 Hz, J = 2.4 Hz), 7.97 (d, 1H, J = 2.2 Hz), 8.73 (d, 1H, J = 8.5 Hz); m/z: 566 [M + H]+ (calc. mass: 565). |
| 2 | 2-[6-(4-methanesulfonylpiperidin-1-yl)pyridin-3-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[6-(4-methanesulfonylpiperidin-1-yl)pyridin-3-yl]acetic acid Ex. 3 following protocol A, DMAP (2.2 equiv), EDCI•HCl (1.2 equiv), 16 h at rt, purification by silica gel column chromatography (Cyclohexane/EtOAc, 4:6), yield 37%, mp: 84° C., appearance: white solid<br>1H NMR (300 MHz, d in ppm): 1.45-1.58 (m, 8H), 2.00-2.04 (m, 2H), 2.17 (s, 3H), 2.25 (s, 3H), 2.52-2.58 (m, 2H), 2.76-2.85 (m, 4H), 2.92 (s, 3H), 3.34-3.38 (m, 1H), 4.36-4.41 (m, 2H), 5.81 (d, 1H, J = 3.1 Hz), 5.92 (dd, 1H, J = 3.0 Hz, J = 1.0 Hz), 6.47 (d, 1H, J = 8.4 Hz), 6.81 (d, 1H, J = 8.8 Hz), 6.88 (d, 1H, J = 7.8 Hz), 6.94 (s, 1H), 7.16 (d, 1H, J = 7.8 Hz), 7.41 (dd, 1H, J = 8.8 Hz, J = 2.4 Hz), 7.95 (d, 1H, J = 2.2 Hz), 8.70 (d, 1H, J = 8.5 Hz); m/z: 565 [M + H]+ (calc. mass: 564). |
| 3 | tert-butyl 4-{5-[({[4-methyl-2-(piperidin-1-yl)phenyl](5-methylfuran-2-yl)methyl}carbamoyl)methyl]pyridin-2-yl}piperazine-1-carboxylate | From [4-methyl-2-(piperidin-1-yl)phenyl](5-methylfuran-2-yl)methanamine Ex. 2 and 2-(6-{4-[(tert-butoxy)carbonyl]piperazin-1-yl}pyridin-3-yl)acetic acid Ex. 4 following protocol A, DMAP (2.2 equiv), EDCI•HCl (1.2 equiv), 48 h at rt, purification by silica gel column chromatography (Cyclohexan/EtOAc, 4:6), yield 67%, mp: 75° C., appearance: white solid<br>1H NMR (300 MHz, d in ppm): 1.41 (s, 9H), 1.45-1.51 (m, 6H), 2.17 (s, 3H), 2.25 (s, 3H), 2.51-2.58 (m, 2H), 2.76-2.80 (m, 2H), 3.33 (s, 2H), 3.40 (br(s), 8H), 5.81 (d, 1H, |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| | J = 2.8 Hz), 5.92 (dd, 1H, J = 3.0 Hz, J = 1.0 Hz), 6.47 (d, 1H, J = 8.4 Hz), 6.77 (d, 1H, J = 8.7 Hz), 6.89 (d, 1H, J = 7.9 Hz), 6.94 (s, 1H), 7.17 (d, 1H, J = 7.8 Hz), 7.42 (dd, 1H, J = 8.8 Hz, J = 2.4 Hz), 7.96 (d, 1H, J = 2.2 Hz), 8.71 (d, 1H, J = 8.5 Hz); m/z: 588 [M + H]+ (calc. mass: 587). |
| 4  2-[2-(4-methanesulfonylpiperazin-1-yl)pyrimidin-5-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[2-(4-methanesulfonylpiperazin-1-yl)pyrimidin-5-yl]acetic acid Ex. 5 following protocol A, DMAP (2.2 equiv), EDCI•HCl (1.1 equiv), 18 h at rt, purification by preparative HPLC, yield 48%, mp: 132° C., appearance: white solid 1H NMR (300 MHz, d in ppm): 1.40-1.60 (m, 6H), 2.17 (s, 3H), 2.25 (s, 3H), 2.52-2.60 (m, 2H), 2.75-2.80 (m, 2H), 2.83 (s, 3H), 3.14 (t, 4H, J = 5.1 Hz), 3.38 (s, 2H), 3.79 (t, 4H, J = 5.3 Hz), 5.82 (d, 1H, J = 3.4 Hz), 5.93 (dd, 1H, J = 3.0 Hz, J = 1.0 Hz), 6.48 (d, 1H, J = 8.5 Hz), 6.90 (d, 1H, J = 8.3 Hz), 6.94 (s, 1H), 7.19 (d, 1H, J = 7.8 Hz), 8.24 (s, 2H), 8.79 (d, 1H, J = 8.6 Hz); m/z: 568 [M + H]+ (calc. mass: 566). |
| 5  2-[2-(4-methanesulfonylpiperidin-1-yl)pyrimidin-5-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[2-(4-methanesulfonylpiperidin-1-yl)pyrimidin-5-yl]acetic acid Ex. 6 following protocol A, DMAP (2.2 equiv), EDCI•HCl (1.1 equiv), 18 h at rt, purification by preparative HPLC, yield 51%, mp: 108° C., appearance: white solid 1H NMR (300 MHz, d in ppm): 1.40-1.60 (m, 8H), 2.03-2.07 (m, 2H), 2.17 (s, 3H), 2.25 (s, 3H), 2.52-2.60 (m, 2H), 2.7-2.78 (m, 2H), 2.85-2.90 (m, 2H), 2.92 (s, 3H), 3.30-3.340 (m, 3H), 4.73-4.77 (m, 2H), 5.79-5.86 (m, 1H), 5.89-5.98 (m, 1H), 6.42-6.52 (m, 1H), 6.85-6.92 (m, 1H), 6.93-6.99 (m, 1H), 7.13-7.21 (m, 1H), 8.22 (s, 2H), 8.71-8.81 (m, 1H); m/z: 567 [M + H]+ (calc. mass: 565). |
| 6  2-[2-(4-acetylpiperidin-1-yl)pyrimidin-5-yl]-N-[(2,4-dimethylphenyl)(5-methylfuran-2-yl)methyl]acetamide | From (2,4-dimethylphenyl)(5-methylfuran-2-yl)methanamine Ex. 8 and 2-[2-(4-acetylpiperidin-1-yl)pyrimidin-5-yl]acetic acid Ex. 7 following protocol A, substituted acid (1.2 equiv), DMAP (3.2 equiv), EDCI•HCl (1.2 equiv), 12 h at rt, purification by silica gel column chromatography (Cyclohexane/EtOAc, 3:7), yield 56%, mp: 170° C., appearance: white solid 1H NMR (300 MHz, d in ppm): 1.25-1.4 (m, 2H), 1.75-1.9 (m, 2H), 2.12 (s, 3H), 2.18 (s, 3H), 2.23 (s, 3H), 2.26 (s, 3H), 2.55-2.7 (m, 1H), 2.85-3.0 (m, 2H), 3.32 (s, 2H), 4.5-4.6 (m, 2H), 5.85 (d, 1H, J = 3.3 Hz), 5.90-6.0 (m, 1H), 6.09 (d, 1H, J = 8.3 Hz), 6.9-7.0 (m, 2H), 7.08 (d, 1H, J = 8.5 Hz), 8.20 (s, 2H), 8.96 (d, 1H, J = 8.3 Hz); m/z: 461 [M + H]+ (calc. mass: 460). |
| 7  methyl 1-{5-[({[4-methyl-2-(piperidin-1-yl)phenyl](5-methylfuran-2-yl)methyl}carbamoyl)methyl]pyrimidin-2-yl}piperidine-4-carboxylate | From [4-methyl-2-(piperidin-1-yl)phenyl](5-methylfuran-2-yl)methanamine Ex. 2 and 2-{2-[4-(methoxycarbonyl)piperidin-1-yl]pyrimidin-5-yl}acetic acid Ex. 9 following protocol A, DMAP (2.2 equiv), EDCI•HCl (1.2 equiv), 48 h at rt, purification by silica gel column chromatography (Cyclohexane/EtOAc, 4:6), yield 68%, mp: 59° C., appearance: white solid 1H NMR (300 MHz, d in ppm): 1.38-1.53 (m, 8H), 1.82-1.88 (m, 2H), 2.17 (s, 3H), 2.25 (s, 3H), 2.53-2.61 (m, 2H), 2.62-2.69 (m, 1H), 2.75-2.79 (m, 2H), 2.96-3.05 (m, 2H), 3.30 (s, 2H), 3.60 (s, 3H), 4.44-4.50 (m, 2H), 5.83 (d, 1H, J = 3.0 Hz), 5.93 (dd, 1H, J = 3.0 Hz, J = 1.1 Hz), 6.47 (d, 1H, J = 8.4 Hz), 6.89 (d, 1H, J = 7.8 Hz), 6.94 (s, 1H), 7.16 (d, 1H, J = 7.8 Hz), 8.19 (s, 2H), 8.75 (d, 1H, J = 8.4 Hz); m/z: 546 [M + H]+ (calc. mass: 545). |
| 8  2-[2-(4-acetylpiperidin-1-yl)pyrimidin-5-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[2-(4-acetylpiperidin-1-yl)pyrimidin-5-yl]acetic acid Ex. 7 following protocol A, DMAP (2.2 equiv), EDCI•HCl (1.2 equiv), 48 h at rt, purification by silica gel column chromatography (Cyclohexane/EtOAc, 5:5), yield 49%, mp: 62° C., appearance: white solid 1H NMR (300 MHz, d in ppm): 1.30-1.38 (m, 2H), 1.45-1.53 (m, 6H), 1.82-1.86 (m, 2H), 2.12 (s, 3H), 2.17 (s, 3H), 2.25 (s, 3H), 2.53-2.61 (m, 2H), 2.62-2.68 (m, 1H), 2.70-2.79 (m, 2H), 2.87-2.96 (m, 2H), 3.29 (s, 2H), 4.53-4.57 (m, |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| | | 2H), 5.83 (d, 1H, J = 2.9 Hz), 5.93 (dd, 1H, J = 3.0 Hz, J = 1.0 Hz), 6.47 (d, 1H, J = 8.3 Hz), 6.89 (d, 1H, J = 8.0 Hz), 6.94 (s, 1H), 7.16 (d, 1H, J = 7.8 Hz), 8.19 (s, 2H), 8.75 (d, 1H, J = 8.4 Hz); m/z: 530 [M + H]+ (calc. mass: 529). |
| 9 | 1-{5-[([[4-methyl-2-(piperidin-1-yl)phenyl](5-methylfuran-2-yl)methyl}carbamoyl)methyl]pyrimidin-2-yl}piperidine-4-carboxylicacid | to a solution of methyl 1-[5-[({[4-methyl-2-(piperidin-1-yl)phenyl](5-methylfuran-2-yl)methyl}carbamoyl)methyl]pyrimidin-2-yl}piperidine-4-carboxylate Cpd. 7 (109 mg, 0.20 mmol) in MeOH/THF (4:1, 0.8 mL/ 0.4 mL) was added 5N NaOH (200 μL, 1.00 mmol). The reaction mixture was heated under microwave irradiation at 100° C. for 30 min. The solvents were removed under reduced pressure. Water was added to dissolved inorganic salts. 1N citric acid was added until pH 4-5 was reached. The solid formed was collected by filtration, washed with water and dried until constant weight, yield 82%, mp: 89° C., appearance: pale yellow solid 1H NMR (300 MHz, d in ppm): 1.36-1.53 (m, 8H), 1.81-1.86 (m, 2H), 2.17 (s, 3H), 2.25 (s, 3H), 2.52-2.58 (m, 3H), 2.73-2.79 (m, 2H), 2.95-3.04 (m, 2H), 3.29 (s, 2H), 4.43-4.47 (m, 2H), 5.83 (d, 1H, J = 2.6 Hz), 5.93 (dd, 1H, J = 3.0 Hz, J = 1.1 Hz), 6.47 (d, 1H, J = 8.4 Hz), 6.89 (d, 1H, J = 7.9 Hz), 6.94 (s, 1H), 7.16 (d, 1H, J = 7.8 Hz), 8.19 (s, 2H), 8.74 (d, 1H, J = 8.4 Hz), 11.94 (br(s), 1H); m/z: 532 [M + H]+ (calc. mass: 531) |
| 10 | N-{[4-methyl-2-(piperidin-1-yl)phenyl](5-methylfuran-2-yl)methyl}-2-[6-(piperazin-1-yl)pyridin-3-yl]acetamide | to a solution of tert-butyl 4-{5-[({[4-methyl-2-(piperidin-1-yl)phenyl](5-methylfuran-2-yl)methyl}carbamoyl)methyl]pyridin-2-yl}piperazine-1-carboxylate Cpd. 3 (118 mg, 0.20 mmol) dissolved in EtOH (1.5 mL) was added 4N HCl in dioxane (251 μL, 1.00 mmol). The reaction mixture was heated at 40° C. for 4 h. Additional 4N HCl in dioxane (251 μL, 1.00 mmol) was added and the reaction mixture was stirred at 40° C. for 4h. The solvents were removed under reduced pressure. Sat. NaHCO3 was added and the aqueous layer was extracted with EtOAc. The organic layer was dried over MgSO4, filtered and the solution was concentrated under reduced pressure. The crude material was purified by preparative HPLC. The fractions of interest were collected and evaporated, yield 44%, mp: 100° C., appearance: white solid 1H NMR (300 MHz, d in ppm): 1.39-1.54 (m, 6H), 2.17 (s, 3H), 2.25 (s, 3H), 2.53-2.58 (m, 2H), 2.72-2.80 (m, 2H), 2.84 (t, 4H, J = 4.9 Hz), 3.40 (t, 4H, J = 4.9 Hz), 3.43 (s, 2H), 5.81 (d, 1H, J = 3.0 Hz), 5.92 (dd, 1H, J = 3.0 Hz, J = 1.1 Hz), 6.47 (d, 1H, J = 8.3 Hz), 6.75 (d, 1H, J = 8.7 Hz), 6.89 (d, 1H, J = 8.0 Hz), 6.94 (s, 1H), 7.17 (d, 1H, J = 7.8 Hz), 7.40 (dd, 1H, J = 8.7 Hz, J = 2.5 Hz), 7.95 (d, 1H, J = 2.2 Hz), 8.26 (s, 1H), 8.70 (d, 1H, J = 8.4 Hz); m/z: 488 [M + H]+ (calc. mass: 487) |
| 11 | 1-[2-(4-acetylpiperazin-1-yl)pyrimidin-5-yl]-N-{[4-methyl-2-(piperidin-1-yl)phenyl](5-methylfuran-2-yl)methyl}cyclopropane-1-carboxamide | From [4-methyl-2-(piperidin-1-yl)phenyl](5-methylfuran-2-yl)methanamine Ex. 2 and 1-[2-(4-acetylpiperazin-1-yl)pyrimidin-5-yl]cyclopropane-1-carboxylic acid Ex. 10 following protocol A, DMAP (2.2 equiv), EDCI•HCl (1.2 equiv), overnight at rt, purification by silica gel column chromatography (EtOAc, 100%), yield 59%, mp: 154° C., appearance: white solid 1H NMR (300 MHz, DMSO-d6, d in ppm): 0.95 (d, 2H, J = 2.8 Hz), 1.23-1.46 (m, 8H), 2.04 (s, 3H), 2.14 (s, 3H), 2.24 (s, 3H), 2.43-2.48 (m, 2H), 2.64-2.67 (m, 2H), 3.48-3.51 (m, 4H), 3.67-3.77 (m, 4H), 5.77 (d, 1H, J = 2.4 Hz), 5.92 (dd, 1H, J = 3.0 Hz, J = 1.0 Hz), 6.45 (d, 1H, J = 8.5 Hz), 6.86 (d, 1H, J = 7.8 Hz), 6.97 (s, 1H), 7.13 (d, 1H, J = 7.8 Hz), 7.79 (d, 1H, J = 8.9 Hz), 8.32 (s, 2H); m/z: 557 [M + H]+ (calc. mass: 556). |
| 12 | 2-[6-(4-acetylpiperazin-1-yl)pyridin-2-yl]-N-{[4-methyl-2-(piperidin-1-yl)phenyl](5-methylfuran-2-yl)methyl}acetamide | From 2-(6-bromopyridin-2-yl)-N-{[4-methyl-2-(piperidin-1-yl)phenyl](5-methylfuran-2-yl)methyl}acetamide (see step 1 - Protocol B) and 1-(piperazin-1-yl)ethan-1-one following protocol B, purification of the crude material (step 2) by column chromatography on silica gel (EtOAc, 100%), yield 30%, mp: 75° C., appearance: pale brown solid 1H NMR (300 MHz, DMSO-d6, d in ppm): 1.40-1.61 (m, 6H), 2.03 (s, 3H), 2.17 (s, 3H), 2.25 (s, 3H), 2.55-2.60 (m, 2H), 2.73-2.82 (m, 2H), 3.33-3.38 (m, 2H), 3.39-3.47 (m, 6H), 3.49 (s, 2H), 5.87 (d, 1H, J = 2.6 Hz), 5.93 (dd, 1H, J = 2.9 Hz, J = 1.0 Hz), 6.50 (d, 1H, J = 8.3 Hz), 6.58 (d, 1H, J = 7.2 Hz), 6.66 (d, 1H, J = 8.2 Hz), 6.89 (d, 1H, J = 8.0 Hz), |

TABLE 2-continued

All the NMR were performed in DMSO-d6

| Cpd. | Starting compounds, Reaction conditions and purification Yield, MP, Appearance, ¹H NMR (solvent) data, Mass (ES+ or ES−) data |
|---|---|
| | 6.95 (s, 1H), 7.19 (d, 1H, J = 7.8 Hz), 7.46 (m, 1H), 8.67 (d, 1H, J = 8.3 Hz); m/z: 530 [M + H]+ (calc. mass: 529). |
| 13 2-[2-(4-acetylpiperazin-1-yl)pyrimidin-5-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[2-(4-acetylpiperazin-1-yl)pyrimidin-5-yl]acetic acid Ex. 11 following protocol A, DMAP (2.2 equiv), EDCI•HCl (1.2 equiv), overnight at rt, purification by silica gel column chromatography (EtOAc, 100%), yield 68%, mp: 89° C., appearance: white soli1H NMR (300 MHz, DMSO-d6, d in ppm): 1.46-1.53 (m, 6H), 2.03 (s, 3H), 2.17 (s, 3H), 2.25 (s, 3H), 2.51-2.60 (m, 2H), 2.76-2.80 (m, 2H), 3.31 (s, 2H), 3.48 (t, 4H, J = 4.6 Hz), 3.65 (t, 2H, J = 4.5 Hz), 3.72 (t, 2H, J = 5.0 Hz), 5.83 (d, 1H, J = 3.0 Hz), 5.93 (dd, 1H, J = 3.0 Hz, J = 1.0 Hz), 6.48 (d, 1H, J = 8.3 Hz), 6.90 (d, 1H, J = 7.9 Hz), 6.94 (s, 1H), 7.18 (d, 1H, J = 7.8 Hz), 8.23 (s, 2H), 8.77 (d, 1H, J = 8.4 Hz); m/z: 531 [M + H]+ (calc. mass: 530). |
| 14 2-[5-(4-acetylpiperazin-1-yl)pyridin-3-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[5-(4-acetylpiperazin-1-yl)pyridin-3-yl]acetic acid Ex. 12 following protocol A, DMAP (1 equiv), EDCI•HCl (1.1 equiv), overnight at rt, purification by silica gel column chromatography (Acetone, 100%), yield 13%, mp: 90° C., appearance: white solid 1H NMR (300 MHz, DMSO-d6, d in ppm): 1.40-1.59 (m, 6H), 2.04 (s, 3H), 2.17 (s, 3H), 2.25 (s, 3H), 2.55-2.59 (m, 2H), 2.73-2.80 (m, 2H), 3.05-3.11 (m, 2H), 3.13-3.20 (m, 2H), 3.43 (s, 2H), 3.55 (t, 4H, J = 5.0 Hz), 5.82 (d, 1H, J = 3.3 Hz), 5.93 (dd, 1H, J = 3.1 Hz, J = 1.4 Hz), 6.49 (d, 1H, J = 8.1 Hz), 6.89 (d, 1H, J = 7.1 Hz), 6.94 (s, 1H), 7.15-7.24 (m, 2H), 7.88 (d, 1H, J = 1.4 Hz), 8.15 (d, 1H, J = 2.8 Hz), 8.81 (d, 1H, J = 8.4 Hz); m/z: 530 [M + H]+ (calc. mass: 529). |
| 15 2-[2-(4-acetylpiperazin-1-yl)pyrimidin-4-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[2-(4-acetylpiperazin-1-yl)pyrimidin-4-yl]acetic acid Ex. 13 following protocol A, DMAP (1 equiv), EDCI•HCl (1.1 equiv), overnight at rt, purification by silica gel column chromatography (Acetone, 100%), yield 4%, mp: 88° C., appearance: white solid 1H NMR (300 MHz, DMSO-d6, d in ppm): 1.44-1.61 (m, 6H), 2.03 (s, 3H), 2.17 (s, 3H), 2.26 (s, 3H), 2.41-2.44 (m, 2H), 2.77-2.84 (m, 2H), 3.26-3.30 (m, 4H), 3.42-3.49 (m, 4H), 3.56 (s, 2H), 5.91 (d, 1H, J = 3.6 Hz), 5.92-5.96 (m, 1H), 6.52 (d, 1H, J = 8.9 Hz), 6.67 (d, 1H, J = 6.0 Hz), 6.90 (d, 1H, J = 7.0 Hz), 6.96 (s, 1H), 7.23 (d, 1H, J = 7.8 Hz), 8.12 (d, 1H, J = 6.1 Hz), 8.74 (d, 1H, J = 9.0 Hz); -m/z: 531 [M + H]+ (calc. mass: 530). |
| 16 N-{[4-methyl-2-(piperidin-1-yl)phenyl](5-methylfuran-2-yl)methyl}-2-{6-[4-(trifluoroacetyl)piperazin-1-yl]pyridin-2-yl}acetamide | From 2-(6-bromopyridin-2-yl)-N-{[4-methyl-2-(piperidin-1-yl)phenyl](5-methylfuran-2-yl)methyl}acetamide (see step 1 - Protocol B) and 2,2,2-trifluoro-1-(piperazin-1-yl)ethan-1-one following protocol B, purification of the crude material (step 2) by column chromatography on silica gel (CH2Cl2/EtOAc, 95:5), yield 12%, mp: 65° C., appearance: white solid 1H NMR (300 MHz, DMSO-d6, d in ppm): 1.40-1.59 (m, 6H), 2.17 (s, 3H), 2.25 (s, 3H), 2.56-2.60 (m, 2H), 2.74-2.82 (m, 2H), 3.43-3.53 (m, 6H), 3.53-3.63 (m, 4H), 5.86 (d, 1H, J = 2.9 Hz), 5.93 (dd, 1H, J = 2.9 Hz, J = 0.9 Hz), 6.51 (d, 1H, J = 8.2 Hz), 6.61 (d, 1H, J = 7.5 Hz), 6.67 (d, 1H, J = 8.7 Hz), 6.88 (d, 1H, J = 8.4 Hz), 6.94 (s, 1H), 7.21 (d, 1H, J = 7.9 Hz), 7.49 (dd, 1H, J = 7.6 Hz, J = 7.1 Hz), 8.68 (d, 1H, J = 8.7 Hz); m/z: 584 [M + H]+ (calc. mass: 583). |
| 17 2-[2-(3-methanesulfonylpiperidin-1-yl)pyrimidin-5-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 2 and 2-[2-(3-methanesulfonylpiperidin-1-yl)pyrimidin-5-yl]acetic acid Ex. 14 following protocol A, DMAP (2.2 equiv), EDCI•HCl (1.2 equiv), overnight at rt, purification by silica gel column chromatography (Cyclohexane/EtOAc, 30:70), yield 95%, mp: 87° C., appearance: white solid 1H NMR (300 MHz, DMSO-d6, d in ppm): 1.39-1.52 (m, 7H), 1.68-1.82 (m, 2H), 2.15-2.18 (m, 4H), 2.25 (s, 3H), 2.56-2.60 (m, 2H), 2.74-2.80 (m, 2H), 2.82-2.91 (m, 1H), 2.98 (s, 3H), 3.01-3.09 (m, 1H), 3.12-3.16 (m, 1H), 3.33 (s, |

TABLE 2-continued

All the NMR were performed in DMSO-d6

| Cpd. | Starting compounds,<br>Reaction conditions and purification<br>Yield, MP, Appearance, $^1$H NMR (solvent) data, Mass<br>(ES+ or ES−) data |
|---|---|
| | 2H), 4.54 (d, 1H, J = 12.6 Hz), 4.97 (d, 1H, J = 11.8 Hz), 5.83<br>(d, 1H, J = 3.0 Hz), 5.93 (d, 1H, J = 3.0 Hz), 6.48 (d, 1H,<br>J = 8.4 Hz), 6.90 (d, 1H, J = 8.1 Hz), 6.94 (s, 1H), 7.18 (dd, 1H,<br>J = 7.8 Hz, J = 1.2 Hz), 8.24 (s, 2H), 8.79 (d, 1H, J = 8.4 Hz);<br>m/z: 566 [M + H]+ (calc. mass: 565). |

Example 3: RORE Luciferase/RORγt Transactivation Assay

It is well known that RORγ binds to a conserved non-coding sequence (CNS) enhancer element in the IL-17 promoter. Accordingly, we have used in this assay a luciferase reporter gene construct that contains the human IL-17 promoter fragment with RORγ-specific CNS enhancer element and a RORγt overexpressing plasmid, to indirectly assess the effect of compounds on RORγ activity. Inhibition of RORγ activity by test compounds will result in a decrease in luciferase activity in COS-7 cells transfected with the reporter construct.

COS-7 Cell Line Culture

Monkey Kidney COS-7 cell line are maintained in a standard culture medium Dulbecco's modified Eagle's minimal (DMEM) medium supplemented with 10% fetal calf serum, 1% sodium pyruvate, 1% essential amino acids and 1% antibiotics at 37° C. in a humidified atmosphere of 5% CO2 and 95% air. Culture medium was changed every 2 days.

Construct Descriptions

The 4.3 Kb human IL-17 promoter containing the RORγ-specific CNS enhancer element was PCR amplified from human genomic DNA and cloned into a pGL3-TKLuc2Cp reporter plasmid. To overexpress RORγt, the full-length cDNA of human RORγt (identical to published sequence NM 001001523) was cloned without any restriction into pcdna3.1DV5-His-topo to generate the RORγt overexpression plasmid "RORγt_FL_h_pcDNA3.1DV5-His-TOPO_1".

COS-7 Cell Transfection

The luciferase reporter plasmid and the RORγt overexpression plasmid were transfected into COS-7 cell line using 4 μLJetPEITM/μg of DNA. Briefly, 150 ng of DNA (ration ½ between RORE-Tk Luc2Cp and cDNA RORγt or the empty vector for the negative control) was served to transfect adherent COS-7 cells in a 225 cm3 culture flask, in complete medium (see cos-7 cell line culture). Cells were incubated for 24 hours in a humidified atmosphere of 5% CO2 and 95% air Cells were then detached (using trypsin) and washed by centrifugation at 300 g for 10 minutes. Cell pellet was resuspended in serum free/phenol red free DMEM and seeded in 384 well plates at a density of 10000 cells/well and then incubated for 4h at 37° C.

Assay

Compounds were dissolved in 100% DMSO to obtain 10 mM stock solutions. For each compound, test concentrations were diluted in serum free/phenol red free DMEM using the Genesis Freedom 200™ (TECAN) and added to the cells to obtain a 0.3% DMSO final concentration (in a final volume of 40 μL per well). T091317 was used as reference compound. Cells were incubated in presence of compounds for an additional 20 h at 37° C. in a humidified atmosphere of 5% CO2 and 95% air.

The luciferase activity was then measured with 40 μL/well steady-Glo Luciferase assay system (Promega, Madison, WI) and after incubation at room temperature for 30 minutes. The luminescence was estimated using the Ultra384 reader (TECAN). Data were collected and analyzed using GraphPad Prism software (GraphPad Software V5.02, San Diego California USA). IC50 in μM and Emax in % were reported for each compound.

Results:

Effect of reference compound on RORγt activity: in this assay, reference compound T091317 showed on RORγt activity inhibition with $IC_{50}$ of 0.2 μM and an Emax of 83.7%.

Several compounds belonging to formula (I) inhibit the high transcriptional activity of RORγ at different levels. These compounds displayed an $IC_{50}$ comprised between 1 and 10 μM in particular Cpds.6, 7, and 9. Cpds 1-5, 8, 10, and 13-16 displayed an $IC_{50}$ comprised between 0.1 and 1 μM. Best compounds (such as Cpds. 11, 12 and 17) displayed an $IC_{50}$ inferior to 0.1 μM.

Further, the major part of compounds from this chemical series showed no cytotoxic effect at 30 μM as judged from the reporter signal obtained from cells transfected with the empty vector that was used as negative control in this experiment.

Example 4: FRET

General Considerations

Time-resolved FRET (TR-FRET) RORγt coactivator assay was used to identify RORγ modulator compounds with ligand-dependent coactivator displacement. The assay uses a d2-labeled anti-GST antibody, synthetic N-terminally biotinylated peptide which is derived from nuclear receptor coactivator protein RIP140, and a RORγt ligand-binding domain (RORγt-LBD) that is tagged with glutathione-S-transferase (GST). The influence of compounds on the RORγ-peptide interaction relies on the binding dependent energy transfer from a donor to an acceptor fluorophor attached to the binding partner of interest. Because RORγ is constitutively active, streptavidin-terbium conjugate labeled-coactivator peptide is recruited in the absence of ligand and the terbium d2 on the anti-GST antibody is excited at 340 nm, energy is transferred to the terbium label on the coactivator peptide and detected as emission at 665 nm. For reduction of background from compound fluorescence, TR-FRET method makes use of generic fluorophore labels and time resolved detection.

Assay

The assays were done in a final volume of 20 µl in a 384 well plate in a CHAPS buffer (2 mM CHAPS; 1 mM DTT, 2 mM EDTA; 0.1% BSA), containing 20 nM recombinantly expressed RORγ-LBD fused to GST, 30 nM N-terminally biotinylated peptide, 1 nM streptavidin-terbium conjugate and 20 nM d2 labeled-anti-GST. Test compounds were diluted using 10 mM stock solution. The range of the final compound concentrations used in this test was from 0.3 nM to 30 µM (logarithmic scale). DMSO content of the samples was kept at 1%. The assay was equilibrated for 2 hours in the dark at room temperature in 384 well plates (Falcon). The signal was detected by an Ultra384 reader (TECAN). The results were visualized by plotting the ratio between the emitted light at 665 nm and 620 nm. A basal level of RORγ-peptide formation is observed in the absence of added compound. Compounds that promote coactivator displacement induce a concentration-dependent decrease in time-resolved fluorescent signal. Data were collected and analyzed using GraphPad Prism software (GraphPad Software V5.02, San Diego California USA). IC50 in µM and Emax in % were reported for each compound.

Results:

Effect of reference compound on RORγt activity: in this assay, reference compound T091317 showed on RORγt activity inhibition with $IC_{50}$ of 0.097 µM and an Emax of 37%

Several compounds belonging to formula (I) inhibit the ligand-dependent coactivator-RORγRORγt binding.

Cpds 3, 6-8, and 16 displayed an IC50 comprised between 0.1 µM and 1 µM.

Best compounds (such as Cpds.1-2, 4-5, 9-15, and 17) displayed an $IC_{50}$ inferior to 0.1 µM.

Example 5: IL-17 Secretion from EL4 Murine Lymphoma

Murine EL-4 lymphoma cell line overexpressing human RORγt was used in this functional assay to assess compound ability to inhibit IL-17 cytokine secretion.

EL-4 Cell Transfection

EL-4 cells are maintained in a standard culture medium RPMI supplemented with 10% fetal calf serum, 1% sodium pyruvate, 1% essential amino acids and 1% antibiotics at 37° C. in a humidified atmosphere of 5% CO2 and 95% air. Culture medium was changed every 2 days. EL4 cells were transfected with a plasmid encoding hRORγt (sequence identical to published sequence NM 001001523). Transfection of EL4 cells was achieved with Amaxa electroporation apparatus (Amaxa Biosystems, Germany), as per the manufacturer's protocols, for the EL4 cells (Amaxa Cell Line Nucleofector Kit L, Amaxa Biosystems). Briefly, 1 µg of DNA/1 million cells was served to transfect EL-4 cells. Cell/DNA suspension was transferred into certified cuvette and the electroporation of RORγt plasmid was carried out using appropriate Nucleofector® program.

IL-17 Secretion Assay

Cells were seeded in 96 well plates at a density of 150000 cells/well then treated with compounds of this invention at indicated concentrations and incubated for 24 hours at 37° C. in a humidified atmosphere of 5% CO2 and 95% air. EL-4 cells were pretreated with test compounds (RORγ modulators) and stimulated with PMA (10 ng/mL) and ionomycin (1 µM final concentration) in the presence of test compound concentrations for additional 24h at 37° C. in a humidified atmosphere of 5% CO2 and 95% air. Subsequently, supernatants were collected (after centrifugation at 300 g for 10 minutes) to determine the concentrations of IL-17 by HTRF (CisBio, France) or ELISA (R&D Systems Europe) according to the manufacturer's protocols.

Results:

Many of the compounds listed above were evaluated for IL-17 secretion inhibition in human RORγt-transfected EL4 Tcells. Data from this assay correlate with the activity observed in RORE Tk luc/RORγt assay.

All tested compounds displayed an $IC_{50}$ inferior to 1 µM.

REFERENCES

Armarego W L F, Chai C L L (2009) *Purification of Laboratory Chemicals (Sixth Edition)*: ELSEVIER.

Bauer M (2004) *Polymorphisme et stabilité*, Paris, FRANCE: Editions de santé.

Crispín J C, Oukka M, Bayliss G, Cohen R A, Van Beek C A, Stillman I E, Kyttaris V C, Juang Y-T, Tsokos G C (2008) Expanded Double Negative T Cells in Patients with Systemic Lupus Erythematosus Produce IL-17 and Infiltrate the Kidneys. *The Journal of Immunology* 181: 8761-8766

Dang Eric V, Barbi J, Yang H-Y, Jinasena D, Yu H, Zheng Y, Bordman Z, Fu J, Kim Y, Yen H-R, Luo W, Zeller K, Shimoda L, Topalian Suzanne L, Semenza Gregg L, Dang Chi V, Pardoll Drew M, Pan F (2011) Control of TH17/Treg Balance by Hypoxia-Inducible Factor 1. *Cell* 146: 772-784

Eberl G, Marmon S, Sunshine M J, Rennert P D, Choi Y, Littman D R (2004) An essential function for the nuclear receptor RORgamma(t) in the generation of fetal lymphoid tissue inducer cells. *Nat Immunol* 5: 64-73

Erdemir D, Lee A Y, Myerson A S (2007) Polymorph selection: the role of nucleation, crystal growth and molecular modeling. *Curr Opin Drug Discov Devel* 10: 746-755

Furuzawa-Carballeda J, Vargas-Rojas M I, Cabral A R (2007) Autoimmune inflammation from the Th17 perspective. *Autoimmunity Reviews* 6: 169-175

Gennaro A (2000) *Remington: The Science and Practice of Pharmacy-20th edition*: Baltimore, Md.; Lippincott Williams & Wilkins.

He Y-W, Deftos M L, Ojala E W, Bevan M J (1998) RORγt, a Novel Isoform of an Orphan Receptor, Negatively Regulates Fas Ligand Expression and IL-2 Production in T Cells. *Immunity* 9: 797-806

Hirose T, Smith R J, Jetten A M (1994) ROR-γ: The Third Member of ROR/RZR Orphan Receptor Subfamily That Is Highly Expressed in Skeletal Muscle. *Biochemical and Biophysical Research Communications* 205: 1976-1983

Korn T, Bettelli E, Oukka M, Kuchroo V K (2009) IL-17 and Th17 Cells. *Annual Review of Immunology* 27: 485-517

Kumar L, Amin A, Bansal A K (2007) An overview of automated systems relevant in pharmaceutical salt screening. *Drug Discov Today* 12: 1046-1053

Lipp M, Muller G (2004) Lymphoid organogenesis: getting the green light from RORgamma(t). *Nat Immunol* 5: 12-14

Liu S-J, Tsai J-P, Shen C-R, Sher Y-P, Hsieh C-L, Yeh Y-C, Chou A-H, Chang S-R, Hsiao K-N, Yu F-W, Chen H-W (2007) Induction of a distinct CD8 Tnc17 subset by transforming growth factor-β and interleukin-6. *Journal of Leukocyte Biology* 82: 354-360

Lubberts E, Koenders M I, Oppers-Walgreen B, van den Bersselaar L, Coenen-de Roo C J J, Joosten L A B, van den Berg W B (2004) Treatment with a neutralizing anti-murine interleukin-17 antibody after the onset of collagen-induced arthritis reduces joint inflammation, cartilage destruction, and bone erosion. *Arthritis & Rheumatism* 50: 650-659 Mahato R, Narang A (2011) *Pharmaceutical Dosage Forms and Drug Delivery, Second Edition*: CRC Press.

Morissette S L, Almarsson O, Peterson M L, Remenar J F, Read M J, Lemmo A V, Ellis S, Cima M J, Gardner C R (2004) High-throughput crystallization: polymorphs, salts, co-crystals and solvates of pharmaceutical solids. *Adv Drug Deliv Rev* 56: 275-300

Murdoch J R, Lloyd C M (2010) Resolution of Allergic Airway Inflammation and Airway Hyperreactivity Is Mediated by IL-17-producing γδT Cells. *American Journal of Respiratory and Critical Care Medicine* 182: 464-476

Mutlib A E (2008) Application of stable isotope-labeled compounds in metabolism and in metabolism-mediated toxicity studies. *Chem Res Toxicol* 21: 1672-1689

Ortiz M A, Piedrafita F J, Pfahl M, Maki R (1995) TOR: a new orphan receptor expressed in the thymus that can modulate retinoid and thyroid hormone signals. *Molecular Endocrinology* 9: 1679-1691

Rachitskaya A V, Hansen A M, Horai R, Li Z, Villasmil R, Luger D, Nussenblatt R B, Caspi R R (2008) Cutting Edge: NKT Cells Constitutively Express IL-23 Receptor and RORγt and Rapidly Produce IL-17 upon Receptor Ligation in an IL-6-Independent Fashion. *Journal of immunology* (Baltimore, Md.: 1950) 180: 5167-5171

Reddy I K, Mehvar R (2004) *Chirality in Drug Design and Development*: CRC Press. Rowe R, Sheskey P, Weller P, Rowe R, Sheskey P, Weller P (2003) *Handbook of Pharmaceutical Excipients, 4th Edition*.

Skepner J, Ramesh R, Trocha M, Schmidt D, Baloglu E, Lobera M, Carlson T, Hill J, Orband-Miller L A, Barnes A, Boudjelal M, Sundrud M, Ghosh S, Yang J (2014) Pharmacologic inhibition of RORgammat regulates Th17 signature gene expression and suppresses cutaneous inflammation in vivo. *J Immunol* 192: 2564-2575

Solt L A, Kumar N, Nuhant P, Wang Y, Lauer J L, Liu J, Istrate M A, Kamenecka T M, Roush W R, Vidovic D, Schurer S C, Xu J, Wagoner G, Drew P D, Griffin P R, Burris T P (2011) Suppression of TH17 differentiation and autoimmunity by a synthetic ROR ligand. *Nature* 472: 491-494

Stahl P, Wermuth C (2002) *Handbook of Pharmaceutical Salts: Properties, Selection, and Use*: Verlag Helvetica Chimica Acta, Zurich, Switzerland, and Wiley-VCH, Weinheim, Germany Stockinger B, Veldhoen M, Martin B (2007) Th17 T cells: Linking innate and adaptive immunity. *Seminars in Immunology* 19: 353-361

Tuskey A, Behm B W (2014) Profile of ustekinumab and its potential in patients with moderate-to-severe Crohn's disease. *Clinical and Experimental Gastroenterology* 7: 173-179 Wuts P G M, Greene T W (2007) *Greene's Protective Groups in Organic Synthesis, Fourth Edition*: John Wiley & Sons.

Yamashita T, Iwakura T, Matsui K, Kawaguchi H, Obana M, Hayama A, Maeda M, Izumi Y, Komuro I, Ohsugi Y, Fujimoto M, Naka T, Kishimoto T, Nakayama H, Fujio Y (2011) *IL-6-mediated Th17 differentiation through RORγt is essential for the initiation of experimental autoimmune myocarditis*, Vol. 91.

Yang X O, Pappu B, Nurieva R, Akimzhanov A, Kang H S, Chung Y, Ma L, Shah B, Panopoulos A D, Schluns K, Watowich S S, Tian Q, Jetten A M, Dong C (2008) TH17 lineage differentiation is programmed by orphan nuclear receptors RORα and RORγ. *Immunity* 28: 29-39

Yin S X, Grosso J A (2008) Selecting and controlling API crystal form for pharmaceutical development—strategies and processes. *Curr Opin Drug Discov Devel* 11: 771-777

The invention claimed is:
1. A compound of formula (I)

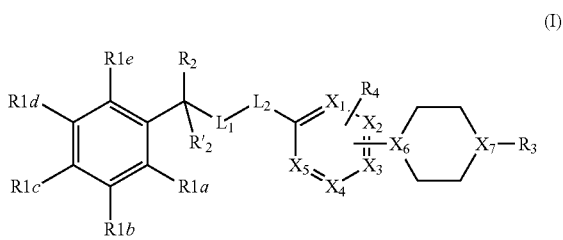

in which,

R1a is a hydrogen atom, a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, or a heterocyclic group;

R1b is a hydrogen atom, a (C1-C6)alkyloxy group, a (C1-C6)alkyl group, or a heterocyclic group;

R1c is a hydrogen atom, a halogen atom, a (C1-C6)alkyl group, a (C1-C6)alkyloxy group, a (C1-C6)alkylthio group, a heterocyclic group, a cyano group, an amido group, or a hydroxyl group;

R1d and R1e are, independently, a hydrogen atom, a halogen atom, a (C1-C6)alkyloxy group, or a (C1-C6) alkyl group;

wherein at least one of R1a, R1b, R1c, R1d, and R1e is not a hydrogen atom;

R2 is a (C1-C6)alkyl group optionally substituted by a (C1-C6)alkyl group, a (C2-C6)alkenyl group optionally substituted by a (C1-C6)alkyl group, a (C2-C6) alkynyl group optionally substituted by a (C1-C6)alkyl group, a (C3-C14)cycloalkyl group optionally substituted by a (C1-C6)alkyl group, a (C6-C14)aryl group optionally substituted by a (C1-C6)alkyl group, or a heterocyclic group optionally substituted by a (C1-C6) alkyl group;

R'2 is a hydrogen atom, a (C1-C6)alkyl group, a (C2-C6) alkenyl group, a (C2-C6)alkynyl group, a (C3-C14) cycloalkyl group, a (C6-C14)aryl group optionally substituted by a (C1-C6)alkyl group, or a heterocyclic group optionally substituted by a (C1-C6)alkyl group;

or R2 and R'2, together with the carbon atom to which they are attached, form a cycloalkyl group or a heterocycloalkyl group;

L1 is a NR7-CO—CH2, NR7-CO—, NR7-CO—C(CH3)2, CO—NH—CH2, CO—NH, or CO—NH—C(CH3)2 group;

R7 is a hydrogen atom or a (C1-C6)alkyl group;

L2 represents a bond, a (C1-C6)alkyl group, a (C3-C14) cycloalkyl group, or a CR8R'8 group;

with the proviso that when L1 is a NR3-CO— or a CO—NH group, L2 represents a (C1-C6)alkyl group, a (C3-C14)cycloalkyl group, or a CR8R'8 group;

R8 and R'8 are independently a hydrogen atom or a (C1-C6)alkyl group, or R8 and R'8, together with the carbon atom to which they are attached, form a cycloalkyl group;

X1, X2, X3, X4 and X5 are, independently, a CH group, a C-R4 group, a C—X6 group, or a nitrogen atom;

wherein two and only two of X1, X2, X3, X4, and X5 are nitrogen atoms, and said nitrogen atoms are in 1-position and 3-position;

X6 and X7 are independently a CH group or a nitrogen atom;

R3 is a hydrogen atom, a carbonyl(C1-C6)alkyl group, a SO2R' group, a COOR' group, an amido group, a (C1-C6)alkylamido group, or a (C1-C6)dialkylamido group;

R' is a (C1-C6)alkyl group; and

R4 is a hydrogen atom, a (C1-C6)alkyl group, or a halogen atom.

2. The compound according to claim 1, wherein X2 and X4 are nitrogen atoms.

3. The compound according to claim 1, wherein:

R1a is a hydrogen atom, a halogen atom, a nitrile group, a nitro group (NO2), a (C1-C6)alkyl group, a (C1-C6) alkyloxy group, a (C1-C6)alkylthio group, an amino group, a (C1-C6)alkylamino group, a (C1-C6)dialkylamino group, a piperidinyl group, a pyrrolidinyl group, or an azepanyl group, wherein said piperidinyl, pyrrolidinyl, or azepanyl group is optionally substituted by at least one (C1-C6)alkyl group;

R1b is a hydrogen atom;

R1c is a (C1-C6)alkyl group;

R2 is a (C1-C6)alkyl group, a (C3-C14)cycloalkyl group, an (C6-C14)aryl group, or a heteroaryl group; and R'2 is a hydrogen atom.

4. The compound according to claim 1, wherein X6 is a nitrogen atom and X7 is a CH group.

5. The compound according to claim 1, wherein L1 is a NR7-CO—CH2, NR7-CO—C(CH3)2, CO—NH—CH2, or CO—NH—C(CH3)2 group and L2 is a bond.

6. The compound according to claim 1, wherein L1 is a NR7-00- or —CO—NH— group and L2 is a cyclopropyl group of formula (III)

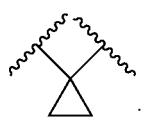

(III)

7. The compound according to claim 1, wherein R1b is a hydrogen atom.

8. The compound according to claim 1, wherein R1d and R1e each are a hydrogen atom.

9. The compound according to claim 1, wherein

R1a is a heterocyclic group,

R1c is a (C1-C6)alkyl group,

R2 is a heterocyclic group,

L1 represents a NH—CO—CH2 group,

L2 is a bound, the cycle

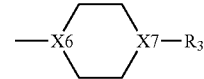

is in para or meta position of the L group,

X6 is a nitrogen atom,

X7 is a CH group, and

R3 represents a hydrogen atom, a carbonyl(C1-C6)alkyl group, a SO2R' group, or a COOR' group.

10. The compound according to claim 1, characterized in that it is selected from the group consisting of:

2[2-(4-methanesulfonylpiperazin-1-yl)pyrimidin-5-yl]-N-{[4-methyl-2-(piperidin-1-yl)phenyl](5-methylfuran-2-yl)methyl}acetamide;

2[2-(4-methanesulfonylpiperidin-1-yl)pyrimidin-5-yl]-N-{[4-methyl-2-(piperidin-1-yl)phenyl](5-methylfuran-2-yl)methyl}acetamide;

2[2-(4-acetylpiperidin-1-yl)pyrimidin-5-yl]-N-[(2,4-dimethylphenyl)(5-methylfuran-2-yl)methyl]acetamide;

methyl 1-{5-[({[4-methyl-2-(piperidin-1-yl)phenyl](5-methylfuran-2-yl)methyl}carbamoyl)methyl]pyrimidin-2-yl}piperidine-4-carboxylate;

2[2-(4-acetylpiperidin-1-yl)pyrimidin-5-yl]-N-{[4-methyl-2-(piperidin-1-yl)phenyl](5-methylfuran-2-yl)methyl}acetamide;

1-{5-[({[4-methyl-2-(piperidin-1-yl)phenyl](5-methylfuran-2-yl)methyl}carbamoyl)methyl]pyrimidin-2-yl}piperidine-4-carboxylic acid;

1-[2-(4-acetylpiperazin-1-yl)pyrimidin-5-yl]-N-{[4-methyl-2-(piperidin-1-yl)phenyl](5-methylfuran-2-yl)methyl}cyclopropane-1-carb oxamide;

2[2-(4-acetylpiperazin-1-yl)pyrimidin-5-yl]-N-{[4-methyl-2-(piperidin-1-yl)phenyl](5-methylfuran-2-yl)methyl}acetamide; and 2-[2-(3-methanesulfonylpiperidin-1-yl)pyrimidin-5-yl]-N-{[4-methyl-2-(piperidin-1-yl)phenyl](5-methylfuran-2-yl)methyl}acetamide.

11. A combination product comprising:

i) a compound of formula (I) as defined in claim 1, or a pharmaceutically acceptable salt thereof; and ii) another therapeutically active agent that is a PPAR activator selected from the group consisting of seladelpar, saroglitazar, lanifibranor, pioglitazone, and pharmaceutically acceptable salts thereof.

12. The combination product according to claim 11, wherein the combination product is a composition comprising component i), component ii), and a pharmaceutically acceptable carrier.

13. The combination product according to claim 11, wherein the combination product is a kit of parts comprising components i) and ii), for sequential, separate or simultaneous use.

14. The combination product according to claim 11, wherein components i) and ii) are formulated in an injectable suspension, a gel, an oil, a pill, a tablet, a suppository, a powder, a capsule, an aerosol, an ointment, a cream, a patch, or means of galenic forms for a prolonged and/or slow release.

* * * * *